US012090125B2

(12) United States Patent
Paldánius et al.

(10) Patent No.: US 12,090,125 B2
(45) Date of Patent: *Sep. 17, 2024

(54) COMBINATION THERAPY

(71) Applicant: Novartis AG, Basel (CH)

(72) Inventors: Päivi M. Paldánius, Helsinki (FI); Wolfgang Kothny, Lörrach (DE); James E. Foley, Sparta, NJ (US); David R. Matthews, Oxford (GB); Michael Stumvoll, Leipzig (DE); Stefano Del Prato, Pisa (IT)

(73) Assignee: Novartis AG, Basel (CH)

( * ) Notice: Subject to any disclaimer, the term of this patent is extended or adjusted under 35 U.S.C. 154(b) by 38 days.

This patent is subject to a terminal disclaimer.

(21) Appl. No.: 17/385,008

(22) Filed: Jul. 26, 2021

(65) Prior Publication Data
US 2022/0184006 A1 Jun. 16, 2022

Related U.S. Application Data

(63) Continuation of application No. 17/023,539, filed on Sep. 17, 2020, now Pat. No. 11,103,469.

(60) Provisional application No. 63/004,230, filed on Apr. 2, 2020, provisional application No. 62/901,645, filed on Sep. 17, 2019.

(51) Int. Cl.
*A61K 31/155* (2006.01)
*A61K 31/40* (2006.01)
*A61P 3/10* (2006.01)

(52) U.S. Cl.
CPC ............ *A61K 31/155* (2013.01); *A61K 31/40* (2013.01); *A61P 3/10* (2018.01)

(58) Field of Classification Search
CPC .......... A61K 31/155; A61K 31/40; A61P 3/10
See application file for complete search history.

(56) References Cited

U.S. PATENT DOCUMENTS

| 8,232,281 B2 | 7/2012 | Dugi et al. | |
| 11,103,469 B2 * | 8/2021 | Paldánius | .............. A61K 31/40 |

FOREIGN PATENT DOCUMENTS

| EP | 1741446 B1 | 2/2008 |
| EP | 1965783 B1 | 6/2013 |
| EP | 1084705 B1 | 6/2014 |
| WO | WO-2005/049022 A2 | 6/2005 |
| WO | WO-2005/117861 A1 | 12/2005 |
| WO | WO-2006/047248 A1 | 5/2006 |

OTHER PUBLICATIONS

Bosi et al., "Vildagliptin plus metformin combination therapy provides superior glycaemic control to individual monotherapy in treatment-naive patients with type 2 diabetes mellitus," Diabetes Obes Metab. 11(5):506-15 (2009).

Chawla et al., "Initial combination therapy with vildagliptin plus metformin in drug-naïve patients with T2DM: a 24-week real-life study from Asia," Curr Med Res Opin. 34(9):1605-11 (2018).

Del Prato et al., "Study to determine the durability of glycaemic control with early treatment with a vildagliptin-metformin combination regimen vs. standard-of-care metformin monotherapy-the VERIFY trial: a randomized double-blind trial," Diabet Med. 31(10):1178-84 (2014).

Derosa et al., "Sitagliptin in type 2 diabetes mellitus: Efficacy after five years of therapy," Pharmacol Res. 100:127-34 (2015).

Eucreas Summary of Product Characteristics, Sep. 2009, pp. 1-20, European Medicines Agency, available <https://www.ema.europa.eu/en/documents/product-information/eucreas-epar-product-information_en.pdf>.

Evans et al., "Factors that may Account for Cardiovascular Risk Reduction with a Dipeptidyl Peptidase-4 Inhibitor, Vildagliptin, in Young Patients with Type 2 Diabetes Mellitus," Diabetes Ther. 9(1):27-36 (2018).

Galvus 50 mg Package Leaflet, Nov. 2016 (17 pages), Novartis Pharma AG Prescribing Information, available <https://www.novartis.com.sg/system/files/product-info/GALVUS%20PI%20Nov2016.SIN_.pdf>.

Griffin et al., "Impact of metformin on cardiovascular disease: a meta-analysis of randomised trials among people with type 2 diabetes," Diabetologia. 60(9):1620-9 (2017).

International Search Report and Written Opinion for International Patent Application No. PCT/EP2020/075993, mailed Dec. 1, 2020 (14 pages).

Ji et al., "Efficacy and safety of combination therapy with vildagliptin and metformin versus metformin uptitration in Chinese patients with type 2 diabetes inadequately controlled with metformin monotherapy: a randomized, open-label, prospective study (VISION)," Diabetes Obes Metab. 18(8):775-82 (2016).

Mathieu et al., "Effectiveness and tolerability of second-line therapy with vildagliptin vs. other oral agents in type 2 diabetes: A real-life worldwide observational study (EDGE)," Int J Clin Pract. 67(10):947-56 (2013).

Matthews et al., "Baseline characteristics in the VERIFY study: a randomized trial assessing the durability of glycaemic control with early vildagliptin-metformin combination in newly diagnosed Type 2 diabetes," Diabetic Med. 36(4):505-13 (2019).

(Continued)

*Primary Examiner* — Kevin E Weddington
(74) *Attorney, Agent, or Firm* — Clark & Elbing LLP; Michael J. Belliveau

(57) ABSTRACT

The invention relates to a DPP-IV inhibitor (preferably vildagliptin or a pharmaceutically acceptable salt thereof), and metformin or a pharmaceutically acceptable salt thereof, for use in treating type 2 diabetes. The invention also relates to the use of a DPP-IV inhibitor (preferably vildagliptin or a pharmaceutically acceptable salt thereof), and metformin or a pharmaceutically acceptable salt thereof, in the manufacture of a medicament for treating type 2 diabetes. The invention also relates to a method of treating type 2 diabetes using a DPP-IV inhibitor (preferably vildagliptin or a pharmaceutically acceptable salt thereof), and metformin or a pharmaceutically acceptable salt thereof.

14 Claims, 4 Drawing Sheets

(56) References Cited

OTHER PUBLICATIONS

Matthews et al., "Glycaemic durability of an early combination therapy with vildagliptin and metformin versus sequential metformin monotherapy in newly diagnosed type 2 diabetes (VERIFY): a 5-year, multicentre, randomised, double-blind trial," Lancet. 394(10208):1519-29 (2019).

Skyler et al., "Intensive glycemic control and the prevention of cardiovascular events: implications of the Accord, Advance, and VA Diabetes Trials: a position statement of the American Diabetes Association and a Scientific Statement of the American College of Cardiology Foundation and the American Heart Association," Diabetes Care. 32(1):187-92 (2009).

UK Prospective Diabetes Study Group, "Effect of intensive blood-glucose control with metformin on complications in overweight patients with type 2 diabetes (UKPDS 34)," Lancet. 352(9131):854-65 (1998).

Ku et al. "Four-Year Durability of Initial Combination Therapy with Sitagliptin and Metformin in Patients with Tyge 2 Diabetes in Clinical Practice; COSMIC Study," PLoS ONE 10(6): 1-14 (2015).

Lim et al. "Efficacy and safety of initial combination therapy with gemigliptin and metformin compared with monotherapy with either drug in patients with type 2 diabetes: A double-blind randomized controlled trial (INICOM study)," Diabetes Obes Metab. 19(1):87-97 (2017).

Ross et al. "Initial combination of linagliptin and metformin compared with linagliptin monotherapy in patients with newly diagnosed type 2 diabetes and marked hyperglycemia: a randomized, double-blind, active-controlled, parallel group, multinational clinical trial," Diabetes, Obesity and Metabolism. 17: 136-144 (2015).

Pratley et al. "Efficacy and safety of initial combination therapy with alogliptin plus metformin versus either as monotherapy in drug-naïve patients with type 2 diabetes: a randomized, double-blind, 6-month study," Diabetes, Obesity and Metabolism. 16: 613-621 (2014).

Pfützner et al. "Initial combination therapy with saxagliptin and metformin provides sustained glycaemic control and is well tolerated for up to 76 weeks," Diabetes, Obesity and Metabolism. 13: 567-576 (2011).

Communication enclosing Extended European Search Report for European Patent Application No. 23206468.3, dated Feb. 8, 2024 (13 pages).

\* cited by examiner

COMBINATION THERAPY

INTRODUCTION

The invention relates to a DPP-IV inhibitor (preferably vildagliptin or a pharmaceutically acceptable salt thereof), and metformin or a pharmaceutically acceptable salt thereof, for use in treating type 2 diabetes. The invention also relates to the use of a DPP-IV inhibitor (preferably vildagliptin or a pharmaceutically acceptable salt thereof), and metformin or a pharmaceutically acceptable salt thereof, in the manufacture of a medicament for treating type 2 diabetes. The invention also relates to a method of treating type 2 diabetes using a DPP-IV inhibitor (preferably vildagliptin or a pharmaceutically acceptable salt thereof), and metformin or a pharmaceutically acceptable salt thereof.

BACKGROUND

Diabetes mellitus is a chronic metabolic disorder characterized by the presence of hyperglycemia (raised blood glucose concentrations). It may be divided into four general subclasses, including i) type 1 or insulin-dependent diabetes mellitus (IDDM) (caused by β-cell destruction and characterized by absolute insulin deficiency), ii) type 2 or non-insulin-dependent diabetes mellitus (NIDDM) (characterized by impaired insulin action and impaired insulin secretion), iii) other specific types of diabetes (associated with various identifiable clinical conditions or syndromes such as genetic defects of beta-cell function e.g. maturity-onset diabetes of the young types 1-3 and point mutations in mitochondrial DNA), and iv) gestational diabetes mellitus.

The prevalence of type 2 diabetes is high and is growing at an alarming rate. The global burden of diabetes mellitus is expected to reach 300 million by the year 2025, with more than 90% of these individuals having type 2 diabetes.

The predominant pathophysiological defects leading to hyperglycemia in type 2 diabetes are impaired insulin action (insulin resistance) and impaired insulin secretion (beta-cell dysfunction). Treating hyperglycemia is therapeutically important in diabetes mellitus in order to prevent symptoms caused by the raised blood glucose concentrations, such as polyuria (excessive urination) and polydipsia (excessive thirst), and to reduce the risk of diabetic complications. The chronic hyperglycemia of diabetes mellitus is associated with significant, often devastating long-term complications in the eyes, kidneys, nerves and blood vessels. In a large study of pharmacotherapy in type 2 diabetes, "The United Kingdom Prospective Diabetes Study" (UKPDS), demonstrated that lowering blood glucose concentrations with pharmacotherapy in type 2 diabetes reduces the risk of complications [Lancet 352:837-853, 1998]. The study showed that there was no lower threshold for the benefits of glucose lowering and that any additional glucose lowering would further reduce the risk of development of diabetic complications. The UKPDS also demonstrated that an inexorable decline in beta-cell function occurs with time in type 2 diabetes [Diabetes 44:1249-1258, 1995]. This leads, in the majority of patients, to worsening of glycaemic control with time, requiring addition of more and more therapies as the disease progresses.

Guidelines for the management of hyperglycemia in type 2 diabetes recommend metformin as first-line pharmacological therapy with sequential intensification and second-line therapy only when glycaemic control (glycated haemoglobin A1c [$HbA_{1c}$]≤53 mmol/mol or ≤7.0%) is not achieved. One such second-line therapy involves administering a combination of metformin and the DPP-IV inhibitor vildagliptin. However, with clinical inertia, treatment intensification is often delayed, resulting in loss of glycaemic control and exposure to avoidable hyperglycemia. The UKPDS established that early treatment to lower glycaemia using metformin monotherapy was associated with reduction in myocardial infarction, diabetes-related deaths, and all-cause mortality, and a legacy of continued benefit after 10 years. Achieving early glycaemic control within the first 12 months of diagnosis is desirable, as this improves long-term glycaemic durability and reduces the risk of associated complications.

There is a desire in the art for new therapies which are able to treat type 2 diabetes. In particular, there is a desire to provide new therapies which are able to provide greater and more durable long-term benefits compared with the current standard-of-care initial metformin monotherapy for patients with newly diagnosed type 2 diabetes.

SUMMARY OF THE INVENTION

The present invention arose as a result of a 5-year efficacy and safety study which compared an early combination therapy of metformin and vildagliptin, with the current standard-of-care (which initially administers metformin monotherapy, with the combination of metformin and vildagliptin being introduced only when the metformin monotherapy fails). The inventors have demonstrated for the first time that early intervention with a combination therapy of metformin and vildagliptin provides greater and more durable long-term benefits compared with the current standard-of-care in patients with type 2 diabetes. The invention provides long-term clinical benefits more frequently and without tolerability issues. In addition, the inventors found that the early intervention with the combination therapy was unexpectedly associated with a reduced risk of cardiovascular events.

Medical Uses

In one aspect, the invention relates to a combination of a DPP-IV inhibitor (preferably vildagliptin or a pharmaceutically acceptable salt thereof), and metformin or a pharmaceutically acceptable salt thereof, for use in a method of delaying loss of glycaemic control in a patient with type 2 diabetes mellitus.

In one aspect, the invention relates to a combination of a vildagliptin or a pharmaceutically acceptable salt thereof and metformin or a pharmaceutically acceptable salt thereof, for use in a method of delaying loss of glycaemic control in a patient with type 2 diabetes mellitus.

In one aspect, the invention relates to a combination of a DPP-IV inhibitor (preferably vildagliptin or a pharmaceutically acceptable salt thereof), and metformin or a pharmaceutically acceptable salt thereof, for use in a method of delaying loss of glycaemic control in a patient with type 2 diabetes mellitus, wherein the patient has not previously received pharmaceutical treatment for the type 2 diabetes mellitus.

In one aspect, the invention relates to a combination of vildagliptin or a pharmaceutically acceptable salt thereof, and metformin or a pharmaceutically acceptable salt thereof, for use in a method of delaying loss of glycaemic control in a patient with type 2 diabetes mellitus, wherein the patient has not previously received pharmaceutical treatment for the type 2 diabetes mellitus.

In one aspect, the invention relates to a combination of a DPP-IV inhibitor (preferably vildagliptin or a pharmaceutically acceptable salt thereof), and metformin or a pharmaceutically acceptable salt thereof, for use in a method of delaying loss of glycaemic control in a patient with type 2 diabetes mellitus, wherein the loss of glycaemic control is delayed relative to metformin monotherapy.

In one aspect, the invention relates to a combination of a DPP-IV inhibitor (preferably vildagliptin or a pharmaceutically acceptable salt thereof), and metformin or a pharmaceutically acceptable salt thereof, for use in a method of delaying loss of glycaemic control in a patient with type 2 diabetes mellitus, wherein the loss of glycaemic control is delayed relative to metformin monotherapy followed by subsequent co-administration of a DPP-IV inhibitor (preferably vildagliptin or a pharmaceutically acceptable salt thereof) and metformin or a pharmaceutically acceptable salt thereof.

In one aspect, the invention relates to a combination of vildagliptin or a pharmaceutically acceptable salt thereof, and metformin or a pharmaceutically acceptable salt thereof, for use in a method of delaying loss of glycaemic control in a patient with type 2 diabetes mellitus, wherein the loss of glycaemic control is delayed relative to metformin monotherapy.

In one aspect, the invention relates to a combination of vildagliptin or a pharmaceutically acceptable salt thereof, and metformin or a pharmaceutically acceptable salt thereof, for use in a method of delaying loss of glycaemic control in a patient with type 2 diabetes mellitus, wherein the loss of glycaemic control is delayed relative to metformin monotherapy followed by subsequent co-administration of a DPP-IV inhibitor (preferably vildagliptin or a pharmaceutically acceptable salt thereof) and metformin or a pharmaceutically acceptable salt thereof.

In one aspect, the invention relates to a combination of a DPP-IV inhibitor (preferably vildagliptin or a pharmaceutically acceptable salt thereof), and metformin or a pharmaceutically acceptable salt thereof, for use in a method of delaying loss of glycaemic control in a patient with type 2 diabetes mellitus, wherein the loss of glycaemic control is delayed relative to metformin monotherapy, and wherein the patient has not previously received pharmaceutical treatment for the type 2 diabetes mellitus.

In one aspect, the invention relates to a combination of a DPP-IV inhibitor (preferably vildagliptin or a pharmaceutically acceptable salt thereof), and metformin or a pharmaceutically acceptable salt thereof, for use in a method of delaying loss of glycaemic control in a patient with type 2 diabetes mellitus, wherein the loss of glycaemic control is delayed relative to metformin monotherapy followed by subsequent co-administration of a DPP-IV inhibitor (preferably vildagliptin or a pharmaceutically acceptable salt thereof) and metformin or a pharmaceutically acceptable salt thereof, and wherein the patient has not previously received pharmaceutical treatment for the type 2 diabetes mellitus.

In one aspect, the invention relates to a combination of vildagliptin or a pharmaceutically acceptable salt thereof, and metformin or a pharmaceutically acceptable salt thereof, for use in a method of delaying loss of glycaemic control in a patient with type 2 diabetes mellitus, wherein the loss of glycaemic control is delayed relative to metformin monotherapy, and wherein the patient has not previously received pharmaceutical treatment for the type 2 diabetes mellitus.

In one aspect, the invention relates to a combination of vildagliptin or a pharmaceutically acceptable salt thereof, and metformin or a pharmaceutically acceptable salt thereof, for use in a method of delaying loss of glycaemic control in a patient with type 2 diabetes mellitus, wherein the loss of glycaemic control is delayed relative to metformin monotherapy followed by subsequent co-administration of a DPP-IV inhibitor (preferably vildagliptin or a pharmaceutically acceptable salt thereof) and metformin or a pharmaceutically acceptable salt thereof, and wherein the patient has not previously received pharmaceutical treatment for the type 2 diabetes mellitus.

In another aspect, the invention relates to a combination of a DPP-IV inhibitor (preferably vildagliptin or a pharmaceutically acceptable salt thereof), and metformin or a pharmaceutically acceptable salt thereof, for use in a method of improving glycaemic control in a patient with type 2 diabetes mellitus.

In another aspect, the invention relates to a combination of a DPP-IV inhibitor (preferably vildagliptin or a pharmaceutically acceptable salt thereof), and metformin or a pharmaceutically acceptable salt thereof, for use in a method of improving glycaemic control in a patient with type 2 diabetes mellitus, wherein the improvement in glycaemic control is relative to metformin monotherapy.

In another aspect, the invention relates to a combination of a DPP-IV inhibitor (preferably vildagliptin or a pharmaceutically acceptable salt thereof), and metformin or a pharmaceutically acceptable salt thereof, for use in a method of improving glycaemic control in a patient with type 2 diabetes mellitus, wherein the improvement in glycaemic control is relative to metformin monotherapy followed by subsequent co-administration of a DPP-IV inhibitor (preferably vildagliptin or a pharmaceutically acceptable salt thereof) and metformin or a pharmaceutically acceptable salt thereof.

In another aspect, the invention relates to a combination of vildagliptin or a pharmaceutically acceptable salt thereof, and metformin or a pharmaceutically acceptable salt thereof, for use in a method of improving glycaemic control in a patient with type 2 diabetes mellitus, wherein the improvement in glycaemic control is relative to metformin monotherapy.

In another aspect, the invention relates to a combination of vildagliptin or a pharmaceutically acceptable salt thereof, and metformin or a pharmaceutically acceptable salt thereof, for use in a method of improving glycaemic control in a patient with type 2 diabetes mellitus, wherein the improvement in glycaemic control is relative to metformin monotherapy followed by subsequent co-administration of a DPP-IV inhibitor (preferably vildagliptin or a pharmaceutically acceptable salt thereof) and metformin or a pharmaceutically acceptable salt thereof.

In another aspect, the invention relates to a combination of a DPP-IV inhibitor (preferably vildagliptin or a pharmaceutically acceptable salt thereof), and metformin or a pharmaceutically acceptable salt thereof, for use in a method of improving glycaemic control in a patient with type 2 diabetes mellitus, wherein the improvement in glycaemic control is relative to metformin monotherapy, and wherein the patient has not previously received pharmaceutical treatment for the type 2 diabetes mellitus.

In another aspect, the invention relates to a combination of a DPP-IV inhibitor (preferably vildagliptin or a pharmaceutically acceptable salt thereof), and metformin or a pharmaceutically acceptable salt thereof, for use in a method of improving glycaemic control in a patient with type 2 diabetes mellitus, wherein the improvement in glycaemic control is relative to metformin monotherapy followed by subsequent co-administration of a DPP-IV inhibitor (preferably vildagliptin or a pharmaceutically acceptable salt thereof) and metformin or a pharmaceutically acceptable salt thereof, and wherein the patient has not previously received pharmaceutical treatment for the type 2 diabetes mellitus.

In another aspect, the invention relates to a combination of vildagliptin or a pharmaceutically acceptable salt thereof, and metformin or a pharmaceutically acceptable salt thereof, for use in a method of improving glycaemic control in a patient with type 2 diabetes mellitus, wherein the improvement in glycaemic control is relative to metformin monotherapy, and wherein the patient has not previously received pharmaceutical treatment for the type 2 diabetes mellitus.

In another aspect, the invention relates to a combination of vildagliptin or a pharmaceutically acceptable salt thereof, and metformin or a pharmaceutically acceptable salt thereof, for use in a method of improving glycaemic control in a patient with type 2 diabetes mellitus, wherein the improvement in glycaemic control is relative to metformin monotherapy followed by subsequent co-administration of a DPP-IV inhibitor (preferably vildagliptin or a pharmaceutically acceptable salt thereof) and metformin or a pharmaceutically acceptable salt thereof, and wherein the patient has not previously received pharmaceutical treatment for the type 2 diabetes mellitus.

In another aspect, the invention relates to a combination of a DPP-IV inhibitor (preferably vildagliptin or a pharmaceutically acceptable salt thereof), and metformin or a pharmaceutically acceptable salt thereof, for use in a method of improving glycaemic control in a patient with type 2 diabetes mellitus, wherein the patient has not previously received pharmaceutical treatment for the type 2 diabetes mellitus.

In another aspect, the invention relates to a combination of vildagliptin or a pharmaceutically acceptable salt thereof, and metformin or a pharmaceutically acceptable salt thereof, for use in a method of improving glycaemic control in a patient with type 2 diabetes mellitus, wherein the patient has not previously received pharmaceutical treatment for the type 2 diabetes mellitus.

In another aspect, the invention relates to a combination of a DPP-IV inhibitor (preferably vildagliptin or a pharmaceutically acceptable salt thereof), and metformin or a pharmaceutically acceptable salt thereof, for use in a method of delaying the increase of $HbA_{1c}$ to greater than or equal to 53 mmol/mol (7.0%) in a patient with type 2 diabetes mellitus.

In another aspect, the invention relates to a combination of a DPP-IV inhibitor (preferably vildagliptin or a pharmaceutically acceptable salt thereof), and metformin or a pharmaceutically acceptable salt thereof, for use in a method of delaying the increase of $HbA_{1c}$ to greater than or equal to 53 mmol/mol (7.0%) in a patient with type 2 diabetes mellitus, wherein the delay in the increase of $HbA_{1c}$ is relative to metformin monotherapy.

In another aspect, the invention relates to a combination of a DPP-IV inhibitor (preferably vildagliptin or a pharmaceutically acceptable salt thereof), and metformin or a pharmaceutically acceptable salt thereof, for use in a method of delaying the increase of $HbA_{1c}$ to greater than or equal to 53 mmol/mol (7.0%) in a patient with type 2 diabetes mellitus, wherein the delay in the increase of $HbA_{1c}$ is relative to metformin monotherapy followed by subsequent co-administration of a DPP-IV inhibitor (preferably vildagliptin or a pharmaceutically acceptable salt thereof) and metformin.

In another aspect, the invention relates to a combination of vildagliptin or a pharmaceutically acceptable salt thereof, and metformin or a pharmaceutically acceptable salt thereof, for use in a method of delaying the increase of $HbA_{1c}$ to greater than or equal to 53 mmol/mol (7.0%) in a patient with type 2 diabetes mellitus, wherein the delay in the increase of $HbA_{1c}$ is relative to metformin monotherapy.

In another aspect, the invention relates to a combination of vildagliptin or a pharmaceutically acceptable salt thereof, and metformin or a pharmaceutically acceptable salt thereof, for use in a method of delaying the increase of $HbA_{1c}$ to greater than or equal to 53 mmol/mol (7.0%) in a patient with type 2 diabetes mellitus, wherein the delay in the increase of $HbA_{1c}$ is relative to metformin monotherapy followed by subsequent co-administration of a DPP-IV inhibitor (preferably vildagliptin or a pharmaceutically acceptable salt thereof) and metformin or a pharmaceutically acceptable salt thereof.

In another aspect, the invention relates to a combination of a DPP-IV inhibitor (preferably vildagliptin or a pharmaceutically acceptable salt thereof), and metformin or a pharmaceutically acceptable salt thereof, for use in a method of delaying the increase of $HbA_{1c}$ to greater than or equal to 53 mmol/mol (7.0%) in a patient with type 2 diabetes mellitus, wherein the delay in the increase of $HbA_{1c}$ is relative to metformin monotherapy, and wherein the patient has not previously received pharmaceutical treatment for the type 2 diabetes mellitus.

In another aspect, the invention relates to a combination of a DPP-IV inhibitor (preferably vildagliptin or a pharmaceutically acceptable salt thereof), and metformin or a pharmaceutically acceptable salt thereof, for use in a method of delaying the increase of $HbA_{1c}$ to greater than or equal to 53 mmol/mol (7.0%) in a patient with type 2 diabetes mellitus, wherein the delay in the increase of $HbA_{1c}$ is relative to metformin monotherapy followed by subsequent co-administration of a DPP-IV inhibitor (preferably vildagliptin or a pharmaceutically acceptable salt thereof) and metformin or a pharmaceutically acceptable salt thereof, and wherein the patient has not previously received pharmaceutical treatment for the type 2 diabetes mellitus.

In another aspect, the invention relates to a combination of vildagliptin or a pharmaceutically acceptable salt thereof, and metformin or a pharmaceutically acceptable salt thereof, for use in a method of delaying the increase of $HbA_{1c}$ to greater than or equal to 53 mmol/mol (7.0%) in a patient with type 2 diabetes mellitus, wherein the delay in the increase of $HbA_{1c}$ is relative to metformin monotherapy, and wherein the patient has not previously received pharmaceutical treatment for the type 2 diabetes mellitus.

In another aspect, the invention relates to a combination of vildagliptin or a pharmaceutically acceptable salt thereof, and metformin or a pharmaceutically acceptable salt thereof, for use in a method of delaying the increase of $HbA_{1c}$ to greater than or equal to 53 mmol/mol (7.0%) in a patient with type 2 diabetes mellitus, wherein the delay in the increase of $HbA_{1c}$ is relative to metformin monotherapy followed by subsequent co-administration of a DPP-IV inhibitor (preferably vildagliptin or a pharmaceutically acceptable salt thereof) and metformin or a pharmaceutically acceptable salt thereof, and wherein the patient has not previously received pharmaceutical treatment for the type 2 diabetes mellitus.

In another aspect, the invention relates to a combination of a DPP-IV inhibitor (preferably vildagliptin or a pharmaceutically acceptable salt thereof), and metformin or a pharmaceutically acceptable salt thereof, for use in a method of delaying the increase of $HbA_{1c}$ to greater than or equal to 53 mmol/mol (7.0%) in a patient with type 2 diabetes mellitus, wherein the patient has not previously received pharmaceutical treatment for the type 2 diabetes mellitus.

In another aspect, the invention relates to a combination of vildagliptin or a pharmaceutically acceptable salt thereof, and metformin or a pharmaceutically acceptable salt thereof, for use in a method of delaying the increase of $HbA_{1c}$ to greater than or equal to 53 mmol/mol (7.0%) in a patient with type 2 diabetes mellitus, wherein the patient has not previously received pharmaceutical treatment for the type 2 diabetes mellitus.

In another aspect, the invention relates to a combination of a DPP-IV inhibitor (preferably vildagliptin or a pharmaceutically acceptable salt thereof), and metformin or a pharmaceutically acceptable salt thereof, for use in a method of increasing the time taken to reach an $HbA_{1c}$ measurement of greater than or equal to 53 mmol/mol (7.0%) in a patient with type 2 diabetes mellitus.

In another aspect, the invention relates to a combination of a DPP-IV inhibitor (preferably vildagliptin or a pharmaceutically acceptable salt thereof), and metformin or a pharmaceutically acceptable salt thereof, for use in a method of increasing the time taken to reach an $HbA_{1c}$ measurement of greater than or equal to 53 mmol/mol (7.0%) in a patient with type 2 diabetes mellitus, wherein the increase is relative to metformin monotherapy.

In another aspect, the invention relates to a combination of a DPP-IV inhibitor (preferably vildagliptin or a pharmaceutically acceptable salt thereof), and metformin or a pharmaceutically acceptable salt thereof, for use in a method of increasing the time taken to reach an $HbA_{1c}$ measurement of greater than or equal to 53 mmol/mol (7.0%) in a patient with type 2 diabetes mellitus, wherein the increase is relative to metformin monotherapy followed by subsequent co-administration of a DPP-IV inhibitor (preferably vildagliptin or a pharmaceutically acceptable salt thereof) and metformin or a pharmaceutically acceptable salt thereof.

In another aspect, the invention relates to a combination of vildagliptin or a pharmaceutically acceptable salt thereof, and metformin or a pharmaceutically acceptable salt thereof, for use in a method of increasing the time taken to reach an $HbA_{1c}$ measurement of greater than or equal to 53 mmol/mol (7.0%) in a patient with type 2 diabetes mellitus, wherein the increase is relative to metformin monotherapy.

In another aspect, the invention relates to a combination of vildagliptin or a pharmaceutically acceptable salt thereof, and metformin or a pharmaceutically acceptable salt thereof, for use in a method of increasing the time taken to reach an $HbA_{1c}$ measurement of greater than or equal to 53 mmol/mol (7.0%) in a patient with type 2 diabetes mellitus, wherein the increase is relative to metformin monotherapy followed by subsequent co-administration of a DPP-IV inhibitor (preferably vildagliptin or a pharmaceutically acceptable salt thereof) and metformin or a pharmaceutically acceptable salt thereof.

In another aspect, the invention relates to a combination of a DPP-IV inhibitor (preferably vildagliptin or a pharmaceutically acceptable salt thereof), and metformin or a pharmaceutically acceptable salt thereof, for use in a method of increasing the time taken to reach an $HbA_{1c}$ measurement of greater than or equal to 53 mmol/mol (7.0%) in a patient with type 2 diabetes mellitus, wherein the increase is relative to metformin monotherapy, and wherein the patient has not previously received pharmaceutical treatment for the type 2 diabetes mellitus.

In another aspect, the invention relates to a combination of a DPP-IV inhibitor (preferably vildagliptin or a pharmaceutically acceptable salt thereof), and metformin or a pharmaceutically acceptable salt thereof, for use in a method of increasing the time taken to reach an $HbA_{1c}$ measurement of greater than or equal to 53 mmol/mol (7.0%) in a patient with type 2 diabetes mellitus, wherein the increase is relative to metformin monotherapy followed by subsequent co-administration of a DPP-IV inhibitor (preferably vildagliptin or a pharmaceutically acceptable salt thereof) and metformin or a pharmaceutically acceptable salt thereof, and wherein the patient has not previously received pharmaceutical treatment for the type 2 diabetes mellitus.

In another aspect, the invention relates to a combination of vildagliptin or a pharmaceutically acceptable salt thereof, and metformin or a pharmaceutically acceptable salt thereof, for use in a method of increasing the time taken to reach an $HbA_{1c}$ measurement of greater than or equal to 53 mmol/mol (7.0%) in a patient with type 2 diabetes mellitus, wherein the increase is relative to metformin monotherapy, and wherein the patient has not previously received pharmaceutical treatment for the type 2 diabetes mellitus.

In another aspect, the invention relates to a combination of vildagliptin or a pharmaceutically acceptable salt thereof, and metformin or a pharmaceutically acceptable salt thereof, for use in a method of increasing the time taken to reach an $HbA_{1c}$ measurement of greater than or equal to 53 mmol/mol (7.0%) in a patient with type 2 diabetes mellitus, wherein the increase is relative to metformin monotherapy followed by subsequent co-administration of a DPP-IV inhibitor (preferably vildagliptin or a pharmaceutically acceptable salt thereof) and metformin or a pharmaceutically acceptable salt thereof, and wherein the patient has not previously received pharmaceutical treatment for the type 2 diabetes mellitus.

In another aspect, the invention relates to a combination of a DPP-IV inhibitor (preferably vildagliptin or a pharmaceutically acceptable salt thereof), and metformin or a pharmaceutically acceptable salt thereof, for use in a method of increasing the time taken to reach an $HbA_{1c}$ measurement of greater than or equal to 53 mmol/mol (7.0%) in a patient with type 2 diabetes mellitus, wherein the patient has not previously received pharmaceutical treatment for the type 2 diabetes mellitus.

In another aspect, the invention relates to a combination of vildagliptin or a pharmaceutically acceptable salt thereof, and metformin or a pharmaceutically acceptable salt thereof, for use in a method of increasing the time taken to reach an $HbA_{1c}$ measurement of greater than or equal to 53 mmol/mol (7.0%) in a patient with type 2 diabetes mellitus, wherein the patient has not previously received pharmaceutical treatment for the type 2 diabetes mellitus.

In another aspect, the invention relates to a combination of a DPP-IV inhibitor (preferably vildagliptin or a pharmaceutically acceptable salt thereof), and metformin or a pharmaceutically acceptable salt thereof, for use in a method of preventing loss of glycaemic control in a patient with type 2 diabetes mellitus.

In another aspect, the invention relates to a combination of vildagliptin or a pharmaceutically acceptable salt thereof, and metformin or a pharmaceutically acceptable salt thereof, for use in a method of preventing loss of glycaemic control in a patient with type 2 diabetes mellitus.

In another aspect, the invention relates to a combination of a DPP-IV inhibitor (preferably vildagliptin or a pharmaceutically acceptable salt thereof), and metformin or a pharmaceutically acceptable salt thereof, for use in a method of preventing loss of glycaemic control in a patient with type 2 diabetes mellitus, wherein the patient has not previously received pharmaceutical treatment for the type 2 diabetes mellitus.

In another aspect, the invention relates to a combination of vildagliptin or a pharmaceutically acceptable salt thereof, and metformin or a pharmaceutically acceptable salt thereof, for use in a method of preventing loss of glycaemic control in a patient with type 2 diabetes mellitus, wherein the patient has not previously received pharmaceutical treatment for the type 2 diabetes mellitus.

In another aspect, the invention relates to a combination of a DPP-IV inhibitor (preferably vildagliptin or a pharmaceutically acceptable salt thereof), and metformin or a pharmaceutically acceptable salt thereof, for use in a method of reducing the risk of a cardiovascular event in a patient undergoing treatment for type 2 diabetes mellitus.

In another aspect, the invention relates to a combination of vildagliptin or a pharmaceutically acceptable salt thereof, and metformin or a pharmaceutically acceptable salt thereof, for use in a method of reducing the risk of a cardiovascular event in a patient undergoing treatment for type 2 diabetes mellitus.

In another aspect, the invention relates to a combination of a DPP-IV inhibitor (preferably vildagliptin or a pharmaceutically acceptable salt thereof), and metformin or a pharmaceutically acceptable salt thereof, for use in a method of reducing the risk of a cardiovascular event in a patient undergoing treatment for type 2 diabetes mellitus, wherein the patient has not previously received pharmaceutical treatment for the type 2 diabetes mellitus.

In another aspect, the invention relates to a combination of vildagliptin or a pharmaceutically acceptable salt thereof and metformin or a pharmaceutically acceptable salt thereof, for use in a method of reducing the risk of a cardiovascular event in a patient undergoing treatment for type 2 diabetes mellitus, wherein the patient has not previously received pharmaceutical treatment for the type 2 diabetes mellitus.

In another aspect, the invention relates to a combination of a DPP-IV inhibitor (vildagliptin or a pharmaceutically acceptable salt thereof), and metformin or a pharmaceutically acceptable salt thereof, for use in a method of reducing the risk of a cardiovascular event in a patient undergoing treatment for type 2 diabetes mellitus, wherein the risk is reduced relative to metformin monotherapy.

In another aspect, the invention relates to a combination of a DPP-IV inhibitor (preferably vildagliptin or a pharmaceutically acceptable salt thereof), and metformin or a pharmaceutically acceptable salt thereof, for use in a method of reducing the risk of a cardiovascular event in a patient undergoing treatment for type 2 diabetes mellitus, wherein the risk is reduced relative to metformin monotherapy followed by subsequent co-administration of a DPP-IV inhibitor (preferably vildagliptin or a pharmaceutically acceptable salt thereof) and metformin or a pharmaceutically acceptable salt thereof.

In another aspect, the invention relates to a combination of vildagliptin or a pharmaceutically acceptable salt thereof, and metformin or a pharmaceutically acceptable salt thereof, for use in a method of reducing the risk of a cardiovascular event in a patient undergoing treatment for type 2 diabetes mellitus, wherein the risk is reduced relative to metformin monotherapy.

In another aspect, the invention relates to a combination of vildagliptin or a pharmaceutically acceptable salt thereof, and metformin or a pharmaceutically acceptable salt thereof, for use in a method of reducing the risk of a cardiovascular event in a patient undergoing treatment for type 2 diabetes mellitus, wherein the risk is reduced relative to metformin monotherapy followed by subsequent co-administration of a DPP-IV inhibitor (preferably vildagliptin or a pharmaceutically acceptable salt thereof) and metformin or a pharmaceutically acceptable salt thereof.

In another aspect, the invention relates to a combination of a DPP-IV inhibitor (vildagliptin or a pharmaceutically acceptable salt thereof), and metformin or a pharmaceutically acceptable salt thereof, for use in a method of reducing the risk of a cardiovascular event in a patient undergoing treatment for type 2 diabetes mellitus, wherein the risk is reduced relative to metformin monotherapy, and wherein the patient has not previously received pharmaceutical treatment for the type 2 diabetes mellitus.

In another aspect, the invention relates to a combination of a DPP-IV inhibitor (preferably vildagliptin or a pharmaceutically acceptable salt thereof), and metformin or a pharmaceutically acceptable salt thereof, for use in a method of reducing the risk of a cardiovascular event in a patient undergoing treatment for type 2 diabetes mellitus, wherein the risk is reduced relative to metformin monotherapy followed by subsequent co-administration of a DPP-IV inhibitor (preferably vildagliptin or a pharmaceutically acceptable salt thereof) and metformin or a pharmaceutically acceptable salt thereof, and wherein the patient has not previously received pharmaceutical treatment for the type 2 diabetes mellitus.

In another aspect, the invention relates to a combination of vildagliptin or a pharmaceutically acceptable salt thereof, and metformin or a pharmaceutically acceptable salt thereof, for use in a method of reducing the risk of a cardiovascular event in a patient undergoing treatment for type 2 diabetes mellitus, wherein the risk is reduced relative to metformin monotherapy, and wherein the patient has not previously received pharmaceutical treatment for the type 2 diabetes mellitus.

In another aspect, the invention relates to a combination of vildagliptin or a pharmaceutically acceptable salt thereof, and metformin or a pharmaceutically acceptable salt thereof, for use in a method of reducing the risk of a cardiovascular event in a patient undergoing treatment for type 2 diabetes mellitus, wherein the risk is reduced relative to metformin monotherapy followed by subsequent co-administration of a DPP-IV inhibitor (preferably vildagliptin or a pharmaceutically acceptable salt thereof) and metformin or a pharmaceutically acceptable salt thereof, wherein the patient has not previously received pharmaceutical treatment for the type 2 diabetes mellitus.

In another aspect, the invention relates to a combination of a DPP-IV inhibitor (preferably vildagliptin or a pharmaceutically acceptable salt thereof), and metformin or a pharmaceutically acceptable salt thereof, for use in a method of treating type 2 diabetes mellitus without concomitant administration of insulin.

In another aspect, the invention relates to a combination of vildagliptin or a pharmaceutically acceptable salt thereof, and metformin or a pharmaceutically acceptable salt thereof, for use in a method of treating type 2 diabetes mellitus without concomitant administration of insulin.

In another aspect, the invention relates to a combination of a DPP-IV inhibitor (preferably vildagliptin or a pharmaceutically acceptable salt thereof), and metformin or a pharmaceutically acceptable salt thereof, for use in a method of treating type 2 diabetes mellitus without concomitant administration of insulin, wherein the patient has not previously received pharmaceutical treatment for the type 2 diabetes mellitus.

In another aspect, the invention relates to a combination of vildagliptin or a pharmaceutically acceptable salt thereof, and metformin or a pharmaceutically acceptable salt thereof, for use in a method of treating type 2 diabetes mellitus without concomitant administration of insulin, wherein the patient has not previously received pharmaceutical treatment for the type 2 diabetes mellitus.

In one aspect, the invention relates to a DPP-IV inhibitor (preferably vildagliptin or a pharmaceutically acceptable salt thereof), for use in a method of delaying loss of glycaemic control in a patient with type 2 diabetes mellitus, wherein the DPP-IV inhibitor (preferably vildagliptin or a pharmaceutically acceptable salt thereof) is co-administered with metformin or a pharmaceutically acceptable salt thereof.

In one aspect, the invention relates to a DPP-IV inhibitor (preferably vildagliptin or a pharmaceutically acceptable salt thereof), for use in a method of delaying loss of glycaemic control in a patient with type 2 diabetes mellitus, wherein the patient has not previously received pharmaceutical treatment for the type 2 diabetes mellitus, and wherein the DPP-IV inhibitor (preferably vildagliptin or a pharmaceutically acceptable salt thereof) is co-administered with metformin or a pharmaceutically acceptable salt thereof.

In one aspect, the invention relates to vildagliptin or a pharmaceutically acceptable salt thereof, for use in a method of delaying loss of glycaemic control in a patient with type 2 diabetes mellitus, wherein the patient has not previously received pharmaceutical treatment for the type 2 diabetes mellitus, and wherein the vildagliptin or a pharmaceutically acceptable salt thereof, is co-administered with metformin or a pharmaceutically acceptable salt thereof.

In one aspect, the invention relates to a DPP-IV inhibitor (preferably vildagliptin or a pharmaceutically acceptable salt thereof), for use in a method of delaying loss of glycaemic control in a patient with type 2 diabetes mellitus, wherein the delay is relative to metformin monotherapy, and wherein the DPP-IV inhibitor (preferably vildagliptin or a pharmaceutically acceptable salt thereof) is co-administered with metformin or a pharmaceutically acceptable salt thereof.

In one aspect, the invention relates to vildagliptin or a pharmaceutically acceptable salt thereof, for use in a method of delaying loss of glycaemic control in a patient with type 2 diabetes mellitus, wherein the delay is relative to metformin monotherapy, and wherein the vildagliptin or a pharmaceutically acceptable salt thereof, is co-administered with metformin or a pharmaceutically acceptable salt thereof.

In one aspect, the invention relates to a DPP-IV inhibitor (preferably vildagliptin or a pharmaceutically acceptable salt thereof), for use in a method of delaying loss of glycaemic control in a patient with type 2 diabetes mellitus, wherein the delay is relative to metformin monotherapy followed by subsequent co-administration of a DPP-IV inhibitor (preferably vildagliptin or a pharmaceutically acceptable salt thereof) and metformin or a pharmaceutically acceptable salt thereof, and wherein the DPP-IV inhibitor (preferably vildagliptin or a pharmaceutically acceptable salt thereof) is co-administered with metformin or a pharmaceutically acceptable salt thereof.

In one aspect, the invention relates to vildagliptin or a pharmaceutically acceptable salt thereof, for use in a method of delaying loss of glycaemic control in a patient with type 2 diabetes mellitus, wherein the delay is relative to metformin monotherapy followed by subsequent co-administration of a DPP-IV inhibitor (preferably vildagliptin or a pharmaceutically acceptable salt thereof) and metformin, or a pharmaceutically acceptable salt thereof, wherein the vildagliptin or a pharmaceutically acceptable salt thereof, is co-administered with metformin or a pharmaceutically acceptable salt thereof.

In one aspect, the invention relates to a DPP-IV inhibitor (preferably vildagliptin or a pharmaceutically acceptable salt thereof), for use in a method of delaying loss of glycaemic control in a patient with type 2 diabetes mellitus, wherein the delay is relative to metformin monotherapy, and wherein the DPP-IV inhibitor (preferably vildagliptin or a pharmaceutically acceptable salt thereof) is co-administered with metformin or a pharmaceutically acceptable salt thereof, and wherein the patient has not previously received pharmaceutical treatment for the type 2 diabetes mellitus.

In one aspect, the invention relates to vildagliptin or a pharmaceutically acceptable salt thereof, for use in a method of delaying loss of glycaemic control in a patient with type 2 diabetes mellitus, wherein the delay is relative to metformin monotherapy, and wherein the vildagliptin or a pharmaceutically acceptable salt thereof, is co-administered with metformin or a pharmaceutically acceptable salt thereof, and wherein the patient has not previously received pharmaceutical treatment for the type 2 diabetes mellitus.

In one aspect, the invention relates to a DPP-IV inhibitor (preferably vildagliptin or a pharmaceutically acceptable salt thereof), for use in a method of delaying loss of glycaemic control in a patient with type 2 diabetes mellitus, wherein the delay is relative to metformin monotherapy followed by subsequent co-administration of a DPP-IV inhibitor (preferably vildagliptin or a pharmaceutically acceptable salt thereof) and metformin or a pharmaceutically acceptable salt thereof, and wherein the DPP-IV inhibitor (preferably vildagliptin or a pharmaceutically acceptable salt thereof) is co-administered with metformin or a pharmaceutically acceptable salt thereof, wherein the patient has not previously received pharmaceutical treatment for the type 2 diabetes mellitus.

In one aspect, the invention relates to vildagliptin or a pharmaceutically acceptable salt thereof, for use in a method of delaying loss of glycaemic control in a patient with type 2 diabetes mellitus, wherein the delay is relative to metformin monotherapy followed by subsequent co-administration of a DPP-IV inhibitor (preferably vildagliptin or a pharmaceutically acceptable salt thereof) and metformin or a pharmaceutically acceptable salt thereof, and wherein the vildagliptin or a pharmaceutically acceptable salt thereof, is co-administered with metformin or a pharmaceutically acceptable salt thereof, wherein the patient has not previously received pharmaceutical treatment for the type 2 diabetes mellitus.

In another aspect, the invention relates to a DPP-IV inhibitor (preferably vildagliptin or a pharmaceutically acceptable salt thereof), for use in a method of improving glycaemic control in a patient with type 2 diabetes mellitus, wherein the DPP-IV inhibitor (preferably vildagliptin or a pharmaceutically acceptable salt thereof) is co-administered with metformin or a pharmaceutically acceptable salt thereof.

In another aspect, the invention relates to a DPP-IV inhibitor (preferably vildagliptin or a pharmaceutically acceptable salt thereof), for use in a method of improving glycaemic control in a patient with type 2 diabetes mellitus, wherein the improvement in glycaemic control is relative to metformin monotherapy, and wherein the DPP-IV inhibitor (preferably vildagliptin or a pharmaceutically acceptable salt thereof) is co-administered with metformin or a pharmaceutically acceptable salt thereof, or a pharmaceutically acceptable salt thereof.

In another aspect, the invention relates to vildagliptin or a pharmaceutically acceptable salt thereof, for use in a method of improving glycaemic control in a patient with type 2 diabetes mellitus, wherein the improvement in glycaemic control is relative to metformin monotherapy, and wherein the vildagliptin or a pharmaceutically acceptable salt thereof, is co-administered with metformin or a pharmaceutically acceptable salt thereof.

In another aspect, the invention relates to a DPP-IV inhibitor (preferably vildagliptin or a pharmaceutically acceptable salt thereof), for use in a method of improving glycaemic control in a patient with type 2 diabetes mellitus, wherein the improvement in glycaemic control is relative to metformin monotherapy followed by subsequent co-administration of a DPP-IV inhibitor (preferably vildagliptin or a pharmaceutically acceptable salt thereof) and metformin or a pharmaceutically acceptable salt thereof, and wherein the DPP-IV inhibitor (preferably vildagliptin or a pharmaceutically acceptable salt thereof) is co-administered with metformin or a pharmaceutically acceptable salt thereof.

In another aspect, the invention relates to vildagliptin or a pharmaceutically acceptable salt thereof, for use in a method of improving glycaemic control in a patient with type 2 diabetes mellitus, wherein the improvement in glycaemic control is relative to metformin monotherapy followed by subsequent co-administration of a DPP-IV inhibitor (preferably vildagliptin or a pharmaceutically acceptable salt thereof) and metformin or a pharmaceutically acceptable salt thereof, and wherein the DPP-IV inhibitor (preferably vildagliptin or a pharmaceutically acceptable salt thereof) is co-administered with metformin or a pharmaceutically acceptable salt thereof.

In another aspect, the invention relates to a DPP-IV inhibitor (preferably vildagliptin or a pharmaceutically acceptable salt thereof), for use in a method of improving glycaemic control in a patient with type 2 diabetes mellitus, wherein the improvement in glycaemic control is relative to metformin monotherapy, and wherein the DPP-IV inhibitor (preferably vildagliptin or a pharmaceutically acceptable salt thereof) is co-administered with metformin or a pharmaceutically acceptable salt thereof, and wherein the patient has not previously received pharmaceutical treatment for the type 2 diabetes mellitus.

In another aspect, the invention relates to vildagliptin or a pharmaceutically acceptable salt thereof, for use in a method of improving glycaemic control in a patient with type 2 diabetes mellitus, wherein the improvement in glycaemic control is relative to metformin monotherapy, and wherein the vildagliptin or a pharmaceutically acceptable salt thereof is co-administered with metformin or a pharmaceutically acceptable salt thereof, and wherein the patient has not previously received pharmaceutical treatment for the type 2 diabetes mellitus.

In another aspect, the invention relates to a DPP-IV inhibitor (preferably vildagliptin or a pharmaceutically acceptable salt thereof), for use in a method of improving glycaemic control in a patient with type 2 diabetes mellitus, wherein the improvement in glycaemic control is relative to metformin monotherapy followed by subsequent co-administration of a DPP-IV inhibitor (preferably vildagliptin or a pharmaceutically acceptable salt thereof) and metformin or a pharmaceutically acceptable salt thereof, and wherein the DPP-IV inhibitor (preferably vildagliptin or a pharmaceutically acceptable salt thereof) is co-administered with metformin or a pharmaceutically acceptable salt thereof, and wherein the patient has not previously received pharmaceutical treatment for the type 2 diabetes mellitus.

In another aspect, the invention relates to vildagliptin or a pharmaceutically acceptable salt thereof, for use in a method of improving glycaemic control in a patient with type 2 diabetes mellitus, wherein the improvement in glycaemic control is relative to metformin monotherapy followed by subsequent co-administration of a DPP-IV inhibitor (preferably vildagliptin or a pharmaceutically acceptable salt thereof) and metformin or a pharmaceutically acceptable salt thereof, and wherein the vildagliptin or a pharmaceutically acceptable salt thereof is co-administered with metformin or a pharmaceutically acceptable salt thereof, and wherein the patient has not previously received pharmaceutical treatment for the type 2 diabetes mellitus.

In another aspect, the invention relates to a DPP-IV inhibitor (preferably vildagliptin or a pharmaceutically acceptable salt thereof), for use in a method of improving glycaemic control in a patient with type 2 diabetes mellitus, wherein the patient has not previously received pharmaceutical treatment for the type 2 diabetes mellitus, and wherein the DPP-IV inhibitor (preferably vildagliptin or a pharmaceutically acceptable salt thereof) is co-administered with metformin or a pharmaceutically acceptable salt thereof.

In another aspect, the invention relates to vildagliptin or a pharmaceutically acceptable salt thereof, for use in a method of improving glycaemic control in a patient with type 2 diabetes mellitus, wherein the patient has not previously received pharmaceutical treatment for the type 2 diabetes mellitus, and wherein the vildagliptin or a pharmaceutically acceptable salt thereof is co-administered with metformin or a pharmaceutically acceptable salt thereof.

In another aspect, the invention relates to a DPP-IV inhibitor (preferably vildagliptin or a pharmaceutically acceptable salt thereof), for use in a method of delaying the increase of $HbA_{1c}$ to greater than or equal to 53 mmol/mol (7.0%) in a patient with type 2 diabetes mellitus, and wherein the DPP-IV inhibitor (preferably vildagliptin or a pharmaceutically acceptable salt thereof) is co-administered with metformin or a pharmaceutically acceptable salt thereof.

In another aspect, the invention relates to a DPP-IV inhibitor (preferably vildagliptin or a pharmaceutically acceptable salt thereof), for use in a method of delaying the increase of $HbA_{1c}$ to greater than or equal to 53 mmol/mol (7.0%) in a patient with type 2 diabetes mellitus, wherein the delay in the increase of $HbA_{1c}$ is relative to metformin monotherapy, and wherein the DPP-IV inhibitor (preferably vildagliptin or a pharmaceutically acceptable salt thereof), is co-administered with metformin or a pharmaceutically acceptable salt thereof.

In another aspect, the invention relates to vildagliptin or a pharmaceutically acceptable salt thereof, for use in a method of delaying the increase of $HbA_{1c}$ to greater than or equal to 53 mmol/mol (7.0%) in a patient with type 2 diabetes mellitus, wherein the delay in the increase of $HbA_{1c}$ is relative to metformin monotherapy, and wherein the vildagliptin or a pharmaceutically acceptable salt thereof, is co-administered with metformin or a pharmaceutically acceptable salt thereof.

In another aspect, the invention relates to a DPP-IV inhibitor (preferably vildagliptin or a pharmaceutically acceptable salt thereof) for use in a method of delaying the increase of $HbA_{1c}$ to greater than or equal to 53 mmol/mol (7.0%) in a patient with type 2 diabetes mellitus, wherein the delay in the increase of $HbA_{1c}$ is relative to metformin monotherapy followed by subsequent co-administration of a DPP-IV inhibitor (preferably vildagliptin or a pharmaceutically acceptable salt thereof) and metformin or a pharmaceutically acceptable salt thereof, and wherein the vildagliptin or a pharmaceutically acceptable salt thereof, is co-administered with metformin or a pharmaceutically acceptable salt thereof.

In another aspect, the invention relates to vildagliptin or a pharmaceutically acceptable salt thereof, for use in a method of delaying the increase of $HbA_{1c}$ to greater than or equal to 53 mmol/mol (7.0%) in a patient with type 2 diabetes mellitus, wherein the delay in the increase of $HbA_{1c}$ is relative to metformin monotherapy followed by subsequent co-administration of a DPP-IV inhibitor (preferably vildagliptin or a pharmaceutically acceptable salt thereof) and metformin or a pharmaceutically acceptable salt thereof, and wherein the vildagliptin or a pharmaceutically acceptable salt thereof, is co-administered with metformin or a pharmaceutically acceptable salt thereof.

In another aspect, the invention relates to a DPP-IV inhibitor (preferably vildagliptin or a pharmaceutically acceptable salt thereof), for use in a method of delaying the increase of $HbA_{1c}$ to greater than or equal to 53 mmol/mol (7.0%) in a patient with type 2 diabetes mellitus, wherein the delay in the increase of $HbA_{1c}$ is relative to metformin monotherapy, and wherein the vildagliptin or a pharmaceutically acceptable salt thereof, is co-administered with metformin or a pharmaceutically acceptable salt thereof, and wherein the patient has not previously received pharmaceutical treatment for the type 2 diabetes mellitus.

In another aspect, the invention relates to vildagliptin or a pharmaceutically acceptable salt thereof, for use in a method of delaying the increase of $HbA_{1c}$ to greater than or equal to 53 mmol/mol (7.0%) in a patient with type 2 diabetes mellitus, wherein the delay in the increase of $HbA_{1c}$ is relative to metformin monotherapy, and wherein the vildagliptin or a pharmaceutically acceptable salt thereof, is co-administered with metformin or a pharmaceutically acceptable salt thereof, and wherein the patient has not previously received pharmaceutical treatment for the type 2 diabetes mellitus.

In another aspect, the invention relates to a DPP-IV inhibitor (preferably vildagliptin or a pharmaceutically acceptable salt thereof), for use in a method of delaying the increase of $HbA_{1c}$ to greater than or equal to 53 mmol/mol (7.0%) in a patient with type 2 diabetes mellitus, wherein the delay in the increase of $HbA_{1c}$ is relative to metformin monotherapy followed by subsequent co-administration of a DPP-IV inhibitor (preferably vildagliptin or a pharmaceutically acceptable salt thereof) and metformin or a pharmaceutically acceptable salt thereof, and wherein the vildagliptin or a pharmaceutically acceptable salt thereof, is co-administered with metformin or a pharmaceutically acceptable salt thereof, and wherein the patient has not previously received pharmaceutical treatment for the type 2 diabetes mellitus.

In another aspect, the invention relates to vildagliptin or a pharmaceutically acceptable salt thereof, for use in a method of delaying the increase of $HbA_{1c}$ to greater than or equal to 53 mmol/mol (7.0%) in a patient with type 2 diabetes mellitus, wherein the delay in the increase of $HbA_{1c}$ is relative to metformin monotherapy followed by subsequent co-administration of a DPP-IV inhibitor (preferably vildagliptin or a pharmaceutically acceptable salt thereof) and metformin or a pharmaceutically acceptable salt thereof, and wherein the vildagliptin or a pharmaceutically acceptable salt thereof, is co-administered with metformin or a pharmaceutically acceptable salt thereof, and wherein the patient has not previously received pharmaceutical treatment for the type 2 diabetes mellitus.

In another aspect, the invention relates to a DPP-IV inhibitor (preferably vildagliptin or a pharmaceutically acceptable salt thereof), for use in a method of delaying the increase of $HbA_{1c}$ to greater than or equal to 53 mmol/mol (7.0%) in a patient with type 2 diabetes mellitus, wherein the patient has not previously received pharmaceutical treatment for the type 2 diabetes mellitus, and wherein the vildagliptin or a pharmaceutically acceptable salt thereof, is co-administered with metformin or a pharmaceutically acceptable salt thereof.

In another aspect, the invention relates to vildagliptin or a pharmaceutically acceptable salt thereof, for use in a method of delaying the increase of $HbA_{1c}$ to greater than or equal to 53 mmol/mol (7.0%) in a patient with type 2 diabetes mellitus, wherein the patient has not previously received pharmaceutical treatment for the type 2 diabetes mellitus, and wherein the vildagliptin or a pharmaceutically acceptable salt thereof, is co-administered with metformin or a pharmaceutically acceptable salt thereof.

In another aspect, the invention relates to a DPP-IV inhibitor (preferably vildagliptin or a pharmaceutically acceptable salt thereof), for use in a method of increasing the time taken to reach an $HbA_{1c}$ measurement of greater than or equal to 53 mmol/mol (7.0%) in a patient with type 2 diabetes mellitus, and wherein the DPP-IV inhibitor (preferably vildagliptin or a pharmaceutically acceptable salt thereof) is co-administered with metformin or a pharmaceutically acceptable salt thereof.

In another aspect, the invention relates to a DPP-IV inhibitor (preferably vildagliptin or a pharmaceutically acceptable salt thereof), for use in a method of increasing the time taken to reach an $HbA_{1c}$ measurement of greater than or equal to 53 mmol/mol (7.0%) in a patient with type 2 diabetes mellitus, wherein the increase is relative to metformin monotherapy, and wherein the DPP-IV inhibitor (preferably vildagliptin or a pharmaceutically acceptable salt thereof) is co-administered with metformin or a pharmaceutically acceptable salt thereof.

In another aspect, the invention relates to vildagliptin or a pharmaceutically acceptable salt thereof, for use in a method of increasing the time taken to reach an $HbA_{1c}$ measurement of greater than or equal to 53 mmol/mol (7.0%) in a patient with type 2 diabetes mellitus, wherein the increase is relative to metformin monotherapy, and wherein the vildagliptin or a pharmaceutically acceptable salt thereof, is co-administered with metformin or a pharmaceutically acceptable salt thereof.

In another aspect, the invention relates to a DPP-IV inhibitor (preferably vildagliptin or a pharmaceutically acceptable salt thereof), for use in a method of increasing the time taken to reach an $HbA_{1c}$ measurement of greater than or equal to 53 mmol/mol (7.0%) in a patient with type 2 diabetes mellitus, wherein the increase is relative to metformin monotherapy followed by subsequent co-administration of a DPP-IV inhibitor (preferably vildagliptin or a pharmaceutically acceptable salt thereof) and metformin or a pharmaceutically acceptable salt thereof, and wherein the DPP-IV inhibitor (preferably vildagliptin or a pharmaceutically acceptable salt thereof) is co-administered with metformin or a pharmaceutically acceptable salt thereof.

In another aspect, the invention relates to vildagliptin or a pharmaceutically acceptable salt thereof, for use in a method of increasing the time taken to reach an $HbA_{1c}$ measurement of greater than or equal to 53 mmol/mol (7.0%) in a patient with type 2 diabetes mellitus, wherein the increase is relative to metformin monotherapy followed by subsequent co-administration of a DPP-IV inhibitor (preferably vildagliptin or a pharmaceutically acceptable salt thereof) and metformin or a pharmaceutically acceptable salt thereof, and wherein the vildagliptin or a pharmaceutically acceptable salt thereof, is co-administered with metformin or a pharmaceutically acceptable salt thereof.

In another aspect, the invention relates to a DPP-IV inhibitor (preferably vildagliptin or a pharmaceutically acceptable salt thereof), for use in a method of increasing the time taken to reach an $HbA_{1c}$ measurement of greater than or equal to 53 mmol/mol (7.0%) in a patient with type 2 diabetes mellitus, wherein the increase is relative to metformin monotherapy, and wherein the DPP-IV inhibitor (preferably vildagliptin or a pharmaceutically acceptable salt thereof) is co-administered with metformin or a pharmaceutically acceptable salt thereof, and wherein the patient has not previously received pharmaceutical treatment for the type 2 diabetes mellitus.

In another aspect, the invention relates to vildagliptin or a pharmaceutically acceptable salt thereof, for use in a method of increasing the time taken to reach an $HbA_{1c}$ measurement of greater than or equal to 53 mmol/mol (7.0%) in a patient with type 2 diabetes mellitus, wherein the increase is relative to metformin monotherapy, and wherein the vildagliptin or a pharmaceutically acceptable salt thereof, is co-administered with metformin or a pharmaceutically acceptable salt thereof, and wherein the patient has not previously received pharmaceutical treatment for the type 2 diabetes mellitus.

In another aspect, the invention relates to a DPP-IV inhibitor (preferably vildagliptin or a pharmaceutically acceptable salt thereof), for use in a method of increasing the time taken to reach an $HbA_{1c}$ measurement of greater than or equal to 53 mmol/mol (7.0%) in a patient with type 2 diabetes mellitus, wherein the increase is relative to metformin monotherapy followed by subsequent co-administration of a DPP-IV inhibitor (preferably vildagliptin or a pharmaceutically acceptable salt thereof) and metformin or a pharmaceutically acceptable salt thereof, and wherein the DPP-IV inhibitor (preferably vildagliptin or a pharmaceutically acceptable salt thereof) is co-administered with metformin or a pharmaceutically acceptable salt thereof, and wherein the patient has not previously received pharmaceutical treatment for the type 2 diabetes mellitus.

In another aspect, the invention relates to vildagliptin or a pharmaceutically acceptable salt thereof, for use in a method of increasing the time taken to reach an $HbA_{1c}$ measurement of greater than or equal to 53 mmol/mol (7.0%) in a patient with type 2 diabetes mellitus, wherein the increase is relative to metformin monotherapy followed by subsequent co-administration of a DPP-IV inhibitor (preferably vildagliptin or a pharmaceutically acceptable salt thereof) and metformin or a pharmaceutically acceptable salt thereof, and wherein the vildagliptin or a pharmaceutically acceptable salt thereof, is co-administered with metformin or a pharmaceutically acceptable salt thereof, and wherein the patient has not previously received pharmaceutical treatment for the type 2 diabetes mellitus.

In another aspect, the invention relates to a DPP-IV inhibitor (preferably vildagliptin or a pharmaceutically acceptable salt thereof), for use in a method of increasing the time taken to reach an $HbA_{1c}$ measurement of greater than or equal to 53 mmol/mol (7.0%) in a patient with type 2 diabetes mellitus, wherein the patient has not previously received pharmaceutical treatment for the type 2 diabetes mellitus, and wherein the DPP-IV inhibitor (preferably vildagliptin or a pharmaceutically acceptable salt thereof) is co-administered with metformin or a pharmaceutically acceptable salt thereof.

In another aspect, the invention relates to vildagliptin or a pharmaceutically acceptable salt thereof, for use in a method of increasing the time taken to reach an $HbA_{1c}$ measurement of greater than or equal to 53 mmol/mol (7.0%) in a patient with type 2 diabetes mellitus, wherein the patient has not previously received pharmaceutical treatment for the type 2 diabetes mellitus, and wherein the vildagliptin or a pharmaceutically acceptable salt thereof, is co-administered with metformin or a pharmaceutically acceptable salt thereof.

In another aspect, the invention relates to a DPP-IV inhibitor (preferably vildagliptin or a pharmaceutically acceptable salt thereof) for use in a method of preventing loss of glycaemic control in a patient with type 2 diabetes mellitus, wherein the DPP-IV inhibitor (preferably vildagliptin or a pharmaceutically acceptable salt thereof) is co-administered with metformin or a pharmaceutically acceptable salt thereof.

In another aspect, the invention relates to vildagliptin or a pharmaceutically acceptable salt thereof, for use in a method of preventing loss of glycaemic control in a patient with type 2 diabetes mellitus, wherein the vildagliptin or a pharmaceutically acceptable salt thereof, is co-administered with metformin or a pharmaceutically acceptable salt thereof.

In another aspect, the invention relates to a DPP-IV inhibitor (preferably vildagliptin or a pharmaceutically acceptable salt thereof) for use in a method of preventing loss of glycaemic control in a patient with type 2 diabetes mellitus, wherein the DPP-IV inhibitor (preferably vildagliptin or a pharmaceutically acceptable salt thereof) is co-administered with metformin or a pharmaceutically acceptable salt thereof, and wherein the patient has not previously received pharmaceutical treatment for the type 2 diabetes mellitus.

In another aspect, the invention relates to vildagliptin or a pharmaceutically acceptable salt thereof, for use in a method of preventing loss of glycaemic control in a patient with type 2 diabetes mellitus, wherein the vildagliptin or a pharmaceutically acceptable salt thereof, is co-administered with metformin or a pharmaceutically acceptable salt thereof, and wherein the patient has not previously received pharmaceutical treatment for the type 2 diabetes mellitus.

In another aspect, the invention relates to a DPP-IV inhibitor (preferably vildagliptin or a pharmaceutically acceptable salt thereof), for use in a method of reducing the risk of a cardiovascular event in a patient undergoing treatment for type 2 diabetes mellitus, wherein the DPP-IV inhibitor (preferably vildagliptin or a pharmaceutically acceptable salt thereof) is co-administered with metformin or a pharmaceutically acceptable salt thereof.

In another aspect, the invention relates to vildagliptin or a pharmaceutically acceptable salt thereof, for use in a method of reducing the risk of a cardiovascular event in a patient undergoing treatment for type 2 diabetes mellitus, wherein the vildagliptin or a pharmaceutically acceptable salt thereof, is co-administered with metformin or a pharmaceutically acceptable salt thereof.

In another aspect, the invention relates to a DPP-IV inhibitor (preferably vildagliptin or a pharmaceutically acceptable salt thereof), for use in a method of reducing the risk of a cardiovascular event in a patient undergoing treatment for type 2 diabetes mellitus, wherein the DPP-IV inhibitor (preferably vildagliptin or a pharmaceutically acceptable salt thereof) is co-administered with metformin or a pharmaceutically acceptable salt thereof, and wherein the risk is reduced relative to metformin monotherapy.

In another aspect, the invention relates to a DPP-IV inhibitor (preferably vildagliptin or a pharmaceutically acceptable salt thereof), for use in a method of reducing the risk of a cardiovascular event in a patient undergoing treatment for type 2 diabetes mellitus, wherein the DPP-IV inhibitor (preferably vildagliptin or a pharmaceutically acceptable salt thereof) is co-administered with metformin or a pharmaceutically acceptable salt thereof, and wherein the risk is reduced relative to metformin monotherapy followed by subsequent co-administration of a DPP-IV inhibitor (preferably vildagliptin or a pharmaceutically acceptable salt thereof) and metformin or a pharmaceutically acceptable salt thereof.

In another aspect, the invention relates to vildagliptin or a pharmaceutically acceptable salt thereof, for use in a method of reducing the risk of a cardiovascular event in a patient undergoing treatment for type 2 diabetes mellitus, wherein the vildagliptin or a pharmaceutically acceptable salt thereof, is co-administered with metformin or a pharmaceutically acceptable salt thereof, and wherein the risk is reduced relative to metformin monotherapy.

In another aspect, the invention relates to vildagliptin or a pharmaceutically acceptable salt thereof, for use in a method of reducing the risk of a cardiovascular event in a patient undergoing treatment for type 2 diabetes mellitus, wherein the vildagliptin or a pharmaceutically acceptable salt thereof, is co-administered with metformin or a pharmaceutically acceptable salt thereof, and wherein the risk is reduced relative to metformin monotherapy followed by subsequent co-administration of a DPP-IV inhibitor (preferably vildagliptin or a pharmaceutically acceptable salt thereof) and metformin or a pharmaceutically acceptable salt thereof.

In another aspect, the invention relates to a DPP-IV inhibitor (preferably vildagliptin or a pharmaceutically acceptable salt thereof), for use in a method of reducing the risk of a cardiovascular event in a patient undergoing treatment for type 2 diabetes mellitus, wherein the DPP-IV inhibitor (preferably vildagliptin or a pharmaceutically acceptable salt thereof) is co-administered with metformin or a pharmaceutically acceptable salt thereof, and wherein the risk is reduced relative to metformin monotherapy, and wherein the patient has not previously received pharmaceutical treatment for the type 2 diabetes mellitus.

In another aspect, the invention relates to a DPP-IV inhibitor (preferably vildagliptin or a pharmaceutically acceptable salt thereof), for use in a method of reducing the risk of a cardiovascular event in a patient undergoing treatment for type 2 diabetes mellitus, wherein the DPP-IV inhibitor (preferably vildagliptin or a pharmaceutically acceptable salt thereof) is co-administered with metformin or a pharmaceutically acceptable salt thereof, and wherein the risk is reduced relative to metformin monotherapy followed by subsequent co-administration of a DPP-IV inhibitor (preferably vildagliptin or a pharmaceutically acceptable salt thereof) and metformin or a pharmaceutically acceptable salt thereof, and wherein the patient has not previously received pharmaceutical treatment for the type 2 diabetes mellitus.

In another aspect, the invention relates to vildagliptin or a pharmaceutically acceptable salt thereof, for use in a method of reducing the risk of a cardiovascular event in a patient undergoing treatment for type 2 diabetes mellitus, wherein the vildagliptin or a pharmaceutically acceptable salt thereof, is co-administered with metformin or a pharmaceutically acceptable salt thereof, and wherein the risk is reduced relative to metformin monotherapy, and wherein the patient has not previously received pharmaceutical treatment for the type 2 diabetes mellitus.

In another aspect, the invention relates to vildagliptin or a pharmaceutically acceptable salt thereof, for use in a method of reducing the risk of a cardiovascular event in a patient undergoing treatment for type 2 diabetes mellitus, wherein the vildagliptin or a pharmaceutically acceptable salt thereof, is co-administered with metformin or a pharmaceutically acceptable salt thereof, and wherein the risk is reduced relative to metformin monotherapy followed by subsequent co-administration of a DPP-IV inhibitor (preferably vildagliptin or a pharmaceutically acceptable salt thereof) and metformin or a pharmaceutically acceptable salt thereof, and wherein the patient has not previously received pharmaceutical treatment for the type 2 diabetes mellitus.

In another aspect, the invention relates to a DPP-IV inhibitor (preferably vildagliptin or a pharmaceutically acceptable salt thereof), for use in a method of reducing the risk of a cardiovascular event in a patient undergoing treatment for type 2 diabetes mellitus, wherein the DPP-IV inhibitor (preferably vildagliptin or a pharmaceutically acceptable salt thereof) is co-administered with metformin or a pharmaceutically acceptable salt thereof, and wherein the patient has not previously received pharmaceutical treatment for the type 2 diabetes mellitus.

In another aspect, the invention relates to vildagliptin or a pharmaceutically acceptable salt thereof, for use in a method of reducing the risk of a cardiovascular event in a patient undergoing treatment for type 2 diabetes mellitus, wherein the vildagliptin or a pharmaceutically acceptable salt thereof, is co-administered with metformin or a pharmaceutically acceptable salt thereof, and wherein the patient has not previously received pharmaceutical treatment for the type 2 diabetes mellitus.

In another aspect, the invention relates to a DPP-IV inhibitor (preferably vildagliptin or a pharmaceutically acceptable salt thereof), or a pharmaceutically acceptable salt thereof, for use in a method of treating type 2 diabetes mellitus without concomitant administration of insulin, and wherein the DPP-IV inhibitor (preferably vildagliptin or a pharmaceutically acceptable salt thereof) is co-administered with metformin or a pharmaceutically acceptable salt thereof.

In another aspect, the invention relates to vildagliptin or a pharmaceutically acceptable salt thereof, for use in a method of treating type 2 diabetes mellitus without concomitant administration of insulin, and wherein the vildagliptin or a pharmaceutically acceptable salt thereof is co-administered with metformin or a pharmaceutically acceptable salt thereof.

In another aspect, the invention relates to a DPP-IV inhibitor (preferably vildagliptin or a pharmaceutically acceptable salt thereof), or a pharmaceutically acceptable salt thereof, for use in a method of treating type 2 diabetes mellitus without concomitant administration of insulin, and wherein the DPP-IV inhibitor (preferably vildagliptin or a pharmaceutically acceptable salt thereof) is co-administered with metformin or a pharmaceutically acceptable salt thereof, and wherein the patient has not previously received pharmaceutical treatment for the type 2 diabetes mellitus.

In another aspect, the invention relates to vildagliptin or a pharmaceutically acceptable salt thereof, for use in a method of treating type 2 diabetes mellitus without concomitant administration of insulin, and wherein the vildagliptin or a pharmaceutically acceptable salt thereof is co-administered with metformin or a pharmaceutically acceptable salt thereof, and wherein the patient has not previously received pharmaceutical treatment for the type 2 diabetes mellitus.

In another aspect, the invention relates to metformin or a pharmaceutically acceptable salt thereof, for use in a method of delaying loss of glycaemic control in a patient with type 2 diabetes mellitus, wherein the metformin or a pharmaceutically acceptable salt thereof, is co-administered with a DPP-IV inhibitor (preferably vildagliptin or a pharmaceutically acceptable salt thereof).

In another aspect, the invention relates to metformin or a pharmaceutically acceptable salt thereof, for use in a method of delaying loss of glycaemic control in a patient with type 2 diabetes mellitus, wherein the metformin or a pharmaceutically acceptable salt thereof, is co-administered with a DPP-IV inhibitor (preferably vildagliptin or a pharmaceutically acceptable salt thereof), and wherein the loss of glycaemic control is delayed relative to metformin monotherapy.

In another aspect, the invention relates to metformin or a pharmaceutically acceptable salt thereof, for use in a method of delaying loss of glycaemic control in a patient with type 2 diabetes mellitus, wherein the metformin or a pharmaceutically acceptable salt thereof, is co-administered with vildagliptin or a pharmaceutically acceptable salt thereof, and wherein the loss of glycaemic control is delayed relative to metformin monotherapy.

In another aspect, the invention relates to metformin or a pharmaceutically acceptable salt thereof, for use in a method of delaying loss of glycaemic control in a patient with type 2 diabetes mellitus, wherein the metformin or a pharmaceutically acceptable salt thereof, is co-administered with a DPP-IV inhibitor (preferably vildagliptin or a pharmaceutically acceptable salt thereof), and wherein the loss of glycaemic control is delayed relative to metformin monotherapy followed by subsequent co-administration of a DPP-IV inhibitor (preferably vildagliptin or a pharmaceutically acceptable salt thereof) and metformin or a pharmaceutically acceptable salt thereof.

In another aspect, the invention relates to metformin or a pharmaceutically acceptable salt thereof, for use in a method of delaying loss of glycaemic control in a patient with type 2 diabetes mellitus, wherein the metformin or a pharmaceutically acceptable salt thereof, is co-administered with vildagliptin or a pharmaceutically acceptable salt thereof, and wherein the loss of glycaemic control is delayed relative to metformin monotherapy followed by subsequent co-administration of a DPP-IV inhibitor (preferably vildagliptin or a pharmaceutically acceptable salt thereof) and metformin or a pharmaceutically acceptable salt thereof.

In another aspect, the invention relates to metformin or a pharmaceutically acceptable salt thereof, for use in a method of delaying loss of glycaemic control in a patient with type 2 diabetes mellitus, wherein the metformin or a pharmaceutically acceptable salt thereof, is co-administered with a DPP-IV inhibitor (preferably vildagliptin or a pharmaceutically acceptable salt thereof), and wherein the loss of glycaemic control is delayed relative to metformin monotherapy, and wherein the patient has not previously received pharmaceutical treatment for the type 2 diabetes mellitus.

In another aspect, the invention relates to metformin or a pharmaceutically acceptable salt thereof, for use in a method of delaying loss of glycaemic control in a patient with type 2 diabetes mellitus, wherein the metformin or a pharmaceutically acceptable salt thereof, is co-administered with vildagliptin or a pharmaceutically acceptable salt thereof, and wherein the loss of glycaemic control is delayed relative to metformin monotherapy, and wherein the patient has not previously received pharmaceutical treatment for the type 2 diabetes mellitus.

In another aspect, the invention relates to metformin or a pharmaceutically acceptable salt thereof, for use in a method of delaying loss of glycaemic control in a patient with type 2 diabetes mellitus, wherein the metformin or a pharmaceutically acceptable salt thereof, is co-administered with a DPP-IV inhibitor (preferably vildagliptin or a pharmaceutically acceptable salt thereof), and wherein the loss of glycaemic control is delayed relative to metformin monotherapy followed by subsequent co-administration of a DPP-IV inhibitor (preferably vildagliptin or a pharmaceutically acceptable salt thereof) and metformin or a pharmaceutically acceptable salt thereof, and wherein the patient has not previously received pharmaceutical treatment for the type 2 diabetes mellitus.

In another aspect, the invention relates to metformin or a pharmaceutically acceptable salt thereof, for use in a method of delaying loss of glycaemic control in a patient with type 2 diabetes mellitus, wherein the metformin or a pharmaceutically acceptable salt thereof, is co-administered with vildagliptin or a pharmaceutically acceptable salt thereof, and wherein the loss of glycaemic control is delayed relative to metformin monotherapy followed by subsequent co-administration of a DPP-IV inhibitor (preferably vildagliptin or a pharmaceutically acceptable salt thereof) and metformin or a pharmaceutically acceptable salt thereof, and wherein the patient has not previously received pharmaceutical treatment for the type 2 diabetes mellitus.

In another aspect, the invention relates to metformin or a pharmaceutically acceptable salt thereof, for use in a method of delaying loss of glycaemic control in a patient with type 2 diabetes mellitus, wherein the metformin or a pharmaceutically acceptable salt thereof, is co-administered with a DPP-IV inhibitor (preferably vildagliptin or a pharmaceutically acceptable salt thereof), and wherein the patient has not previously received pharmaceutical treatment for the type 2 diabetes mellitus.

In another aspect, the invention relates to metformin or a pharmaceutically acceptable salt thereof, for use in a method of delaying loss of glycaemic control in a patient with type 2 diabetes mellitus, wherein the metformin or a pharmaceutically acceptable salt thereof, is co-administered with vildagliptin or a pharmaceutically acceptable salt thereof, and wherein the patient has not previously received pharmaceutical treatment for the type 2 diabetes mellitus.

In another aspect, the invention relates to metformin or a pharmaceutically acceptable salt thereof, for use in a method of improving glycaemic control in a patient with type 2 diabetes mellitus, wherein the metformin or a pharmaceutically acceptable salt thereof, is co-administered with a DPP-IV inhibitor (preferably vildagliptin or a pharmaceutically acceptable salt thereof).

In another aspect, the invention relates to metformin or a pharmaceutically acceptable salt thereof, for use in a method of improving glycaemic control in a patient with type 2 diabetes mellitus, wherein the metformin or a pharmaceutically acceptable salt thereof, is co-administered with a DPP-IV inhibitor (preferably vildagliptin or a pharmaceutically acceptable salt thereof), and wherein the improvement in glycaemic control is relative to metformin monotherapy.

In another aspect, the invention relates to metformin or a pharmaceutically acceptable salt thereof, for use in a method of improving glycaemic control in a patient with type 2 diabetes mellitus, wherein the metformin or a pharmaceutically acceptable salt thereof, is co-administered with vildagliptin or a pharmaceutically acceptable salt thereof, and wherein the improvement in glycaemic control is relative to metformin monotherapy.

In another aspect, the invention relates to metformin or a pharmaceutically acceptable salt thereof, for use in a method of improving glycaemic control in a patient with type 2 diabetes mellitus, wherein the metformin or a pharmaceutically acceptable salt thereof, is co-administered with a DPP-IV inhibitor (preferably vildagliptin or a pharmaceutically acceptable salt thereof), and wherein the improvement in glycaemic control is relative to metformin monotherapy followed by subsequent co-administration of a DPP-IV inhibitor (preferably vildagliptin or a pharmaceutically acceptable salt thereof) and metformin or a pharmaceutically acceptable salt thereof.

In another aspect, the invention relates to metformin or a pharmaceutically acceptable salt thereof, for use in a method of improving glycaemic control in a patient with type 2 diabetes mellitus, wherein the metformin or a pharmaceutically acceptable salt thereof, is co-administered with vildagliptin or a pharmaceutically acceptable salt thereof, and wherein the improvement in glycaemic control is relative to metformin monotherapy followed by subsequent co-administration of a DPP-IV inhibitor (preferably vildagliptin or a pharmaceutically acceptable salt thereof) and metformin or a pharmaceutically acceptable salt thereof.

In another aspect, the invention relates to metformin or a pharmaceutically acceptable salt thereof, for use in a method of improving glycaemic control in a patient with type 2 diabetes mellitus, wherein the metformin or a pharmaceutically acceptable salt thereof, is co-administered with a DPP-IV inhibitor (preferably vildagliptin or a pharmaceutically acceptable salt thereof), and wherein the improvement in glycaemic control is relative to metformin monotherapy, and the patient has not previously received pharmaceutical treatment for the type 2 diabetes mellitus.

In another aspect, the invention relates to metformin or a pharmaceutically acceptable salt thereof, for use in a method of improving glycaemic control in a patient with type 2 diabetes mellitus, wherein the metformin or a pharmaceutically acceptable salt thereof, is co-administered with vildagliptin or a pharmaceutically acceptable salt thereof, and wherein the improvement in glycaemic control is relative to metformin monotherapy, and the patient has not previously received pharmaceutical treatment for the type 2 diabetes mellitus.

In another aspect, the invention relates to metformin or a pharmaceutically acceptable salt thereof, for use in a method of improving glycaemic control in a patient with type 2 diabetes mellitus, wherein the metformin or a pharmaceutically acceptable salt thereof, is co-administered with a DPP-IV inhibitor (preferably vildagliptin or a pharmaceutically acceptable salt thereof), and wherein the improvement in glycaemic control is relative to metformin monotherapy followed by subsequent co-administration of a DPP-IV inhibitor (preferably vildagliptin or a pharmaceutically acceptable salt thereof) and metformin or a pharmaceutically acceptable salt thereof, and the patient has not previously received pharmaceutical treatment for the type 2 diabetes mellitus.

In another aspect, the invention relates to metformin or a pharmaceutically acceptable salt thereof, for use in a method of improving glycaemic control in a patient with type 2 diabetes mellitus, wherein the metformin or a pharmaceutically acceptable salt thereof, is co-administered with vildagliptin or a pharmaceutically acceptable salt thereof, and wherein the improvement in glycaemic control is relative to metformin monotherapy followed by subsequent co-administration of a DPP-IV inhibitor (preferably vildagliptin or a pharmaceutically acceptable salt thereof) and metformin or a pharmaceutically acceptable salt thereof, and wherein the patient has not previously received pharmaceutical treatment for the type 2 diabetes mellitus.

In another aspect, the invention relates to metformin or a pharmaceutically acceptable salt thereof, for use in a method of improving glycaemic control in a patient with type 2 diabetes mellitus, wherein the metformin or a pharmaceutically acceptable salt thereof, is co-administered with a DPP-IV inhibitor (preferably vildagliptin or a pharmaceutically acceptable salt thereof), and the patient has not previously received pharmaceutical treatment for the type 2 diabetes mellitus.

In another aspect, the invention relates to metformin or a pharmaceutically acceptable salt thereof, for use in a method of improving glycaemic control in a patient with type 2 diabetes mellitus, wherein the metformin or a pharmaceutically acceptable salt thereof, is co-administered with vildagliptin or a pharmaceutically acceptable salt thereof, and wherein the patient has not previously received pharmaceutical treatment for the type 2 diabetes mellitus.

In another aspect, the invention relates to metformin or a pharmaceutically acceptable salt thereof, for use in a method of delaying the increase of $HbA_{1c}$ to greater than or equal to 53 mmol/mol (7.0%) in a patient with type 2 diabetes mellitus, wherein the metformin or a pharmaceutically acceptable salt thereof, is co-administered with a DPP-IV inhibitor (preferably vildagliptin or a pharmaceutically acceptable salt thereof).

In another aspect, the invention relates to metformin or a pharmaceutically acceptable salt thereof, for use in a method of delaying the increase of $HbA_{1c}$ to greater than or equal to 53 mmol/mol (7.0%) in a patient with type 2 diabetes mellitus, wherein the metformin or a pharmaceutically acceptable salt thereof, is co-administered with a DPP-IV inhibitor (preferably vildagliptin or a pharmaceutically acceptable salt thereof), and wherein the delay in the increase of $HbA_{1c}$ is relative to metformin monotherapy.

In another aspect, the invention relates to metformin or a pharmaceutically acceptable salt thereof, for use in a method of delaying the increase of $HbA_{1c}$ to greater than or equal to 53 mmol/mol (7.0%) in a patient with type 2 diabetes mellitus, wherein the metformin or a pharmaceutically acceptable salt thereof, is co-administered with vildagliptin or a pharmaceutically acceptable salt thereof, and wherein the delay in the increase of $HbA_{1c}$ is relative to metformin monotherapy.

In another aspect, the invention relates to metformin or a pharmaceutically acceptable salt thereof, for use in a method of delaying the increase of $HbA_{1c}$ to greater than or equal to 53 mmol/mol (7.0%) in a patient with type 2 diabetes mellitus, wherein the metformin or a pharmaceutically acceptable salt thereof, is co-administered with a DPP-IV inhibitor (preferably vildagliptin or a pharmaceutically acceptable salt thereof), and wherein the delay in the increase of $HbA_{1c}$ is relative to metformin monotherapy followed by subsequent co-administration of a DPP-IV inhibitor (preferably vildagliptin or a pharmaceutically acceptable salt thereof) and metformin.

In another aspect, the invention relates to metformin or a pharmaceutically acceptable salt thereof, for use in a method of delaying the increase of $HbA_{1c}$ to greater than or equal to 53 mmol/mol (7.0%) in a patient with type 2 diabetes mellitus, wherein the metformin or a pharmaceutically acceptable salt thereof, is co-administered with vildagliptin or a pharmaceutically acceptable salt thereof, and wherein the delay in the increase of $HbA_{1c}$ is relative to metformin monotherapy followed by subsequent co-administration of a DPP-IV inhibitor (preferably vildagliptin or a pharmaceutically acceptable salt thereof) and metformin or a pharmaceutically acceptable salt thereof.

In another aspect, the invention relates to metformin or a pharmaceutically acceptable salt thereof, for use in a method of delaying the increase of $HbA_{1c}$ to greater than or equal to 53 mmol/mol (7.0%) in a patient with type 2 diabetes mellitus, wherein the metformin or a pharmaceutically acceptable salt thereof, is co-administered with a DPP-IV inhibitor (preferably vildagliptin or a pharmaceutically acceptable salt thereof), and wherein the delay in the increase of $HbA_{1c}$ is relative to metformin monotherapy, and wherein the patient has not previously received pharmaceutical treatment for the type 2 diabetes mellitus.

In another aspect, the invention relates to metformin or a pharmaceutically acceptable salt thereof, for use in a method of delaying the increase of $HbA_{1c}$ to greater than or equal to 53 mmol/mol (7.0%) in a patient with type 2 diabetes mellitus, wherein the metformin or a pharmaceutically acceptable salt thereof, is co-administered with vildagliptin or a pharmaceutically acceptable salt thereof, and wherein the delay in the increase of $HbA_{1c}$ is relative to metformin monotherapy, and wherein the patient has not previously received pharmaceutical treatment for the type 2 diabetes mellitus.

In another aspect, the invention relates to metformin or a pharmaceutically acceptable salt thereof, for use in a method of delaying the increase of $HbA_{1c}$ to greater than or equal to 53 mmol/mol (7.0%) in a patient with type 2 diabetes mellitus, wherein the metformin or a pharmaceutically acceptable salt thereof, is co-administered with a DPP-IV inhibitor (preferably vildagliptin or a pharmaceutically acceptable salt thereof), and wherein the delay in the increase of $HbA_{1c}$ is relative to metformin monotherapy followed by subsequent co-administration of a DPP-IV inhibitor (preferably vildagliptin or a pharmaceutically acceptable salt thereof) and metformin or a pharmaceutically acceptable salt thereof, and wherein the patient has not previously received pharmaceutical treatment for the type 2 diabetes mellitus.

In another aspect, the invention relates to metformin or a pharmaceutically acceptable salt thereof, for use in a method of delaying the increase of $HbA_{1c}$ to greater than or equal to 53 mmol/mol (7.0%) in a patient with type 2 diabetes mellitus, wherein the metformin or a pharmaceutically acceptable salt thereof, is co-administered with vildagliptin or a pharmaceutically acceptable salt thereof, and wherein the delay in the increase of $HbA_{1c}$ is relative to metformin monotherapy followed by subsequent co-administration of a DPP-IV inhibitor (preferably vildagliptin or a pharmaceutically acceptable salt thereof) and metformin or a pharmaceutically acceptable salt thereof, and wherein the patient has not previously received pharmaceutical treatment for the type 2 diabetes mellitus.

In another aspect, the invention relates to metformin or a pharmaceutically acceptable salt thereof, for use in a method of delaying the increase of $HbA_{1c}$ to greater than or equal to 53 mmol/mol (7.0%) in a patient with type 2 diabetes mellitus, wherein the metformin or a pharmaceutically acceptable salt thereof, is co-administered with a DPP-IV inhibitor (preferably vildagliptin or a pharmaceutically acceptable salt thereof), and wherein the patient has not previously received pharmaceutical treatment for the type 2 diabetes mellitus.

In another aspect, the invention relates to metformin or a pharmaceutically acceptable salt thereof, for use in a method of delaying the increase of $HbA_{1c}$ to greater than or equal to 53 mmol/mol (7.0%) in a patient with type 2 diabetes mellitus, wherein the metformin or a pharmaceutically acceptable salt thereof, is co-administered with vildagliptin or a pharmaceutically acceptable salt thereof, and wherein the patient has not previously received pharmaceutical treatment for the type 2 diabetes mellitus.

In another aspect, the invention relates to metformin or a pharmaceutically acceptable salt thereof, for use in a method of increasing the time taken to reach an $HbA_{1c}$ measurement of greater than or equal to 53 mmol/mol (7.0%) in a patient with type 2 diabetes mellitus, and wherein the metformin or a pharmaceutically acceptable salt thereof, is co-administered with a DPP-IV inhibitor (preferably vildagliptin or a pharmaceutically acceptable salt thereof).

In another aspect, the invention relates to metformin or a pharmaceutically acceptable salt thereof, for use in a method of increasing the time taken to reach an $HbA_{1c}$ measurement of greater than or equal to 53 mmol/mol (7.0%) in a patient with type 2 diabetes mellitus, wherein the increase is relative to metformin monotherapy, and wherein the metformin or a pharmaceutically acceptable salt thereof, is co-administered with a DPP-IV inhibitor (preferably vildagliptin or a pharmaceutically acceptable salt thereof).

In another aspect, the invention relates to metformin or a pharmaceutically acceptable salt thereof, for use in a method of increasing the time taken to reach an $HbA_{1c}$ measurement of greater than or equal to 53 mmol/mol (7.0%) in a patient with type 2 diabetes mellitus, wherein the increase is relative to metformin monotherapy, and wherein the metformin or a pharmaceutically acceptable salt thereof, is co-administered with vildagliptin or a pharmaceutically acceptable salt thereof.

In another aspect, the invention relates to metformin or a pharmaceutically acceptable salt thereof, for use in a method of increasing the time taken to reach an $HbA_{1c}$ measurement of greater than or equal to 53 mmol/mol (7.0%) in a patient with type 2 diabetes mellitus, wherein the increase is relative to metformin monotherapy followed by subsequent co-administration of a DPP-IV inhibitor (preferably vildagliptin or a pharmaceutically acceptable salt thereof) and metformin or a pharmaceutically acceptable salt thereof, and wherein the metformin or a pharmaceutically acceptable salt thereof, is co-administered with a DPP-IV inhibitor (preferably vildagliptin or a pharmaceutically acceptable salt thereof).

In another aspect, the invention relates to metformin or a pharmaceutically acceptable salt thereof, for use in a method of increasing the time taken to reach an $HbA_{1c}$ measurement of greater than or equal to 53 mmol/mol (7.0%) in a patient with type 2 diabetes mellitus, wherein the increase is relative to metformin monotherapy followed by subsequent co-administration of a DPP-IV inhibitor (preferably vildagliptin or a pharmaceutically acceptable salt thereof) and metformin or a pharmaceutically acceptable salt thereof, and wherein the metformin or a pharmaceutically acceptable salt thereof, is co-administered with vildagliptin or a pharmaceutically acceptable salt thereof.

In another aspect, the invention relates to metformin or a pharmaceutically acceptable salt thereof, for use in a method of increasing the time taken to reach an $HbA_{1c}$ measurement of greater than or equal to 53 mmol/mol (7.0%) in a patient with type 2 diabetes mellitus, wherein the increase is relative to metformin monotherapy, and wherein the metformin or a pharmaceutically acceptable salt thereof, is co-administered with a DPP-IV inhibitor (preferably vildagliptin or a pharmaceutically acceptable salt thereof), and wherein the patient has not previously received pharmaceutical treatment for the type 2 diabetes mellitus.

In another aspect, the invention relates to metformin or a pharmaceutically acceptable salt thereof, for use in a method of increasing the time taken to reach an HbA$_{1c}$ measurement of greater than or equal to 53 mmol/mol (7.0%) in a patient with type 2 diabetes mellitus, wherein the increase is relative to metformin monotherapy, and wherein the metformin or a pharmaceutically acceptable salt thereof, is co-administered with vildagliptin or a pharmaceutically acceptable salt thereof, and wherein the patient has not previously received pharmaceutical treatment for the type 2 diabetes mellitus.

In another aspect, the invention relates to metformin or a pharmaceutically acceptable salt thereof, for use in a method of increasing the time taken to reach an HbA$_{1c}$ measurement of greater than or equal to 53 mmol/mol (7.0%) in a patient with type 2 diabetes mellitus, wherein the increase is relative to metformin monotherapy followed by subsequent co-administration of a DPP-IV inhibitor (preferably vildagliptin or a pharmaceutically acceptable salt thereof) and metformin or a pharmaceutically acceptable salt thereof, and wherein the metformin or a pharmaceutically acceptable salt thereof, is co-administered with a DPP-IV inhibitor (preferably vildagliptin or a pharmaceutically acceptable salt thereof), and wherein the patient has not previously received pharmaceutical treatment for the type 2 diabetes mellitus.

In another aspect, the invention relates to metformin or a pharmaceutically acceptable salt thereof, for use in a method of increasing the time taken to reach an HbA$_{1c}$ measurement of greater than or equal to 53 mmol/mol (7.0%) in a patient with type 2 diabetes mellitus, wherein the increase is relative to metformin monotherapy followed by subsequent co-administration of a DPP-IV inhibitor (preferably vildagliptin or a pharmaceutically acceptable salt thereof) and metformin or a pharmaceutically acceptable salt thereof, and wherein the metformin or a pharmaceutically acceptable salt thereof, is co-administered with vildagliptin or a pharmaceutically acceptable salt thereof, and wherein the patient has not previously received pharmaceutical treatment for the type 2 diabetes mellitus.

In another aspect, the invention relates to metformin or a pharmaceutically acceptable salt thereof, for use in a method of increasing the time taken to reach an HbA$_{1c}$ measurement of greater than or equal to 53 mmol/mol (7.0%) in a patient with type 2 diabetes mellitus, wherein the patient has not previously received pharmaceutical treatment for the type 2 diabetes mellitus, and wherein the metformin or a pharmaceutically acceptable salt thereof, is co-administered with a DPP-IV inhibitor (preferably vildagliptin or a pharmaceutically acceptable salt thereof).

In another aspect, the invention relates to metformin or a pharmaceutically acceptable salt thereof, for use in a method of increasing the time taken to reach an HbA$_{1c}$ measurement of greater than or equal to 53 mmol/mol (7.0%) in a patient with type 2 diabetes mellitus, wherein the patient has not previously received pharmaceutical treatment for the type 2 diabetes mellitus, and wherein the metformin or a pharmaceutically acceptable salt thereof, is co-administered with vildagliptin or a pharmaceutically acceptable salt thereof.

In another aspect, the invention relates to metformin or a pharmaceutically acceptable salt thereof, for use in a method of preventing loss of glycaemic control in a patient with type 2 diabetes mellitus, wherein the metformin or a pharmaceutically acceptable salt thereof, is co-administered with a DPP-IV inhibitor (preferably vildagliptin or a pharmaceutically acceptable salt thereof).

In another aspect, the invention relates to metformin or a pharmaceutically acceptable salt thereof, for use in a method of preventing loss of glycaemic control in a patient with type 2 diabetes mellitus, wherein the metformin or a pharmaceutically acceptable salt thereof, is co-administered with vildagliptin or a pharmaceutically acceptable salt thereof.

In another aspect, the invention relates to metformin or a pharmaceutically acceptable salt thereof, for use in a method of preventing loss of glycaemic control in a patient with type 2 diabetes mellitus, wherein the metformin or a pharmaceutically acceptable salt thereof, is co-administered with a DPP-IV inhibitor (preferably vildagliptin or a pharmaceutically acceptable salt thereof), and wherein the patient has not previously received pharmaceutical treatment for the type 2 diabetes mellitus.

In another aspect, the invention relates to metformin or a pharmaceutically acceptable salt thereof, for use in a method of preventing loss of glycaemic control in a patient with type 2 diabetes mellitus, wherein the metformin or a pharmaceutically acceptable salt thereof, is co-administered with vildagliptin or a pharmaceutically acceptable salt thereof, and wherein the patient has not previously received pharmaceutical treatment for the type 2 diabetes mellitus.

In another aspect, the invention relates to metformin or a pharmaceutically acceptable salt thereof, for use in a method of reducing the risk of a cardiovascular event in a patient undergoing treatment for type 2 diabetes mellitus, wherein the metformin or a pharmaceutically acceptable salt thereof, is co-administered with a DPP-IV inhibitor (preferably vildagliptin or a pharmaceutically acceptable salt thereof).

In another aspect, the invention relates to metformin or a pharmaceutically acceptable salt thereof, for use in a method of reducing the risk of a cardiovascular event in a patient undergoing treatment for type 2 diabetes mellitus, wherein the metformin or a pharmaceutically acceptable salt thereof, is co-administered with vildagliptin or a pharmaceutically acceptable salt thereof.

In another aspect, the invention relates to metformin or a pharmaceutically acceptable salt thereof, for use in a method of reducing the risk of a cardiovascular event in a patient undergoing treatment for type 2 diabetes mellitus, wherein the metformin or a pharmaceutically acceptable salt thereof, is co-administered with a DPP-IV inhibitor (preferably vildagliptin or a pharmaceutically acceptable salt thereof), and wherein the patient has not previously received pharmaceutical treatment for the type 2 diabetes mellitus.

In another aspect, the invention relates to metformin or a pharmaceutically acceptable salt thereof, for use in a method of reducing the risk of a cardiovascular event in a patient undergoing treatment for type 2 diabetes mellitus, wherein the metformin or a pharmaceutically acceptable salt thereof, is co-administered with vildagliptin or a pharmaceutically acceptable salt thereof, and wherein the patient has not previously received pharmaceutical treatment for the type 2 diabetes mellitus.

In another aspect, the invention relates to metformin or a pharmaceutically acceptable salt thereof, for use in a method of reducing the risk of a cardiovascular event in a patient undergoing treatment for type 2 diabetes mellitus, wherein the metformin or a pharmaceutically acceptable salt thereof, is co-administered with a DPP-IV inhibitor (preferably vildagliptin or a pharmaceutically acceptable salt thereof), and wherein the risk of a cardiovascular event is reduced relative to metformin monotherapy.

In another aspect, the invention relates to metformin or a pharmaceutically acceptable salt thereof, for use in a method of reducing the risk of a cardiovascular event in a patient undergoing treatment for type 2 diabetes mellitus, wherein the metformin or a pharmaceutically acceptable salt thereof, is co-administered with vildagliptin or a pharmaceutically acceptable salt thereof, and wherein the risk of a cardiovascular event is reduced relative to metformin monotherapy.

In another aspect, the invention relates to metformin or a pharmaceutically acceptable salt thereof, for use in a method of reducing the risk of a cardiovascular event in a patient undergoing treatment for type 2 diabetes mellitus, wherein the metformin or a pharmaceutically acceptable salt thereof, is co-administered with a DPP-IV inhibitor (preferably vildagliptin or a pharmaceutically acceptable salt thereof), and wherein the risk of a cardiovascular event is reduced relative to metformin monotherapy followed by subsequent co-administration of a DPP-IV inhibitor (preferably vildagliptin or a pharmaceutically acceptable salt thereof) and metformin or a pharmaceutically acceptable salt thereof.

In another aspect, the invention relates to metformin or a pharmaceutically acceptable salt thereof, for use in a method of reducing the risk of a cardiovascular event in a patient undergoing treatment for type 2 diabetes mellitus, wherein the metformin or a pharmaceutically acceptable salt thereof, is co-administered with vildagliptin or a pharmaceutically acceptable salt thereof, and wherein the risk of a cardiovascular event is reduced relative to metformin monotherapy followed by subsequent co-administration of a DPP-IV inhibitor (preferably vildagliptin or a pharmaceutically acceptable salt thereof) and metformin or a pharmaceutically acceptable salt thereof.

In another aspect, the invention relates to metformin or a pharmaceutically acceptable salt thereof, for use in a method of reducing the risk of a cardiovascular event in a patient undergoing treatment for type 2 diabetes mellitus, wherein the metformin or a pharmaceutically acceptable salt thereof, is co-administered with a DPP-IV inhibitor (preferably vildagliptin or a pharmaceutically acceptable salt thereof), and wherein the risk of a cardiovascular event is reduced relative to metformin monotherapy, and wherein the patient has not previously received pharmaceutical treatment for the type 2 diabetes mellitus.

In another aspect, the invention relates to metformin or a pharmaceutically acceptable salt thereof, for use in a method of reducing the risk of a cardiovascular event in a patient undergoing treatment for type 2 diabetes mellitus, wherein the metformin or a pharmaceutically acceptable salt thereof, is co-administered with vildagliptin or a pharmaceutically acceptable salt thereof, and wherein the risk of a cardiovascular event is reduced relative to metformin monotherapy, and wherein the patient has not previously received pharmaceutical treatment for the type 2 diabetes mellitus.

In another aspect, the invention relates to metformin or a pharmaceutically acceptable salt thereof, for use in a method of reducing the risk of a cardiovascular event in a patient undergoing treatment for type 2 diabetes mellitus, wherein the metformin or a pharmaceutically acceptable salt thereof, is co-administered with a DPP-IV inhibitor (preferably vildagliptin or a pharmaceutically acceptable salt thereof), and wherein the risk of a cardiovascular event is reduced relative to metformin monotherapy followed by subsequent co-administration of a DPP-IV inhibitor (preferably vildagliptin or a pharmaceutically acceptable salt thereof) and metformin or a pharmaceutically acceptable salt thereof, and wherein the patient has not previously received pharmaceutical treatment for the type 2 diabetes mellitus.

In another aspect, the invention relates to metformin or a pharmaceutically acceptable salt thereof, for use in a method of reducing the risk of a cardiovascular event in a patient undergoing treatment for type 2 diabetes mellitus, wherein the metformin or a pharmaceutically acceptable salt thereof, is co-administered with vildagliptin or a pharmaceutically acceptable salt thereof, and wherein the risk of a cardiovascular event is reduced relative to metformin monotherapy followed by subsequent co-administration of a DPP-IV inhibitor (preferably vildagliptin or a pharmaceutically acceptable salt thereof) and metformin or a pharmaceutically acceptable salt thereof, and wherein the patient has not previously received pharmaceutical treatment for the type 2 diabetes mellitus.

In another aspect, the invention relates to metformin or a pharmaceutically acceptable salt thereof, for use in a method of treating type 2 diabetes mellitus without concomitant administration of insulin, and wherein the metformin or a pharmaceutically acceptable salt thereof, is co-administered with DPP-IV inhibitor (preferably vildagliptin or a pharmaceutically acceptable salt thereof).

In another aspect, the invention relates to metformin or a pharmaceutically acceptable salt thereof, for use in a method of treating type 2 diabetes mellitus without concomitant administration of insulin, wherein the metformin or a pharmaceutically acceptable salt thereof, is co-administered with vildagliptin or a pharmaceutically acceptable salt thereof.

In another aspect, the invention relates to metformin or a pharmaceutically acceptable salt thereof, for use in a method of treating type 2 diabetes mellitus without concomitant administration of insulin, and wherein the metformin or a pharmaceutically acceptable salt thereof, is co-administered with DPP-IV inhibitor (preferably vildagliptin or a pharmaceutically acceptable salt thereof), wherein the patient has not previously received pharmaceutical treatment for the type 2 diabetes mellitus.

In another aspect, the invention relates to metformin or a pharmaceutically acceptable salt thereof, for use in a method of treating type 2 diabetes mellitus without concomitant administration of insulin, wherein the metformin or a pharmaceutically acceptable salt thereof, is co-administered with vildagliptin or a pharmaceutically acceptable salt thereof, wherein the patient has not previously received pharmaceutical treatment for the type 2 diabetes mellitus.

Methods of Treatment

In one aspect, the invention relates to a method of delaying loss of glycaemic control in a patient with type 2 diabetes mellitus, wherein the method comprises administering to the patient a combination of a DPP-IV inhibitor (preferably vildagliptin or a pharmaceutically acceptable salt thereof), and metformin or a pharmaceutically acceptable salt thereof.

In one aspect, the invention relates to a method of delaying loss of glycaemic control in a patient with type 2 diabetes mellitus, wherein the method comprises administering to the patient a combination of a vildagliptin or a pharmaceutically acceptable salt thereof and metformin or a pharmaceutically acceptable salt thereof.

In one aspect, the invention relates to a method of delaying loss of glycaemic control in a patient with type 2 diabetes mellitus, wherein the method comprises administering to the patient a combination of a DPP-IV inhibitor (preferably vildagliptin or a pharmaceutically acceptable salt thereof), and metformin or a pharmaceutically acceptable salt thereof.

In one aspect, the invention relates to a method of delaying loss of glycaemic control in a patient with type 2 diabetes mellitus, wherein the method comprises administering to the patient a combination of vildagliptin or a pharmaceutically acceptable salt thereof, and metformin or a pharmaceutically acceptable salt thereof.

In one aspect, the invention relates to a method of delaying loss of glycaemic control in a patient with type 2 diabetes mellitus, wherein the method comprises administering to the patient a combination of a DPP-IV inhibitor (preferably vildagliptin or a pharmaceutically acceptable salt thereof), and metformin or a pharmaceutically acceptable salt thereof.

In one aspect, the invention relates to a method of delaying loss of glycaemic control in a patient with type 2 diabetes mellitus, wherein the loss of glycaemic control is delayed relative to metformin monotherapy followed by subsequent co-administration of a DPP-IV inhibitor (preferably vildagliptin or a pharmaceutically acceptable salt thereof) and metformin or a pharmaceutically acceptable salt thereof, wherein the method comprises administering to the patient a combination of a DPP-IV inhibitor (preferably vildagliptin or a pharmaceutically acceptable salt thereof), and metformin or a pharmaceutically acceptable salt thereof.

In one aspect, the invention relates to a method of delaying loss of glycaemic control in a patient with type 2 diabetes mellitus, wherein the loss of glycaemic control is delayed relative to metformin monotherapy, wherein the method comprises administering to the patient a combination of vildagliptin or a pharmaceutically acceptable salt thereof, and metformin or a pharmaceutically acceptable salt thereof.

In one aspect, the invention relates to a method of delaying loss of glycaemic control in a patient with type 2 diabetes mellitus, wherein the loss of glycaemic control is delayed relative to metformin monotherapy followed by subsequent co-administration of a DPP-IV inhibitor (preferably vildagliptin or a pharmaceutically acceptable salt thereof) and metformin or a pharmaceutically acceptable salt thereof, wherein the method comprises administering to the patient a combination of vildagliptin or a pharmaceutically acceptable salt thereof, and metformin or a pharmaceutically acceptable salt thereof.

In one aspect, the invention relates to a method of delaying loss of glycaemic control in a patient with type 2 diabetes mellitus, wherein the loss of glycaemic control is delayed relative to metformin monotherapy, wherein the method comprises administering to the patient a combination of a DPP-IV inhibitor (preferably vildagliptin or a pharmaceutically acceptable salt thereof), and metformin or a pharmaceutically acceptable salt thereof, wherein the patient has not previously received pharmaceutical treatment for the type 2 diabetes mellitus.

In one aspect, the invention relates to a method of delaying loss of glycaemic control in a patient with type 2 diabetes mellitus, wherein the loss of glycaemic control is delayed relative to metformin monotherapy followed by subsequent co-administration of a DPP-IV inhibitor (preferably vildagliptin or a pharmaceutically acceptable salt thereof) and metformin or a pharmaceutically acceptable salt thereof, wherein the method comprises administering to the patient a combination of a DPP-IV inhibitor (preferably vildagliptin or a pharmaceutically acceptable salt thereof), and metformin or a pharmaceutically acceptable salt thereof, wherein the patient has not previously received pharmaceutical treatment for the type 2 diabetes mellitus.

In one aspect, the invention relates to a method of delaying loss of glycaemic control in a patient with type 2 diabetes mellitus, wherein the loss of glycaemic control is delayed relative to metformin monotherapy, wherein the method comprises administering to the patient a combination of vildagliptin or a pharmaceutically acceptable salt thereof, and metformin or a pharmaceutically acceptable salt thereof, and wherein the patient has not previously received pharmaceutical treatment for the type 2 diabetes mellitus.

In one aspect, the invention relates to a method of delaying loss of glycaemic control in a patient with type 2 diabetes mellitus, wherein the loss of glycaemic control is delayed relative to metformin monotherapy followed by subsequent co-administration of a DPP-IV inhibitor (preferably vildagliptin or a pharmaceutically acceptable salt thereof) and metformin or a pharmaceutically acceptable salt thereof, wherein the method comprises administering to the patient a combination of vildagliptin or a pharmaceutically acceptable salt thereof, and metformin or a pharmaceutically acceptable salt thereof, wherein the patient has not previously received pharmaceutical treatment for the type 2 diabetes mellitus.

In another aspect, the invention relates to a method of improving glycaemic control in a patient with type 2 diabetes mellitus, wherein the method comprises administered to the patient a combination of a DPP-IV inhibitor (preferably vildagliptin or a pharmaceutically acceptable salt thereof), and metformin or a pharmaceutically acceptable salt thereof.

In another aspect, the invention relates to a method of improving glycaemic control in a patient with type 2 diabetes mellitus, wherein the improvement in glycaemic control is relative to metformin monotherapy, wherein the method comprises administering to the patient a combination of a DPP-IV inhibitor (preferably vildagliptin or a pharmaceutically acceptable salt thereof), and metformin or a pharmaceutically acceptable salt thereof.

In another aspect, the invention relates to a method of improving glycaemic control in a patient with type 2 diabetes mellitus, wherein the improvement in glycaemic control is relative to metformin monotherapy followed by subsequent co-administration of a DPP-IV inhibitor (preferably vildagliptin or a pharmaceutically acceptable salt thereof) and metformin or a pharmaceutically acceptable salt thereof, wherein the method comprises administering to the patient a combination of a DPP-IV inhibitor (preferably vildagliptin or a pharmaceutically acceptable salt thereof), and metformin or a pharmaceutically acceptable salt thereof.

In another aspect, the invention relates to a method of improving glycaemic control in a patient with type 2 diabetes mellitus, wherein the improvement in glycaemic control is relative to metformin monotherapy, wherein the method comprises administering to the patient a combination of vildagliptin or a pharmaceutically acceptable salt thereof, and metformin or a pharmaceutically acceptable salt thereof.

In another aspect, the invention relates to a method of improving glycaemic control in a patient with type 2 diabetes mellitus, wherein the improvement in glycaemic control is relative to metformin monotherapy followed by subsequent co-administration of a DPP-IV inhibitor (preferably vildagliptin or a pharmaceutically acceptable salt thereof) and metformin or a pharmaceutically acceptable salt thereof, wherein the method comprises administering to the patient a combination of vildagliptin or a pharmaceutically acceptable salt thereof, and metformin or a pharmaceutically acceptable salt thereof.

In another aspect, the invention relates to a method of improving glycaemic control in a patient with type 2 diabetes mellitus, wherein the improvement in glycaemic control is relative to metformin monotherapy, wherein the method comprises administering to the patient a combination of a DPP-IV inhibitor (preferably vildagliptin or a pharmaceutically acceptable salt thereof), and metformin or a pharmaceutically acceptable salt thereof, wherein the patient has not previously received pharmaceutical treatment for the type 2 diabetes mellitus.

In another aspect, the invention relates to a method of improving glycaemic control in a patient with type 2 diabetes mellitus, wherein the improvement in glycaemic control is relative to metformin monotherapy followed by subsequent co-administration of a DPP-IV inhibitor (preferably vildagliptin or a pharmaceutically acceptable salt thereof) and metformin or a pharmaceutically acceptable salt thereof, wherein the method comprises administering to the patient a combination of a DPP-IV inhibitor (preferably vildagliptin or a pharmaceutically acceptable salt thereof), and metformin or a pharmaceutically acceptable salt thereof, wherein the patient has not previously received pharmaceutical treatment for the type 2 diabetes mellitus.

In another aspect, the invention relates to a method of improving glycaemic control in a patient with type 2 diabetes mellitus, wherein the improvement in glycaemic control is relative to metformin monotherapy, wherein the method comprises administering to the patient a combination of vildagliptin or a pharmaceutically acceptable salt thereof, and metformin or a pharmaceutically acceptable salt thereof, wherein the patient has not previously received pharmaceutical treatment for the type 2 diabetes mellitus.

In another aspect, the invention relates to a method of improving glycaemic control in a patient with type 2 diabetes mellitus, wherein the improvement in glycaemic control is relative to metformin monotherapy followed by subsequent co-administration of a DPP-IV inhibitor (preferably vildagliptin or a pharmaceutically acceptable salt thereof) and metformin or a pharmaceutically acceptable salt thereof, wherein the method comprises administering to the patient a combination of vildagliptin or a pharmaceutically acceptable salt thereof, and metformin or a pharmaceutically acceptable salt thereof, wherein the patient has not previously received pharmaceutical treatment for the type 2 diabetes mellitus.

In another aspect, the invention relates to a method of improving glycaemic control in a patient with type 2 diabetes mellitus, wherein the method comprises administering to the patient a combination of a DPP-IV inhibitor (preferably vildagliptin or a pharmaceutically acceptable salt thereof), and metformin or a pharmaceutically acceptable salt thereof, wherein the patient has not previously received pharmaceutical treatment for the type 2 diabetes mellitus.

In another aspect, the invention relates to a method of improving glycaemic control in a patient with type 2 diabetes mellitus, wherein the method comprises administering to the patient a combination of vildagliptin or a pharmaceutically acceptable salt thereof, and metformin or a pharmaceutically acceptable salt thereof, wherein the patient has not previously received pharmaceutical treatment for the type 2 diabetes mellitus.

In another aspect, the invention relates to a method of delaying the increase of $HbA_{1c}$ to greater than or equal to 53 mmol/mol (7.0%) in a patient with type 2 diabetes mellitus, wherein the method comprises administering to the patient a combination of a DPP-IV inhibitor (preferably vildagliptin or a pharmaceutically acceptable salt thereof), and metformin or a pharmaceutically acceptable salt thereof.

In another aspect, the invention relates to a method of delaying the increase of $HbA_{1c}$ to greater than or equal to 53 mmol/mol (7.0%) in a patient with type 2 diabetes mellitus, wherein the delay in the increase of $HbA_{1c}$ is relative to metformin monotherapy, wherein the method comprises administering to the patient a combination of a DPP-IV inhibitor (preferably vildagliptin or a pharmaceutically acceptable salt thereof), and metformin or a pharmaceutically acceptable salt thereof.

In another aspect, the invention relates to a method of delaying the increase of $HbA_{1c}$ to greater than or equal to 53 mmol/mol (7.0%) in a patient with type 2 diabetes mellitus, wherein the delay in the increase of $HbA_{1c}$ is relative to metformin monotherapy followed by subsequent co-administration of a DPP-IV inhibitor (preferably vildagliptin or a pharmaceutically acceptable salt thereof) and metformin, wherein the method comprises administering to the patient a combination of a DPP-IV inhibitor (preferably vildagliptin or a pharmaceutically acceptable salt thereof), and metformin or a pharmaceutically acceptable salt thereof.

In another aspect, the invention relates to a method of delaying the increase of $HbA_{1c}$ to greater than or equal to 53 mmol/mol (7.0%) in a patient with type 2 diabetes mellitus, wherein the delay in the increase of $HbA_{1c}$ is relative to metformin monotherapy, wherein the method comprises administering to the patient a combination of vildagliptin or a pharmaceutically acceptable salt thereof, and metformin or a pharmaceutically acceptable salt thereof.

In another aspect, the invention relates to a method of delaying the increase of $HbA_{1c}$ to greater than or equal to 53 mmol/mol (7.0%) in a patient with type 2 diabetes mellitus, wherein the delay in the increase of $HbA_{1c}$ is relative to metformin monotherapy followed by subsequent co-administration of a DPP-IV inhibitor (preferably vildagliptin or a pharmaceutically acceptable salt thereof) and metformin or a pharmaceutically acceptable salt thereof, wherein the method comprises administering to the patient a combination of vildagliptin or a pharmaceutically acceptable salt thereof, and metformin or a pharmaceutically acceptable salt thereof.

In another aspect, the invention relates to a method of delaying the increase of $HbA_{1c}$ to greater than or equal to 53 mmol/mol (7.0%) in a patient with type 2 diabetes mellitus, wherein the delay in the increase of $HbA_{1c}$ is relative to metformin monotherapy, wherein the method comprises administering to the patient a combination of a DPP-IV inhibitor (preferably vildagliptin or a pharmaceutically acceptable salt thereof), and metformin or a pharmaceutically acceptable salt thereof, wherein the patient has not previously received pharmaceutical treatment for the type 2 diabetes mellitus.

In another aspect, the invention relates to a method of delaying the increase of $HbA_{1c}$ to greater than or equal to 53 mmol/mol (7.0%) in a patient with type 2 diabetes mellitus, wherein the delay in the increase of $HbA_{1c}$ is relative to metformin monotherapy followed by subsequent co-administration of a DPP-IV inhibitor (preferably vildagliptin or a pharmaceutically acceptable salt thereof) and metformin or a pharmaceutically acceptable salt thereof, wherein the method comprises administering to the patient a combination of a DPP-IV inhibitor (preferably vildagliptin or a pharmaceutically acceptable salt thereof), and metformin or a pharmaceutically acceptable salt thereof, wherein the patient has not previously received pharmaceutical treatment for the type 2 diabetes mellitus.

In another aspect, the invention relates to a method of delaying the increase of $HbA_{1c}$ to greater than or equal to 53 mmol/mol (7.0%) in a patient with type 2 diabetes mellitus, wherein the delay in the increase of $HbA_{1c}$ is relative to metformin monotherapy, wherein the method comprises administering to the patient a combination of vildagliptin or a pharmaceutically acceptable salt thereof, and metformin or a pharmaceutically acceptable salt thereof, wherein the patient has not previously received pharmaceutical treatment for the type 2 diabetes mellitus.

In another aspect, the invention relates to a method of delaying the increase of $HbA_{1c}$ to greater than or equal to 53 mmol/mol (7.0%) in a patient with type 2 diabetes mellitus, wherein the delay in the increase of $HbA_{1c}$ is relative to metformin monotherapy followed by subsequent co-administration of a DPP-IV inhibitor (preferably vildagliptin or a pharmaceutically acceptable salt thereof) and metformin or a pharmaceutically acceptable salt thereof, wherein the method comprises administering to the patient a combination of vildagliptin or a pharmaceutically acceptable salt thereof, and metformin or a pharmaceutically acceptable salt thereof, wherein the patient has not previously received pharmaceutical treatment for the type 2 diabetes mellitus.

In another aspect, the invention relates to a method of delaying the increase of $HbA_{1c}$ to greater than or equal to 53 mmol/mol (7.0%) in a patient with type 2 diabetes mellitus, wherein the method comprises administering to the patient a combination of a DPP-IV inhibitor (preferably vildagliptin or a pharmaceutically acceptable salt thereof), and metformin or a pharmaceutically acceptable salt thereof, wherein the patient has not previously received pharmaceutical treatment for the type 2 diabetes mellitus.

In another aspect, the invention relates to a method of delaying the increase of $HbA_{1c}$ to greater than or equal to 53 mmol/mol (7.0%) in a patient with type 2 diabetes mellitus, wherein the method comprises administering to the patient a combination of vildagliptin or a pharmaceutically acceptable salt thereof, and metformin or a pharmaceutically acceptable salt thereof, wherein the patient has not previously received pharmaceutical treatment for the type 2 diabetes mellitus.

In another aspect, the invention relates to a method of increasing the time taken to reach an $HbA_{1c}$ measurement of greater than or equal to 53 mmol/mol (7.0%) in a patient with type 2 diabetes mellitus, wherein the method comprises administering to the patient a combination of a DPP-IV inhibitor (preferably vildagliptin or a pharmaceutically acceptable salt thereof), and metformin or a pharmaceutically acceptable salt thereof.

In another aspect, the invention relates to a method of increasing the time taken to reach an $HbA_{1c}$ measurement of greater than or equal to 53 mmol/mol (7.0%) in a patient with type 2 diabetes mellitus, wherein the increase is relative to metformin monotherapy, wherein the method comprises administering to the patient a combination of a DPP-IV inhibitor (preferably vildagliptin or a pharmaceutically acceptable salt thereof), and metformin or a pharmaceutically acceptable salt thereof.

In another aspect, the invention relates to a method of increasing the time taken to reach an $HbA_{1c}$ measurement of greater than or equal to 53 mmol/mol (7.0%) in a patient with type 2 diabetes mellitus, wherein the increase is relative to metformin monotherapy followed by subsequent co-administration of a DPP-IV inhibitor (preferably vildagliptin or a pharmaceutically acceptable salt thereof) and metformin or a pharmaceutically acceptable salt thereof, wherein the method comprises administering to the patient a combination of a DPP-IV inhibitor (preferably vildagliptin or a pharmaceutically acceptable salt thereof), and metformin or a pharmaceutically acceptable salt thereof.

In another aspect, the invention relates to a method of increasing the time taken to reach an $HbA_{1c}$ measurement of greater than or equal to 53 mmol/mol (7.0%) in a patient with type 2 diabetes mellitus, wherein the increase is relative to metformin monotherapy, wherein the method comprises administering to the patient a combination of vildagliptin or a pharmaceutically acceptable salt thereof, and metformin or a pharmaceutically acceptable salt thereof.

In another aspect, the invention relates to a method of increasing the time taken to reach an $HbA_{1c}$ measurement of greater than or equal to 53 mmol/mol (7.0%) in a patient with type 2 diabetes mellitus, wherein the increase is relative to metformin monotherapy followed by subsequent co-administration of a DPP-IV inhibitor (preferably vildagliptin or a pharmaceutically acceptable salt thereof) and metformin or a pharmaceutically acceptable salt thereof, wherein the method comprises administering to the patient a combination of vildagliptin or a pharmaceutically acceptable salt thereof, and metformin or a pharmaceutically acceptable salt thereof.

In another aspect, the invention relates to a method of increasing the time taken to reach an $HbA_{1c}$ measurement of greater than or equal to 53 mmol/mol (7.0%) in a patient with type 2 diabetes mellitus, wherein the increase is relative to metformin monotherapy, wherein the method comprises administering to the patient a combination of a DPP-IV inhibitor (preferably vildagliptin or a pharmaceutically acceptable salt thereof), and metformin or a pharmaceutically acceptable salt thereof, wherein the patient has not previously received pharmaceutical treatment for the type 2 diabetes mellitus.

In another aspect, the invention relates to a method of method of increasing the time taken to reach an $HbA_{1c}$ measurement of greater than or equal to 53 mmol/mol (7.0%) in a patient with type 2 diabetes mellitus, wherein the increase is relative to metformin monotherapy followed by subsequent co-administration of a DPP-IV inhibitor (preferably vildagliptin or a pharmaceutically acceptable salt thereof) and metformin or a pharmaceutically acceptable salt thereof, wherein the method comprises administering to the patient a combination of a DPP-IV inhibitor (preferably vildagliptin or a pharmaceutically acceptable salt thereof), and metformin or a pharmaceutically acceptable salt thereof, wherein the patient has not previously received pharmaceutical treatment for the type 2 diabetes mellitus.

In another aspect, the invention relates to a method of increasing the time taken to reach an $HbA_{1c}$ measurement of greater than or equal to 53 mmol/mol (7.0%) in a patient with type 2 diabetes mellitus, wherein the increase is relative to metformin monotherapy, wherein the method comprises administering to the patient a combination of vildagliptin or a pharmaceutically acceptable salt thereof, and metformin or a pharmaceutically acceptable salt thereof, wherein the patient has not previously received pharmaceutical treatment for the type 2 diabetes mellitus.

In another aspect, the invention relates to a method of increasing the time taken to reach an $HbA_{1c}$ measurement of greater than or equal to 53 mmol/mol (7.0%) in a patient with type 2 diabetes mellitus, wherein the increase is relative to metformin monotherapy followed by subsequent co-administration of a DPP-IV inhibitor (preferably vildagliptin or a pharmaceutically acceptable salt thereof) and metformin or a pharmaceutically acceptable salt thereof, wherein the method comprises administering to the patient a combination of vildagliptin or a pharmaceutically acceptable salt thereof, and metformin or a pharmaceutically acceptable salt thereof, wherein the patient has not previously received pharmaceutical treatment for the type 2 diabetes mellitus.

In another aspect, the invention relates to a method of increasing the time taken to reach an $HbA_{1c}$ measurement of greater than or equal to 53 mmol/mol (7.0%) in a patient with type 2 diabetes mellitus, wherein the method comprises administering to the patient a combination of a DPP-IV inhibitor (preferably vildagliptin or a pharmaceutically acceptable salt thereof), and metformin or a pharmaceutically acceptable salt thereof, wherein the patient has not previously received pharmaceutical treatment for the type 2 diabetes mellitus.

In another aspect, the invention relates to a method of increasing the time taken to reach an $HbA_{1c}$ measurement of greater than or equal to 53 mmol/mol (7.0%) in a patient with type 2 diabetes mellitus, wherein the method comprises administering to the patient a combination of vildagliptin or a pharmaceutically acceptable salt thereof, and metformin or a pharmaceutically acceptable salt thereof, wherein the patient has not previously received pharmaceutical treatment for the type 2 diabetes mellitus.

In another aspect, the invention relates to a method of preventing loss of glycaemic control in a patient with type 2 diabetes mellitus, wherein the method comprises administering to the patient a combination of a DPP-IV inhibitor (preferably vildagliptin or a pharmaceutically acceptable salt thereof), and metformin or a pharmaceutically acceptable salt thereof.

In another aspect, the invention relates to a method of preventing loss of glycaemic control in a patient with type 2 diabetes mellitus, wherein the method comprises administering to the patient a combination of vildagliptin or a pharmaceutically acceptable salt thereof, and metformin or a pharmaceutically acceptable salt thereof.

In another aspect, the invention relates to a method of preventing loss of glycaemic control in a patient with type 2 diabetes mellitus, wherein the method comprises administering to the patient a combination of a DPP-IV inhibitor (preferably vildagliptin or a pharmaceutically acceptable salt thereof), and metformin or a pharmaceutically acceptable salt thereof, wherein the patient has not previously received pharmaceutical treatment for the type 2 diabetes mellitus.

In another aspect, the invention relates to a method of preventing loss of glycaemic control in a patient with type 2 diabetes mellitus, wherein the method comprises administering to the patient a combination of vildagliptin or a pharmaceutically acceptable salt thereof, and metformin or a pharmaceutically acceptable salt thereof, wherein the patient has not previously received pharmaceutical treatment for the type 2 diabetes mellitus.

In another aspect, the invention relates to a method of reducing the risk of a cardiovascular event in a patient undergoing treatment for type 2 diabetes mellitus, wherein the method comprises administering to the patient a combination of a DPP-IV inhibitor (preferably vildagliptin or a pharmaceutically acceptable salt thereof), and metformin or a pharmaceutically acceptable salt thereof.

In another aspect, the invention relates to a method of reducing the risk of a cardiovascular event in a patient undergoing treatment for type 2 diabetes mellitus, wherein the method comprises administering to the patient a combination of vildagliptin or a pharmaceutically acceptable salt thereof, and metformin or a pharmaceutically acceptable salt thereof.

In another aspect, the invention relates to a method of reducing the risk of a cardiovascular event in a patient undergoing treatment for type 2 diabetes mellitus, wherein the method comprises administering to the patient a combination of a DPP-IV inhibitor (preferably vildagliptin or a pharmaceutically acceptable salt thereof), and metformin or a pharmaceutically acceptable salt thereof, wherein the patient has not previously received pharmaceutical treatment for the type 2 diabetes mellitus.

In another aspect, the invention relates to a method of reducing the risk of a cardiovascular event in a patient undergoing treatment for type 2 diabetes mellitus, wherein the method comprises administering to the patient a combination of vildagliptin or a pharmaceutically acceptable salt thereof and metformin or a pharmaceutically acceptable salt thereof, wherein the patient has not previously received pharmaceutical treatment for the type 2 diabetes mellitus.

In another aspect, the invention relates to a method of reducing the risk of a cardiovascular event in a patient undergoing treatment for type 2 diabetes mellitus, wherein the method comprises administering to the patient a combination of a DPP-IV inhibitor (vildagliptin or a pharmaceutically acceptable salt thereof), and metformin or a pharmaceutically acceptable salt thereof, wherein the risk is reduced relative to metformin monotherapy.

In another aspect, the invention relates to a method of reducing the risk of a cardiovascular event in a patient undergoing treatment for type 2 diabetes mellitus, wherein the risk is reduced relative to metformin monotherapy followed by subsequent co-administration of a DPP-IV inhibitor (preferably vildagliptin or a pharmaceutically acceptable salt thereof) and metformin or a pharmaceutically acceptable salt thereof, wherein the method comprises administering to the patient a combination of a DPP-IV inhibitor (preferably vildagliptin or a pharmaceutically acceptable salt thereof), and metformin or a pharmaceutically acceptable salt thereof.

In another aspect, the invention relates to a method of reducing the risk of a cardiovascular event in a patient undergoing treatment for type 2 diabetes mellitus, wherein the risk is reduced relative to metformin monotherapy, wherein the method comprises administering to the patient a combination of vildagliptin or a pharmaceutically acceptable salt thereof, and metformin or a pharmaceutically acceptable salt thereof, wherein the risk is reduced relative to metformin monotherapy.

In another aspect, the invention relates to a method of reducing the risk of a cardiovascular event in a patient undergoing treatment for type 2 diabetes mellitus, wherein the risk is reduced relative to metformin monotherapy followed by subsequent co-administration of a DPP-IV inhibitor (preferably vildagliptin or a pharmaceutically acceptable salt thereof) and metformin or a pharmaceutically acceptable salt thereof, wherein the method comprises administering to the patient a combination of vildagliptin or a pharmaceutically acceptable salt thereof, and metformin or a pharmaceutically acceptable salt thereof.

In another aspect, the invention relates to a method of reducing the risk of a cardiovascular event in a patient undergoing treatment for type 2 diabetes mellitus, wherein the risk is reduced relative to metformin monotherapy, wherein the method comprises administering to the patient a combination of a DPP-IV inhibitor (vildagliptin or a pharmaceutically acceptable salt thereof), and metformin or a pharmaceutically acceptable salt thereof, wherein the patient has not previously received pharmaceutical treatment for the type 2 diabetes mellitus.

In another aspect, the invention relates to a method of reducing the risk of a cardiovascular event in a patient undergoing treatment for type 2 diabetes mellitus, wherein the risk is reduced relative to metformin monotherapy followed by subsequent co-administration of a DPP-IV inhibitor (preferably vildagliptin or a pharmaceutically acceptable salt thereof) and metformin or a pharmaceutically acceptable salt thereof, wherein the method comprises administering to the patient a combination of a DPP-IV inhibitor (preferably vildagliptin or a pharmaceutically acceptable salt thereof), and metformin or a pharmaceutically acceptable salt thereof, wherein the patient has not previously received pharmaceutical treatment for the type 2 diabetes mellitus.

In another aspect, the invention relates to a method of reducing the risk of a cardiovascular event in a patient undergoing treatment for type 2 diabetes mellitus, wherein the risk is reduced relative to metformin monotherapy, wherein the method comprises administering to the patient a combination of vildagliptin or a pharmaceutically acceptable salt thereof, and metformin or a pharmaceutically acceptable salt thereof, wherein the patient has not previously received pharmaceutical treatment for the type 2 diabetes mellitus.

In another aspect, the invention relates to a method of reducing the risk of a cardiovascular event in a patient undergoing treatment for type 2 diabetes mellitus, wherein the risk is reduced relative to metformin monotherapy followed by subsequent co-administration of a DPP-IV inhibitor (preferably vildagliptin or a pharmaceutically acceptable salt thereof) and metformin or a pharmaceutically acceptable salt thereof, wherein the method comprises administering to the patient a combination of vildagliptin or a pharmaceutically acceptable salt thereof, and metformin or a pharmaceutically acceptable salt thereof, wherein the patient has not previously received pharmaceutical treatment for the type 2 diabetes mellitus.

In another aspect, the invention relates to a method of treating type 2 diabetes mellitus without concomitant administration of insulin, wherein the method comprises administering to the patient a combination of a DPP-IV inhibitor (preferably vildagliptin or a pharmaceutically acceptable salt thereof), and metformin or a pharmaceutically acceptable salt thereof.

In another aspect, the invention relates to a method of treating type 2 diabetes mellitus without concomitant administration of insulin, wherein the method comprises administering to the patient a combination of vildagliptin or a pharmaceutically acceptable salt thereof, and metformin or a pharmaceutically acceptable salt thereof.

In another aspect, the invention relates to a method of treating type 2 diabetes mellitus without concomitant administration of insulin, wherein the method comprises administering to the patient a combination of a DPP-IV inhibitor (preferably vildagliptin or a pharmaceutically acceptable salt thereof), and metformin or a pharmaceutically acceptable salt thereof, wherein the patient has not previously received pharmaceutical treatment for the type 2 diabetes mellitus.

In another aspect, the invention relates to a method of treating type 2 diabetes mellitus without concomitant administration of insulin, wherein the method comprises administering to the patient a combination of vildagliptin or a pharmaceutically acceptable salt thereof, and metformin or a pharmaceutically acceptable salt thereof, wherein the patient has not previously received pharmaceutical treatment for the type 2 diabetes mellitus.

Uses

In one aspect, the invention relates to the use of a combination of a DPP-IV inhibitor (preferably vildagliptin or a pharmaceutically acceptable salt thereof), and metformin or a pharmaceutically acceptable salt thereof, in the manufacture of a medicament for delaying loss of glycaemic control in a patient with type 2 diabetes mellitus.

In one aspect, the invention relates to the use of a combination of a vildagliptin or a pharmaceutically acceptable salt thereof and metformin or a pharmaceutically acceptable salt thereof, in the manufacture of a medicament for delaying loss of glycaemic control in a patient with type 2 diabetes mellitus.

In one aspect, the invention relates to the use of a combination of a DPP-IV inhibitor (preferably vildagliptin or a pharmaceutically acceptable salt thereof), and metformin or a pharmaceutically acceptable salt thereof, in the manufacture of a medicament for delaying loss of glycaemic control in a patient with type 2 diabetes mellitus, wherein the patient has not previously received pharmaceutical treatment for the type 2 diabetes mellitus.

In one aspect, the invention relates to the use of a combination of vildagliptin or a pharmaceutically acceptable salt thereof, and metformin or a pharmaceutically acceptable salt thereof, in the manufacture of a medicament for delaying loss of glycaemic control in a patient with type 2 diabetes mellitus, wherein the patient has not previously received pharmaceutical treatment for the type 2 diabetes mellitus.

In one aspect, the invention relates to the use of a combination of a DPP-IV inhibitor (preferably vildagliptin or a pharmaceutically acceptable salt thereof), and metformin or a pharmaceutically acceptable salt thereof, in the manufacture of a medicament for delaying loss of glycaemic control in a patient with type 2 diabetes mellitus, wherein the loss of glycaemic control is delayed relative to metformin monotherapy.

In one aspect, the invention relates to the use of a combination of a DPP-IV inhibitor (preferably vildagliptin or a pharmaceutically acceptable salt thereof), and metformin or a pharmaceutically acceptable salt thereof, in the manufacture of a medicament for delaying loss of glycaemic control in a patient with type 2 diabetes mellitus, wherein the loss of glycaemic control is delayed relative to metformin monotherapy followed by subsequent co-administration of a DPP-IV inhibitor (preferably vildagliptin or a pharmaceutically acceptable salt thereof) and metformin or a pharmaceutically acceptable salt thereof.

In one aspect, the invention relates to the use of a combination of vildagliptin or a pharmaceutically acceptable salt thereof, and metformin or a pharmaceutically acceptable salt thereof, in the manufacture of a medicament for delaying loss of glycaemic control in a patient with type 2 diabetes mellitus, wherein the loss of glycaemic control is delayed relative to metformin monotherapy.

In one aspect, the invention relates to the use of a combination of vildagliptin or a pharmaceutically acceptable salt thereof, and metformin or a pharmaceutically acceptable salt thereof, in the manufacture of a medicament for delaying loss of glycaemic control in a patient with type 2 diabetes mellitus, wherein the loss of glycaemic control is delayed relative to metformin monotherapy followed by subsequent co-administration of a DPP-IV inhibitor (preferably vildagliptin or a pharmaceutically acceptable salt thereof) and metformin or a pharmaceutically acceptable salt thereof.

In one aspect, the invention relates to the use of a combination of a DPP-IV inhibitor (preferably vildagliptin or a pharmaceutically acceptable salt thereof), and metformin or a pharmaceutically acceptable salt thereof, in the manufacture of a medicament for delaying loss of glycaemic control in a patient with type 2 diabetes mellitus, wherein the loss of glycaemic control is delayed relative to metformin monotherapy, and wherein the patient has not previously received pharmaceutical treatment for the type 2 diabetes mellitus.

In one aspect, the invention relates to the use of a combination of a DPP-IV inhibitor (preferably vildagliptin or a pharmaceutically acceptable salt thereof), and metformin or a pharmaceutically acceptable salt thereof, in the manufacture of a medicament for delaying loss of glycaemic control in a patient with type 2 diabetes mellitus, wherein the loss of glycaemic control is delayed relative to metformin monotherapy followed by subsequent co-administration of a DPP-IV inhibitor (preferably vildagliptin or a pharmaceutically acceptable salt thereof) and metformin or a pharmaceutically acceptable salt thereof, and wherein the patient has not previously received pharmaceutical treatment for the type 2 diabetes mellitus.

In one aspect, the invention relates to the use of a combination of vildagliptin or a pharmaceutically acceptable salt thereof, and metformin or a pharmaceutically acceptable salt thereof, in the manufacture of a medicament for delaying loss of glycaemic control in a patient with type 2 diabetes mellitus, wherein the loss of glycaemic control is delayed relative to metformin monotherapy, and wherein the patient has not previously received pharmaceutical treatment for the type 2 diabetes mellitus.

In one aspect, the invention relates to the use of a combination of vildagliptin or a pharmaceutically acceptable salt thereof, and metformin or a pharmaceutically acceptable salt thereof, in the manufacture of a medicament for delaying loss of glycaemic control in a patient with type 2 diabetes mellitus, wherein the loss of glycaemic control is delayed relative to metformin monotherapy followed by subsequent co-administration of a DPP-IV inhibitor (preferably vildagliptin or a pharmaceutically acceptable salt thereof) and metformin or a pharmaceutically acceptable salt thereof, and wherein the patient has not previously received pharmaceutical treatment for the type 2 diabetes mellitus.

In another aspect, the invention relates to the use of a combination of a DPP-IV inhibitor (preferably vildagliptin or a pharmaceutically acceptable salt thereof), and metformin or a pharmaceutically acceptable salt thereof, in the manufacture of a medicament for improving glycaemic control in a patient with type 2 diabetes mellitus.

In another aspect, the invention relates to the use of a combination of a DPP-IV inhibitor (preferably vildagliptin or a pharmaceutically acceptable salt thereof), and metformin or a pharmaceutically acceptable salt thereof, in the manufacture of a medicament for improving glycaemic control in a patient with type 2 diabetes mellitus, wherein the improvement in glycaemic control is relative to metformin monotherapy followed by subsequent co-administration of a DPP-IV inhibitor (preferably vildagliptin or a pharmaceutically acceptable salt thereof) and metformin or a pharmaceutically acceptable salt thereof.

In another aspect, the invention relates to the use of a combination of vildagliptin or a pharmaceutically acceptable salt thereof, and metformin or a pharmaceutically acceptable salt thereof, in the manufacture of a medicament for improving glycaemic control in a patient with type 2 diabetes mellitus, wherein the improvement in glycaemic control is relative to metformin monotherapy.

In another aspect, the invention relates to the use of a combination of vildagliptin or a pharmaceutically acceptable salt thereof, and metformin or a pharmaceutically acceptable salt thereof, in the manufacture of a medicament for improving glycaemic control in a patient with type 2 diabetes mellitus, wherein the improvement in glycaemic control is relative to metformin monotherapy followed by subsequent co-administration of a DPP-IV inhibitor (preferably vildagliptin or a pharmaceutically acceptable salt thereof) and metformin or a pharmaceutically acceptable salt thereof.

In another aspect, the invention relates to the use of a combination of a DPP-IV inhibitor (preferably vildagliptin or a pharmaceutically acceptable salt thereof), and metformin or a pharmaceutically acceptable salt thereof, in the manufacture of a medicament for improving glycaemic control in a patient with type 2 diabetes mellitus, wherein the improvement in glycaemic control is relative to metformin monotherapy, and wherein the patient has not previously received pharmaceutical treatment for the type 2 diabetes mellitus.

In another aspect, the invention relates to the use of a combination of a DPP-IV inhibitor (preferably vildagliptin or a pharmaceutically acceptable salt thereof), and metformin or a pharmaceutically acceptable salt thereof, in the manufacture of a medicament for improving glycaemic control in a patient with type 2 diabetes mellitus, wherein the improvement in glycaemic control is relative to metformin monotherapy followed by subsequent co-administration of a DPP-IV inhibitor (preferably vildagliptin or a pharmaceutically acceptable salt thereof) and metformin or a pharmaceutically acceptable salt thereof, and wherein the patient has not previously received pharmaceutical treatment for the type 2 diabetes mellitus.

In another aspect, the invention relates to the use of a combination of vildagliptin or a pharmaceutically acceptable salt thereof, and metformin or a pharmaceutically acceptable salt thereof, in the manufacture of a medicament for improving glycaemic control in a patient with type 2 diabetes mellitus, wherein the improvement in glycaemic control is relative to metformin monotherapy, and wherein the patient has not previously received pharmaceutical treatment for the type 2 diabetes mellitus.

In another aspect, the invention relates to the use of a combination of vildagliptin or a pharmaceutically acceptable salt thereof, and metformin or a pharmaceutically acceptable salt thereof, in the manufacture of a medicament for improving glycaemic control in a patient with type 2 diabetes mellitus, wherein the improvement in glycaemic control is relative to metformin monotherapy followed by subsequent co-administration of a DPP-IV inhibitor (preferably vildagliptin or a pharmaceutically acceptable salt thereof) and metformin or a pharmaceutically acceptable salt thereof, and wherein the patient has not previously received pharmaceutical treatment for the type 2 diabetes mellitus.

In another aspect, the invention relates to the use of a combination of a DPP-IV inhibitor (preferably vildagliptin or a pharmaceutically acceptable salt thereof), and metformin or a pharmaceutically acceptable salt thereof, in the manufacture of a medicament for improving glycaemic control in a patient with type 2 diabetes mellitus, wherein the patient has not previously received pharmaceutical treatment for the type 2 diabetes mellitus.

In another aspect, the invention relates to the use of a combination of vildagliptin or a pharmaceutically acceptable salt thereof, and metformin or a pharmaceutically acceptable salt thereof, in the manufacture of a medicament for improving glycaemic control in a patient with type 2 diabetes mellitus, wherein the patient has not previously received pharmaceutical treatment for the type 2 diabetes mellitus.

In another aspect, the invention relates to the use of a combination of a DPP-IV inhibitor (preferably vildagliptin or a pharmaceutically acceptable salt thereof), and metformin or a pharmaceutically acceptable salt thereof, in the manufacture of a medicament for delaying the increase of $HbA_{1c}$ to greater than or equal to 53 mmol/mol (7.0%) in a patient with type 2 diabetes mellitus.

In another aspect, the invention relates to the use of a combination of a DPP-IV inhibitor (preferably vildagliptin or a pharmaceutically acceptable salt thereof), and metformin or a pharmaceutically acceptable salt thereof, in the manufacture of a medicament for delaying the increase of $HbA_{1c}$ to greater than or equal to 53 mmol/mol (7.0%) in a patient with type 2 diabetes mellitus, wherein the delay in the increase of $HbA_{1c}$ is relative to metformin monotherapy.

In another aspect, the invention relates to the use of a combination of a DPP-IV inhibitor (preferably vildagliptin or a pharmaceutically acceptable salt thereof), and metformin or a pharmaceutically acceptable salt thereof, in the manufacture of a medicament for delaying the increase of $HbA_{1c}$ to greater than or equal to 53 mmol/mol (7.0%) in a patient with type 2 diabetes mellitus, wherein the delay in the increase of $HbA_{1c}$ is relative to metformin monotherapy followed by subsequent co-administration of a DPP-IV inhibitor (preferably vildagliptin or a pharmaceutically acceptable salt thereof) and metformin.

In another aspect, the invention relates to the use of a combination of vildagliptin or a pharmaceutically acceptable salt thereof, and metformin or a pharmaceutically acceptable salt thereof, in the manufacture of a medicament for delaying the increase of $HbA_{1c}$ to greater than or equal to 53 mmol/mol (7.0%) in a patient with type 2 diabetes mellitus, wherein the delay in the increase of $HbA_{1c}$ is relative to metformin monotherapy.

In another aspect, the invention relates to the use of a combination of vildagliptin or a pharmaceutically acceptable salt thereof, and metformin or a pharmaceutically acceptable salt thereof, in the manufacture of a medicament for delaying the increase of $HbA_{1c}$ to greater than or equal to 53 mmol/mol (7.0%) in a patient with type 2 diabetes mellitus, wherein the delay in the increase of $HbA_{1c}$ is relative to metformin monotherapy followed by subsequent co-administration of a DPP-IV inhibitor (preferably vildagliptin or a pharmaceutically acceptable salt thereof) and metformin or a pharmaceutically acceptable salt thereof.

In another aspect, the invention relates to the use of a combination of a DPP-IV inhibitor (preferably vildagliptin or a pharmaceutically acceptable salt thereof), and metformin or a pharmaceutically acceptable salt thereof, in the manufacture of a medicament for delaying the increase of $HbA_{1c}$ to greater than or equal to 53 mmol/mol (7.0%) in a patient with type 2 diabetes mellitus, wherein the delay in the increase of $HbA_{1c}$ is relative to metformin monotherapy, and wherein the patient has not previously received pharmaceutical treatment for the type 2 diabetes mellitus.

In another aspect, the invention relates to the use of a combination of a DPP-IV inhibitor (preferably vildagliptin or a pharmaceutically acceptable salt thereof), and metformin or a pharmaceutically acceptable salt thereof, in the manufacture of a medicament for delaying the increase of $HbA_{1c}$ to greater than or equal to 53 mmol/mol (7.0%) in a patient with type 2 diabetes mellitus, wherein the delay in the increase of $HbA_{1c}$ is relative to metformin monotherapy followed by subsequent co-administration of a DPP-IV inhibitor (preferably vildagliptin or a pharmaceutically acceptable salt thereof) and metformin or a pharmaceutically acceptable salt thereof, and wherein the patient has not previously received pharmaceutical treatment for the type 2 diabetes mellitus.

In another aspect, the invention relates to the use of a combination of vildagliptin or a pharmaceutically acceptable salt thereof, and metformin or a pharmaceutically acceptable salt thereof, in the manufacture of a medicament for delaying the increase of $HbA_{1c}$ to greater than or equal to 53 mmol/mol (7.0%) in a patient with type 2 diabetes mellitus, wherein the delay in the increase of $HbA_{1c}$ is relative to metformin monotherapy, and wherein the patient has not previously received pharmaceutical treatment for the type 2 diabetes mellitus.

In another aspect, the invention relates to the use of a combination of vildagliptin or a pharmaceutically acceptable salt thereof, and metformin or a pharmaceutically acceptable salt thereof, in the manufacture of a medicament for delaying the increase of $HbA_{1c}$ to greater than or equal to 53 mmol/mol (7.0%) in a patient with type 2 diabetes mellitus, wherein the delay in the increase of $HbA_{1c}$ is relative to metformin monotherapy followed by subsequent co-administration of a DPP-IV inhibitor (preferably vildagliptin or a pharmaceutically acceptable salt thereof) and metformin or a pharmaceutically acceptable salt thereof, and wherein the patient has not previously received pharmaceutical treatment for the type 2 diabetes mellitus.

In another aspect, the invention relates to the use of a combination of a DPP-IV inhibitor (preferably vildagliptin or a pharmaceutically acceptable salt thereof), and metformin or a pharmaceutically acceptable salt thereof, in the manufacture of a medicament for delaying the increase of $HbA_{1c}$ to greater than or equal to 53 mmol/mol (7.0%) in a patient with type 2 diabetes mellitus, wherein the patient has not previously received pharmaceutical treatment for the type 2 diabetes mellitus.

In another aspect, the invention relates to the use of a combination of vildagliptin or a pharmaceutically acceptable salt thereof, and metformin or a pharmaceutically acceptable salt thereof, in the manufacture of a medicament for delaying the increase of $HbA_{1c}$ to greater than or equal to 53 mmol/mol (7.0%) in a patient with type 2 diabetes mellitus, wherein the patient has not previously received pharmaceutical treatment for the type 2 diabetes mellitus.

In another aspect, the invention relates to the use of a combination of a DPP-IV inhibitor (preferably vildagliptin or a pharmaceutically acceptable salt thereof), and metformin or a pharmaceutically acceptable salt thereof, in the manufacture of a medicament for increasing the time taken to reach an $HbA_{1c}$ measurement of greater than or equal to 53 mmol/mol (7.0%) in a patient with type 2 diabetes mellitus.

In another aspect, the invention relates to the use of a combination of a DPP-IV inhibitor (preferably vildagliptin or a pharmaceutically acceptable salt thereof), and metformin or a pharmaceutically acceptable salt thereof, in the manufacture of a medicament for increasing the time taken to reach an $HbA_{1c}$ measurement of greater than or equal to 53 mmol/mol (7.0%) in a patient with type 2 diabetes mellitus, wherein the increase is relative to metformin monotherapy.

In another aspect, the invention relates to the use of a combination of a DPP-IV inhibitor (preferably vildagliptin or a pharmaceutically acceptable salt thereof), and metformin or a pharmaceutically acceptable salt thereof, in the manufacture of a medicament for increasing the time taken to reach an $HbA_{1c}$ measurement of greater than or equal to 53 mmol/mol (7.0%) in a patient with type 2 diabetes mellitus, wherein the increase is relative to metformin monotherapy followed by subsequent co-administration of a DPP-IV inhibitor (preferably vildagliptin or a pharmaceutically acceptable salt thereof) and metformin or a pharmaceutically acceptable salt thereof.

In another aspect, the invention relates to the use of a combination of vildagliptin or a pharmaceutically acceptable salt thereof, and metformin or a pharmaceutically acceptable salt thereof, in the manufacture of a medicament for increasing the time taken to reach an $HbA_{1c}$ measurement of greater than or equal to 53 mmol/mol (7.0%) in a patient with type 2 diabetes mellitus, wherein the increase is relative to metformin monotherapy.

In another aspect, the invention relates to the use of a combination of vildagliptin or a pharmaceutically acceptable salt thereof, and metformin or a pharmaceutically acceptable salt thereof, in the manufacture of a medicament for increasing the time taken to reach an $HbA_{1c}$ measurement of greater than or equal to 53 mmol/mol (7.0%) in a patient with type 2 diabetes mellitus, wherein the increase is relative to metformin monotherapy followed by subsequent co-administration of a DPP-IV inhibitor (preferably vildagliptin or a pharmaceutically acceptable salt thereof) and metformin or a pharmaceutically acceptable salt thereof.

In another aspect, the invention relates to the use of a combination of a DPP-IV inhibitor (preferably vildagliptin or a pharmaceutically acceptable salt thereof), and metformin or a pharmaceutically acceptable salt thereof, in the manufacture of a medicament for increasing the time taken to reach an $HbA_{1c}$ measurement of greater than or equal to 53 mmol/mol (7.0%) in a patient with type 2 diabetes mellitus, wherein the increase is relative to metformin monotherapy, and wherein the patient has not previously received pharmaceutical treatment for the type 2 diabetes mellitus.

In another aspect, the invention relates to the use of a combination of a DPP-IV inhibitor (preferably vildagliptin or a pharmaceutically acceptable salt thereof), and metformin or a pharmaceutically acceptable salt thereof, in the manufacture of a medicament for increasing the time taken to reach an $HbA_{1c}$ measurement of greater than or equal to 53 mmol/mol (7.0%) in a patient with type 2 diabetes mellitus, wherein the increase is relative to metformin monotherapy followed by subsequent co-administration of a DPP-IV inhibitor (preferably vildagliptin or a pharmaceutically acceptable salt thereof) and metformin or a pharmaceutically acceptable salt thereof, and wherein the patient has not previously received pharmaceutical treatment for the type 2 diabetes mellitus.

In another aspect, the invention relates to the use of a combination of vildagliptin or a pharmaceutically acceptable salt thereof, and metformin or a pharmaceutically acceptable salt thereof, in the manufacture of a medicament for increasing the time taken to reach an $HbA_{1c}$ measurement of greater than or equal to 53 mmol/mol (7.0%) in a patient with type 2 diabetes mellitus, wherein the increase is relative to metformin monotherapy, and wherein the patient has not previously received pharmaceutical treatment for the type 2 diabetes mellitus.

In another aspect, the invention relates to the use of a combination of vildagliptin or a pharmaceutically acceptable salt thereof, and metformin or a pharmaceutically acceptable salt thereof, in the manufacture of a medicament for increasing the time taken to reach an $HbA_{1c}$ measurement of greater than or equal to 53 mmol/mol (7.0%) in a patient with type 2 diabetes mellitus, wherein the increase is relative to metformin monotherapy followed by subsequent co-administration of a DPP-IV inhibitor (preferably vildagliptin or a pharmaceutically acceptable salt thereof) and metformin or a pharmaceutically acceptable salt thereof, and wherein the patient has not previously received pharmaceutical treatment for the type 2 diabetes mellitus.

In another aspect, the invention relates to the use of a combination of a DPP-IV inhibitor (preferably vildagliptin or a pharmaceutically acceptable salt thereof), and metformin or a pharmaceutically acceptable salt thereof, in the manufacture of a medicament for increasing the time taken to reach an $HbA_{1c}$ measurement of greater than or equal to 53 mmol/mol (7.0%) in a patient with type 2 diabetes mellitus, wherein the patient has not previously received pharmaceutical treatment for the type 2 diabetes mellitus.

In another aspect, the invention relates to the use of a combination of vildagliptin or a pharmaceutically acceptable salt thereof, and metformin or a pharmaceutically acceptable salt thereof, in the manufacture of a medicament for increasing the time taken to reach an $HbA_{1c}$ measurement of greater than or equal to 53 mmol/mol (7.0%) in a patient with type 2 diabetes mellitus, wherein the patient has not previously received pharmaceutical treatment for the type 2 diabetes mellitus.

In another aspect, the invention relates to the use of a combination of a DPP-IV inhibitor (preferably vildagliptin or a pharmaceutically acceptable salt thereof), and metformin or a pharmaceutically acceptable salt thereof, in the manufacture of a medicament for preventing loss of glycaemic control in a patient with type 2 diabetes mellitus.

In another aspect, the invention relates to the use of a combination of vildagliptin or a pharmaceutically acceptable salt thereof, and metformin or a pharmaceutically acceptable salt thereof, in the manufacture of a medicament for preventing loss of glycaemic control in a patient with type 2 diabetes mellitus.

In another aspect, the invention relates to the use of a combination of a DPP-IV inhibitor (preferably vildagliptin or a pharmaceutically acceptable salt thereof), and metformin or a pharmaceutically acceptable salt thereof, in the manufacture of a medicament for preventing loss of glycaemic control in a patient with type 2 diabetes mellitus, wherein the patient has not previously received pharmaceutical treatment for the type 2 diabetes mellitus.

In another aspect, the invention relates to the use of a combination of vildagliptin or a pharmaceutically acceptable salt thereof, and metformin or a pharmaceutically acceptable salt thereof, in the manufacture of a medicament for preventing loss of glycaemic control in a patient with type 2 diabetes mellitus, wherein the patient has not previously received pharmaceutical treatment for the type 2 diabetes mellitus.

In another aspect, the invention relates to the use of a combination of a DPP-IV inhibitor (preferably vildagliptin or a pharmaceutically acceptable salt thereof), and metformin or a pharmaceutically acceptable salt thereof, in the manufacture of a medicament for reducing the risk of a cardiovascular event in a patient undergoing treatment for type 2 diabetes mellitus.

In another aspect, the invention relates to the use of a combination of vildagliptin or a pharmaceutically acceptable salt thereof, and metformin or a pharmaceutically acceptable salt thereof, in the manufacture of a medicament for reducing the risk of a cardiovascular event in a patient undergoing treatment for type 2 diabetes mellitus.

In another aspect, the invention relates to the use of a combination of a DPP-IV inhibitor (preferably vildagliptin or a pharmaceutically acceptable salt thereof), and metformin or a pharmaceutically acceptable salt thereof, in the manufacture of a medicament for reducing the risk of a cardiovascular event in a patient undergoing treatment for type 2 diabetes mellitus, wherein the patient has not previously received pharmaceutical treatment for the type 2 diabetes mellitus.

In another aspect, the invention relates to the use of a combination of vildagliptin or a pharmaceutically acceptable salt thereof and metformin or a pharmaceutically acceptable salt thereof, in the manufacture of a medicament for reducing the risk of a cardiovascular event in a patient undergoing treatment for type 2 diabetes mellitus, wherein the patient has not previously received pharmaceutical treatment for the type 2 diabetes mellitus.

In another aspect, the invention relates to the use of a combination of a DPP-IV inhibitor (vildagliptin or a pharmaceutically acceptable salt thereof), and metformin or a pharmaceutically acceptable salt thereof, in the manufacture of a medicament for reducing the risk of a cardiovascular event in a patient undergoing treatment for type 2 diabetes mellitus, wherein the risk is reduced relative to metformin monotherapy.

In another aspect, the invention relates to the use of a combination of a DPP-IV inhibitor (preferably vildagliptin or a pharmaceutically acceptable salt thereof), and metformin or a pharmaceutically acceptable salt thereof, in the manufacture of a medicament for reducing the risk of a cardiovascular event in a patient undergoing treatment for type 2 diabetes mellitus, wherein the risk is reduced relative to metformin monotherapy followed by subsequent co-administration of a DPP-IV inhibitor (preferably vildagliptin or a pharmaceutically acceptable salt thereof) and metformin or a pharmaceutically acceptable salt thereof.

In another aspect, the invention relates to the use of a combination of vildagliptin or a pharmaceutically acceptable salt thereof, and metformin or a pharmaceutically acceptable salt thereof, in the manufacture of a medicament for reducing the risk of a cardiovascular event in a patient undergoing treatment for type 2 diabetes mellitus, wherein the risk is reduced relative to metformin monotherapy.

In another aspect, the invention relates to the use of a combination of vildagliptin or a pharmaceutically acceptable salt thereof, and metformin or a pharmaceutically acceptable salt thereof, in the manufacture of a medicament for reducing the risk of a cardiovascular event in a patient undergoing treatment for type 2 diabetes mellitus, wherein the risk is reduced relative to metformin monotherapy followed by subsequent co-administration of a DPP-IV inhibitor (preferably vildagliptin or a pharmaceutically acceptable salt thereof) and metformin or a pharmaceutically acceptable salt thereof.

In another aspect, the invention relates to the use of a combination of a DPP-IV inhibitor (vildagliptin or a pharmaceutically acceptable salt thereof), and metformin or a pharmaceutically acceptable salt thereof, in the manufacture of a medicament for reducing the risk of a cardiovascular event in a patient undergoing treatment for type 2 diabetes mellitus, wherein the risk is reduced relative to metformin monotherapy, and wherein the patient has not previously received pharmaceutical treatment for the type 2 diabetes mellitus.

In another aspect, the invention relates to the use of a combination of a DPP-IV inhibitor (preferably vildagliptin or a pharmaceutically acceptable salt thereof), and metformin or a pharmaceutically acceptable salt thereof, in the manufacture of a medicament for reducing the risk of a cardiovascular event in a patient undergoing treatment for type 2 diabetes mellitus, wherein the risk is reduced relative to metformin monotherapy followed by subsequent co-administration of a DPP-IV inhibitor (preferably vildagliptin or a pharmaceutically acceptable salt thereof) and metformin or a pharmaceutically acceptable salt thereof, and wherein the patient has not previously received pharmaceutical treatment for the type 2 diabetes mellitus.

In another aspect, the invention relates to the use of a combination of vildagliptin or a pharmaceutically acceptable salt thereof, and metformin or a pharmaceutically acceptable salt thereof, in the manufacture of a medicament for reducing the risk of a cardiovascular event in a patient undergoing treatment for type 2 diabetes mellitus, wherein the risk is reduced relative to metformin monotherapy, and wherein the patient has not previously received pharmaceutical treatment for the type 2 diabetes mellitus.

In another aspect, the invention relates to the use of a combination of vildagliptin or a pharmaceutically acceptable salt thereof, and metformin or a pharmaceutically acceptable salt thereof, in the manufacture of a medicament for reducing the risk of a cardiovascular event in a patient undergoing treatment for type 2 diabetes mellitus, wherein the risk is reduced relative to metformin monotherapy followed by subsequent co-administration of a DPP-IV inhibitor (preferably vildagliptin or a pharmaceutically acceptable salt thereof) and metformin or a pharmaceutically acceptable salt thereof, wherein the patient has not previously received pharmaceutical treatment for the type 2 diabetes mellitus.

In another aspect, the invention relates to the use of a combination of a DPP-IV inhibitor (preferably vildagliptin or a pharmaceutically acceptable salt thereof), and metformin or a pharmaceutically acceptable salt thereof, in the manufacture of a medicament for treating type 2 diabetes mellitus without concomitant administration of insulin.

In another aspect, the invention relates to the use of a combination of vildagliptin or a pharmaceutically acceptable salt thereof, and metformin or a pharmaceutically acceptable salt thereof, in the manufacture of a medicament for treating type 2 diabetes mellitus without concomitant administration of insulin.

In another aspect, the invention relates to the use of a combination of a DPP-IV inhibitor (preferably vildagliptin or a pharmaceutically acceptable salt thereof), and metformin or a pharmaceutically acceptable salt thereof, in the manufacture of a medicament for treating type 2 diabetes mellitus without concomitant administration of insulin, wherein the patient has not previously received pharmaceutical treatment for the type 2 diabetes mellitus.

In another aspect, the invention relates to the use of a combination of vildagliptin or a pharmaceutically acceptable salt thereof, and metformin or a pharmaceutically acceptable salt thereof, in the manufacture of a medicament for treating type 2 diabetes mellitus without concomitant administration of insulin, wherein the patient has not previously received pharmaceutical treatment for the type 2 diabetes mellitus.

In one aspect, the invention relates to the use of a DPP-IV inhibitor (preferably vildagliptin or a pharmaceutically acceptable salt thereof), in the manufacture of a medicament for delaying loss of glycaemic control in a patient with type 2 diabetes mellitus, wherein the DPP-IV inhibitor (preferably vildagliptin or a pharmaceutically acceptable salt thereof) is prepared for co-administration with metformin or a pharmaceutically acceptable salt thereof.

In one aspect, the invention relates to the use of a DPP-IV inhibitor (preferably vildagliptin or a pharmaceutically acceptable salt thereof), in the manufacture of a medicament for delaying loss of glycaemic control in a patient with type 2 diabetes mellitus, wherein the patient has not previously received pharmaceutical treatment for the type 2 diabetes mellitus, and wherein the DPP-IV inhibitor (preferably vildagliptin or a pharmaceutically acceptable salt thereof) is prepared for co-administeration with metformin or a pharmaceutically acceptable salt thereof.

In one aspect, the invention relates to the use of vildagliptin or a pharmaceutically acceptable salt thereof, in the manufacture of a medicament for delaying loss of glycaemic control in a patient with type 2 diabetes mellitus, wherein the patient has not previously received pharmaceutical treatment for the type 2 diabetes mellitus, and wherein the vildagliptin or a pharmaceutically acceptable salt thereof, is prepared for co-administration with metformin or a pharmaceutically acceptable salt thereof.

In one aspect, the invention relates to the use of a DPP-IV inhibitor (preferably vildagliptin or a pharmaceutically acceptable salt thereof), in the manufacture of a medicament for delaying loss of glycaemic control in a patient with type 2 diabetes mellitus, wherein the delay is relative to metformin monotherapy, and wherein the DPP-IV inhibitor (preferably vildagliptin or a pharmaceutically acceptable salt thereof) is prepared for co-administration with metformin or a pharmaceutically acceptable salt thereof.

In one aspect, the invention relates to the use of vildagliptin or a pharmaceutically acceptable salt thereof, in the manufacture of a medicament for delaying loss of glycaemic control in a patient with type 2 diabetes mellitus, wherein the delay is relative to metformin monotherapy, and wherein the vildagliptin or a pharmaceutically acceptable salt thereof, is prepared for co-administration with metformin or a pharmaceutically acceptable salt thereof.

In one aspect, the invention relates to the use of a DPP-IV inhibitor (preferably vildagliptin or a pharmaceutically acceptable salt thereof), in the manufacture of a medicament for delaying loss of glycaemic control in a patient with type 2 diabetes mellitus, wherein the delay is relative to metformin monotherapy followed by subsequent co-administration of a DPP-IV inhibitor (preferably vildagliptin or a pharmaceutically acceptable salt thereof) and metformin or a pharmaceutically acceptable salt thereof, and wherein the DPP-IV inhibitor (preferably vildagliptin or a pharmaceutically acceptable salt thereof) is prepared for co-administration with metformin or a pharmaceutically acceptable salt thereof.

In one aspect, the invention relates to the use of vildagliptin or a pharmaceutically acceptable salt thereof, in the manufacture of a medicament for delaying loss of glycaemic control in a patient with type 2 diabetes mellitus, wherein the delay is relative to metformin monotherapy followed by subsequent co-administration of a DPP-IV inhibitor (preferably vildagliptin or a pharmaceutically acceptable salt thereof) and metformin, or a pharmaceutically acceptable salt thereof, wherein the vildagliptin or a pharmaceutically acceptable salt thereof, is prepared for co-administration with metformin or a pharmaceutically acceptable salt thereof.

In one aspect, the invention relates to the use of a DPP-IV inhibitor (preferably vildagliptin or a pharmaceutically acceptable salt thereof), in the manufacture of a medicament for delaying loss of glycaemic control in a patient with type 2 diabetes mellitus, wherein the delay is relative to metformin monotherapy, and wherein the DPP-IV inhibitor (preferably vildagliptin or a pharmaceutically acceptable salt thereof) is prepared for co-administration with metformin or a pharmaceutically acceptable salt thereof, and wherein the patient has not previously received pharmaceutical treatment for the type 2 diabetes mellitus.

In one aspect, the invention relates to the use of vildagliptin or a pharmaceutically acceptable salt thereof, in the manufacture of a medicament for delaying loss of glycaemic control in a patient with type 2 diabetes mellitus, wherein the delay is relative to metformin monotherapy, and wherein the vildagliptin or a pharmaceutically acceptable salt thereof, is prepared for co-administration with metformin or a pharmaceutically acceptable salt thereof, and wherein the patient has not previously received pharmaceutical treatment for the type 2 diabetes mellitus.

In one aspect, the invention relates to the use of a DPP-IV inhibitor (preferably vildagliptin or a pharmaceutically acceptable salt thereof), in the manufacture of a medicament for delaying loss of glycaemic control in a patient with type 2 diabetes mellitus, wherein the delay is relative to metformin monotherapy followed by subsequent co-administration of a DPP-IV inhibitor (preferably vildagliptin or a pharmaceutically acceptable salt thereof) and metformin or a pharmaceutically acceptable salt thereof, and wherein the DPP-IV inhibitor (preferably vildagliptin or a pharmaceutically acceptable salt thereof) is prepared for co-administration with metformin or a pharmaceutically acceptable salt thereof, wherein the patient has not previously received pharmaceutical treatment for the type 2 diabetes mellitus.

In one aspect, the invention relates to the use of vildagliptin or a pharmaceutically acceptable salt thereof, in the manufacture of a medicament for delaying loss of glycaemic control in a patient with type 2 diabetes mellitus, wherein the delay is relative to metformin monotherapy followed by subsequent co-administration of a DPP-IV inhibitor (preferably vildagliptin or a pharmaceutically acceptable salt thereof) and metformin or a pharmaceutically acceptable salt thereof, and wherein the vildagliptin or a pharmaceutically acceptable salt thereof, is prepared for co-administration with metformin or a pharmaceutically acceptable salt thereof, wherein the patient has not previously received pharmaceutical treatment for the type 2 diabetes mellitus.

In another aspect, the invention relates to the use of a DPP-IV inhibitor (preferably vildagliptin or a pharmaceutically acceptable salt thereof), in the manufacture of a medicament for improving glycaemic control in a patient with type 2 diabetes mellitus, wherein the DPP-IV inhibitor (preferably vildagliptin or a pharmaceutically acceptable salt thereof) is prepared for co-administration with metformin or a pharmaceutically acceptable salt thereof.

In another aspect, the invention relates to the use of a DPP-IV inhibitor (preferably vildagliptin or a pharmaceutically acceptable salt thereof), in the manufacture of a medicament for improving glycaemic control in a patient with type 2 diabetes mellitus, wherein the improvement in glycaemic control is relative to metformin monotherapy, and wherein the DPP-IV inhibitor (preferably vildagliptin or a pharmaceutically acceptable salt thereof) is prepared for co-administration with metformin or a pharmaceutically acceptable salt thereof, or a pharmaceutically acceptable salt thereof.

In another aspect, the invention relates to the use of vildagliptin or a pharmaceutically acceptable salt thereof, in the manufacture of a medicament for improving glycaemic control in a patient with type 2 diabetes mellitus, wherein the improvement in glycaemic control is relative to metformin monotherapy, and wherein the vildagliptin or a pharmaceutically acceptable salt thereof, is prepared for co-administration with metformin or a pharmaceutically acceptable salt thereof.

In another aspect, the invention relates to the use of a DPP-IV inhibitor (preferably vildagliptin or a pharmaceutically acceptable salt thereof), in the manufacture of a medicament for improving glycaemic control in a patient with type 2 diabetes mellitus, wherein the improvement in glycaemic control is relative to metformin monotherapy followed by subsequent co-administration of a DPP-IV inhibitor (preferably vildagliptin or a pharmaceutically acceptable salt thereof) and metformin or a pharmaceutically acceptable salt thereof, and wherein the DPP-IV inhibitor (preferably vildagliptin or a pharmaceutically acceptable salt thereof) is prepared for co-administration with metformin or a pharmaceutically acceptable salt thereof.

In another aspect, the invention relates to the use of vildagliptin or a pharmaceutically acceptable salt thereof, in the manufacture of a medicament for improving glycaemic control in a patient with type 2 diabetes mellitus, wherein the improvement in glycaemic control is relative to metformin monotherapy followed by subsequent co-administration of a DPP-IV inhibitor (preferably vildagliptin or a pharmaceutically acceptable salt thereof) and metformin or a pharmaceutically acceptable salt thereof, and wherein the DPP-IV inhibitor (preferably vildagliptin or a pharmaceutically acceptable salt thereof) is prepared for co-administration with metformin or a pharmaceutically acceptable salt thereof.

In another aspect, the invention relates to the use of a DPP-IV inhibitor (preferably vildagliptin or a pharmaceutically acceptable salt thereof), in the manufacture of a medicament for improving glycaemic control in a patient with type 2 diabetes mellitus, wherein the improvement in glycaemic control is relative to metformin monotherapy, and wherein the DPP-IV inhibitor (preferably vildagliptin or a pharmaceutically acceptable salt thereof) is prepared for co-administration with metformin or a pharmaceutically acceptable salt thereof, and wherein the patient has not previously received pharmaceutical treatment for the type 2 diabetes mellitus.

In another aspect, the invention relates to the use of vildagliptin or a pharmaceutically acceptable salt thereof, in the manufacture of a medicament for improving glycaemic control in a patient with type 2 diabetes mellitus, wherein the improvement in glycaemic control is relative to metformin monotherapy, and wherein the vildagliptin or a pharmaceutically acceptable salt thereof is prepared for co-administration with metformin or a pharmaceutically acceptable salt thereof, and wherein the patient has not previously received pharmaceutical treatment for the type 2 diabetes mellitus.

In another aspect, the invention relates to the use of a DPP-IV inhibitor (preferably vildagliptin or a pharmaceutically acceptable salt thereof), in the manufacture of a medicament for improving glycaemic control in a patient with type 2 diabetes mellitus, wherein the improvement in glycaemic control is relative to metformin monotherapy followed by subsequent co-administration of a DPP-IV inhibitor (preferably vildagliptin or a pharmaceutically acceptable salt thereof) and metformin or a pharmaceutically acceptable salt thereof, and wherein the DPP-IV inhibitor (preferably vildagliptin or a pharmaceutically acceptable salt thereof) is prepared for co-administration with metformin or a pharmaceutically acceptable salt thereof, and wherein the patient has not previously received pharmaceutical treatment for the type 2 diabetes mellitus.

In another aspect, the invention relates to the use of vildagliptin or a pharmaceutically acceptable salt thereof, in the manufacture of a medicament for improving glycaemic control in a patient with type 2 diabetes mellitus, wherein the improvement in glycaemic control is relative to metformin monotherapy followed by subsequent co-administration of a DPP-IV inhibitor (preferably vildagliptin or a pharmaceutically acceptable salt thereof) and metformin or a pharmaceutically acceptable salt thereof, and wherein the vildagliptin or a pharmaceutically acceptable salt thereof is prepared for co-administration with metformin or a pharmaceutically acceptable salt thereof, and wherein the patient has not previously received pharmaceutical treatment for the type 2 diabetes mellitus.

In another aspect, the invention relates to the use of a DPP-IV inhibitor (preferably vildagliptin or a pharmaceutically acceptable salt thereof), in the manufacture of a medicament for improving glycaemic control in a patient with type 2 diabetes mellitus, wherein the patient has not previously received pharmaceutical treatment for the type 2 diabetes mellitus, and wherein the DPP-IV inhibitor (preferably vildagliptin or a pharmaceutically acceptable salt thereof) is prepared for co-administration with metformin or a pharmaceutically acceptable salt thereof.

In another aspect, the invention relates to the use of vildagliptin or a pharmaceutically acceptable salt thereof in the manufacture of a medicament for improving glycaemic control in a patient with type 2 diabetes mellitus, wherein the patient has not previously received pharmaceutical treatment for the type 2 diabetes mellitus, and wherein the vildagliptin or a pharmaceutically acceptable salt thereof is prepared for co-administration with metformin or a pharmaceutically acceptable salt thereof.

In another aspect, the invention relates to the use of a DPP-IV inhibitor (preferably vildagliptin or a pharmaceutically acceptable salt thereof), in the manufacture of a medicament for delaying the increase of $HbA_{1c}$ to greater than or equal to 53 mmol/mol (7.0%) in a patient with type 2 diabetes mellitus, and wherein the DPP-IV inhibitor (preferably vildagliptin or a pharmaceutically acceptable salt thereof) is prepared for co-administration with metformin or a pharmaceutically acceptable salt thereof.

In another aspect, the invention relates to the use of a DPP-IV inhibitor (preferably vildagliptin or a pharmaceutically acceptable salt thereof), in the manufacture of a medicament for delaying the increase of $HbA_{1c}$ to greater than or equal to 53 mmol/mol (7.0%) in a patient with type 2 diabetes mellitus, wherein the delay in the increase of $HbA_{1c}$ is relative to metformin monotherapy, and wherein the DPP-IV inhibitor (preferably vildagliptin or a pharmaceutically acceptable salt thereof), is prepared for co-administration with metformin or a pharmaceutically acceptable salt thereof.

In another aspect, the invention relates to the use of vildagliptin or a pharmaceutically acceptable salt thereof, in the manufacture of a medicament for delaying the increase of $HbA_{1c}$ to greater than or equal to 53 mmol/mol (7.0%) in a patient with type 2 diabetes mellitus, wherein the delay in the increase of $HbA_{1c}$ is relative to metformin monotherapy, and wherein the vildagliptin or a pharmaceutically acceptable salt thereof, is prepared for co-administration with metformin or a pharmaceutically acceptable salt thereof.

In another aspect, the invention relates to the use of a DPP-IV inhibitor (preferably vildagliptin or a pharmaceutically acceptable salt thereof) in the manufacture of a medicament for delaying the increase of $HbA_{1c}$ to greater than or equal to 53 mmol/mol (7.0%) in a patient with type 2 diabetes mellitus, wherein the delay in the increase of $HbA_{1c}$ is relative to metformin monotherapy followed by subsequent co-administration of a DPP-IV inhibitor (preferably vildagliptin or a pharmaceutically acceptable salt thereof) and metformin or a pharmaceutically acceptable salt thereof, and wherein the vildagliptin or a pharmaceutically acceptable salt thereof, is prepared for co-administration with metformin or a pharmaceutically acceptable salt thereof.

In another aspect, the invention relates to the use of vildagliptin or a pharmaceutically acceptable salt thereof, in the manufacture of a medicament for delaying the increase of $HbA_{1c}$ to greater than or equal to 53 mmol/mol (7.0%) in a patient with type 2 diabetes mellitus, wherein the delay in the increase of $HbA_{1c}$ is relative to metformin monotherapy followed by subsequent co-administration of a DPP-IV inhibitor (preferably vildagliptin or a pharmaceutically acceptable salt thereof) and metformin or a pharmaceutically acceptable salt thereof, and wherein the vildagliptin or a pharmaceutically acceptable salt thereof, is prepared for co-administration with metformin or a pharmaceutically acceptable salt thereof.

In another aspect, the invention relates to the use of a DPP-IV inhibitor (preferably vildagliptin or a pharmaceutically acceptable salt thereof), in the manufacture of a medicament for delaying the increase of $HbA_{1c}$ to greater than or equal to 53 mmol/mol (7.0%) in a patient with type 2 diabetes mellitus, wherein the delay in the increase of $HbA_{1c}$ is relative to metformin monotherapy, and wherein the vildagliptin or a pharmaceutically acceptable salt thereof, is prepared for co-administration with metformin or a pharmaceutically acceptable salt thereof, and wherein the patient has not previously received pharmaceutical treatment for the type 2 diabetes mellitus.

In another aspect, the invention relates to the use of vildagliptin or a pharmaceutically acceptable salt thereof, in the manufacture of a medicament for delaying the increase of $HbA_{1c}$ to greater than or equal to 53 mmol/mol (7.0%) in a patient with type 2 diabetes mellitus, wherein the delay in the increase of $HbA_{1c}$ is relative to metformin monotherapy, and wherein the vildagliptin or a pharmaceutically acceptable salt thereof, is prepared for co-administration with metformin or a pharmaceutically acceptable salt thereof, and wherein the patient has not previously received pharmaceutical treatment for the type 2 diabetes mellitus.

In another aspect, the invention relates to the use of a DPP-IV inhibitor (preferably vildagliptin or a pharmaceutically acceptable salt thereof), in the manufacture of a medicament for delaying the increase of $HbA_{1c}$ to greater than or equal to 53 mmol/mol (7.0%) in a patient with type 2 diabetes mellitus, wherein the delay in the increase of $HbA_{1c}$ is relative to metformin monotherapy followed by subsequent co-administration of a DPP-IV inhibitor (preferably vildagliptin or a pharmaceutically acceptable salt thereof) and metformin or a pharmaceutically acceptable salt thereof, and wherein the vildagliptin or a pharmaceutically acceptable salt thereof, is prepared for co-administration with metformin or a pharmaceutically acceptable salt thereof, and wherein the patient has not previously received pharmaceutical treatment for the type 2 diabetes mellitus.

In another aspect, the invention relates to the use of vildagliptin or a pharmaceutically acceptable salt thereof, in the manufacture of a medicament for delaying the increase of $HbA_{1c}$ to greater than or equal to 53 mmol/mol (7.0%) in a patient with type 2 diabetes mellitus, wherein the delay in the increase of $HbA_{1c}$ is relative to metformin monotherapy followed by subsequent co-administration of a DPP-IV inhibitor (preferably vildagliptin or a pharmaceutically acceptable salt thereof) and metformin or a pharmaceutically acceptable salt thereof, and wherein the vildagliptin or a pharmaceutically acceptable salt thereof, is prepared for co-administration with metformin or a pharmaceutically acceptable salt thereof, and wherein the patient has not previously received pharmaceutical treatment for the type 2 diabetes mellitus.

In another aspect, the invention relates to the use of a DPP-IV inhibitor (preferably vildagliptin or a pharmaceutically acceptable salt thereof), in the manufacture of a medicament for delaying the increase of $HbA_{1c}$ to greater than or equal to 53 mmol/mol (7.0%) in a patient with type 2 diabetes mellitus, wherein the patient has not previously received pharmaceutical treatment for the type 2 diabetes mellitus, and wherein DPP-IV inhibitor (preferably vildagliptin or a pharmaceutically acceptable salt thereof), is prepared for co-administration with metformin or a pharmaceutically acceptable salt thereof.

In another aspect, the invention relates to the use of vildagliptin or a pharmaceutically acceptable salt thereof, in the manufacture of a medicament for delaying the increase of $HbA_{1c}$ to greater than or equal to 53 mmol/mol (7.0%) in a patient with type 2 diabetes mellitus, wherein the patient has not previously received pharmaceutical treatment for the type 2 diabetes mellitus, and wherein the vildagliptin or a pharmaceutically acceptable salt thereof, is prepared for co-administration with metformin or a pharmaceutically acceptable salt thereof.

In another aspect, the invention relates to the use of a DPP-IV inhibitor (preferably vildagliptin or a pharmaceutically acceptable salt thereof), in the manufacture of a medicament for increasing the time taken to reach an $HbA_{1c}$ measurement of greater than or equal to 53 mmol/mol (7.0%) in a patient with type 2 diabetes mellitus, and wherein the DPP-IV inhibitor (preferably vildagliptin or a pharmaceutically acceptable salt thereof) is prepared for co-administration with metformin or a pharmaceutically acceptable salt thereof.

In another aspect, the invention relates to the use of a DPP-IV inhibitor (preferably vildagliptin or a pharmaceutically acceptable salt thereof), in the manufacture of a medicament for increasing the time taken to reach an $HbA_{1c}$ measurement of greater than or equal to 53 mmol/mol (7.0%) in a patient with type 2 diabetes mellitus, wherein the increase is relative to metformin monotherapy, and wherein the DPP-IV inhibitor (preferably vildagliptin or a pharmaceutically acceptable salt thereof) is prepared for co-administration with metformin or a pharmaceutically acceptable salt thereof.

In another aspect, the invention relates to the use of vildagliptin or a pharmaceutically acceptable salt thereof, in the manufacture of a medicament for increasing the time taken to reach an $HbA_{1c}$ measurement of greater than or equal to 53 mmol/mol (7.0%) in a patient with type 2 diabetes mellitus, wherein the increase is relative to metformin monotherapy, and wherein the vildagliptin or a pharmaceutically acceptable salt thereof, is prepared for co-administration with metformin or a pharmaceutically acceptable salt thereof.

In another aspect, the invention relates to the use of a DPP-IV inhibitor (preferably vildagliptin or a pharmaceutically acceptable salt thereof), in the manufacture of a medicament for increasing the time taken to reach an $HbA_{1c}$ measurement of greater than or equal to 53 mmol/mol (7.0%) in a patient with type 2 diabetes mellitus, wherein the increase is relative to metformin monotherapy followed by subsequent co-administration of a DPP-IV inhibitor (preferably vildagliptin or a pharmaceutically acceptable salt thereof) and metformin or a pharmaceutically acceptable salt thereof, and wherein the DPP-IV inhibitor (preferably vildagliptin or a pharmaceutically acceptable salt thereof) is prepared for co-administration with metformin or a pharmaceutically acceptable salt thereof.

In another aspect, the invention relates to the use of vildagliptin or a pharmaceutically acceptable salt thereof, in the manufacture of a medicament for increasing the time taken to reach an $HbA_{1c}$ measurement of greater than or equal to 53 mmol/mol (7.0%) in a patient with type 2 diabetes mellitus, wherein the increase is relative to metformin monotherapy followed by subsequent co-administration of a DPP-IV inhibitor (preferably vildagliptin or a pharmaceutically acceptable salt thereof) and metformin or a pharmaceutically acceptable salt thereof, and wherein the vildagliptin or a pharmaceutically acceptable salt thereof, is prepared for co-administration with metformin or a pharmaceutically acceptable salt thereof.

In another aspect, the invention relates to the use of a DPP-IV inhibitor (preferably vildagliptin or a pharmaceutically acceptable salt thereof), in the manufacture of a medicament for increasing the time taken to reach an $HbA_{1c}$ measurement of greater than or equal to 53 mmol/mol (7.0%) in a patient with type 2 diabetes mellitus, wherein the increase is relative to metformin monotherapy, and wherein the DPP-IV inhibitor (preferably vildagliptin or a pharmaceutically acceptable salt thereof) is prepared for co-administration with metformin or a pharmaceutically acceptable salt thereof, and wherein the patient has not previously received pharmaceutical treatment for the type 2 diabetes mellitus.

In another aspect, the invention relates to the use of vildagliptin or a pharmaceutically acceptable salt thereof, in the manufacture of a medicament for increasing the time taken to reach an $HbA_{1c}$ measurement of greater than or equal to 53 mmol/mol (7.0%) in a patient with type 2 diabetes mellitus, wherein the increase is relative to metformin monotherapy, and wherein the vildagliptin or a pharmaceutically acceptable salt thereof, is prepared for co-administration with metformin or a pharmaceutically acceptable salt thereof, and wherein the patient has not previously received pharmaceutical treatment for the type 2 diabetes mellitus.

In another aspect, the invention relates to the use of a DPP-IV inhibitor (preferably vildagliptin or a pharmaceutically acceptable salt thereof), in the manufacture of a medicament for increasing the time taken to reach an $HbA_{1c}$ measurement of greater than or equal to 53 mmol/mol (7.0%) in a patient with type 2 diabetes mellitus, wherein the increase is relative to metformin monotherapy followed by subsequent co-administration of a DPP-IV inhibitor (preferably vildagliptin or a pharmaceutically acceptable salt thereof) and metformin or a pharmaceutically acceptable salt thereof, and wherein the DPP-IV inhibitor (preferably vildagliptin or a pharmaceutically acceptable salt thereof) is prepared for co-administration with metformin or a pharmaceutically acceptable salt thereof, and wherein the patient has not previously received pharmaceutical treatment for the type 2 diabetes mellitus.

In another aspect, the invention relates to the use of vildagliptin or a pharmaceutically acceptable salt thereof, in the manufacture of a medicament for increasing the time taken to reach an $HbA_{1c}$ measurement of greater than or equal to 53 mmol/mol (7.0%) in a patient with type 2 diabetes mellitus, wherein the increase is relative to metformin monotherapy followed by subsequent co-administration of a DPP-IV inhibitor (preferably vildagliptin or a pharmaceutically acceptable salt thereof) and metformin or a pharmaceutically acceptable salt thereof, and wherein the vildagliptin or a pharmaceutically acceptable salt thereof, is prepared for co-administration with metformin or a pharmaceutically acceptable salt thereof, and wherein the patient has not previously received pharmaceutical treatment for the type 2 diabetes mellitus.

In another aspect, the invention relates to the use of a DPP-IV inhibitor (preferably vildagliptin or a pharmaceutically acceptable salt thereof), in the manufacture of a medicament for increasing the time taken to reach an $HbA_{1c}$ measurement of greater than or equal to 53 mmol/mol (7.0%) in a patient with type 2 diabetes mellitus, wherein the patient has not previously received pharmaceutical treatment for the type 2 diabetes mellitus, and wherein the DPP-IV inhibitor (preferably vildagliptin or a pharmaceutically acceptable salt thereof) is prepared for co-administration with metformin or a pharmaceutically acceptable salt thereof.

In another aspect, the invention relates to the use of vildagliptin or a pharmaceutically acceptable salt thereof, in the manufacture of a medicament for increasing the time taken to reach an $HbA_{1c}$ measurement of greater than or equal to 53 mmol/mol (7.0%) in a patient with type 2 diabetes mellitus, wherein the patient has not previously received pharmaceutical treatment for the type 2 diabetes mellitus, and wherein the vildagliptin or a pharmaceutically acceptable salt thereof, is prepared for co-administration with metformin or a pharmaceutically acceptable salt thereof.

In another aspect, the invention relates to the use of a DPP-IV inhibitor (preferably vildagliptin or a pharmaceutically acceptable salt thereof) in the manufacture of a medicament for preventing loss of glycaemic control in a patient with type 2 diabetes mellitus, wherein the DPP-IV inhibitor (preferably vildagliptin or a pharmaceutically acceptable salt thereof) is prepared for co-administration with metformin or a pharmaceutically acceptable salt thereof.

In another aspect, the invention relates to the use of vildagliptin or a pharmaceutically acceptable salt thereof, in the manufacture of a medicament for preventing loss of glycaemic control in a patient with type 2 diabetes mellitus, wherein the vildagliptin or a pharmaceutically acceptable salt thereof, is prepared for co-administration with metformin or a pharmaceutically acceptable salt thereof.

In another aspect, the invention relates to the use of a DPP-IV inhibitor (preferably vildagliptin or a pharmaceutically acceptable salt thereof) in the manufacture of a medicament for preventing loss of glycaemic control in a patient with type 2 diabetes mellitus, wherein the DPP-IV inhibitor (preferably vildagliptin or a pharmaceutically acceptable salt thereof) is prepared for co-administration with metformin or a pharmaceutically acceptable salt thereof, and wherein the patient has not previously received pharmaceutical treatment for the type 2 diabetes mellitus.

In another aspect, the invention relates to the use of vildagliptin or a pharmaceutically acceptable salt thereof, in the manufacture of a medicament for preventing loss of glycaemic control in a patient with type 2 diabetes mellitus, wherein the vildagliptin or a pharmaceutically acceptable salt thereof, is prepared for co-administered with metformin or a pharmaceutically acceptable salt thereof, and wherein the patient has not previously received pharmaceutical treatment for the type 2 diabetes mellitus.

In another aspect, the invention relates to the use of a DPP-IV inhibitor (preferably vildagliptin or a pharmaceutically acceptable salt thereof), in the manufacture of a medicament for reducing the risk of a cardiovascular event in a patient undergoing treatment for type 2 diabetes mellitus, wherein the DPP-IV inhibitor (preferably vildagliptin or a pharmaceutically acceptable salt thereof) is prepared for co-administration with metformin or a pharmaceutically acceptable salt thereof.

In another aspect, the invention relates to the use of vildagliptin or a pharmaceutically acceptable salt thereof, in the manufacture of a medicament for reducing the risk of a cardiovascular event in a patient undergoing treatment for type 2 diabetes mellitus, wherein the vildagliptin or a pharmaceutically acceptable salt thereof, is prepared for co-administration with metformin or a pharmaceutically acceptable salt thereof.

In another aspect, the invention relates to the use of a DPP-IV inhibitor (preferably vildagliptin or a pharmaceutically acceptable salt thereof), in the manufacture of a medicament for reducing the risk of a cardiovascular event in a patient undergoing treatment for type 2 diabetes mellitus, wherein the DPP-IV inhibitor (preferably vildagliptin or a pharmaceutically acceptable salt thereof) is prepared for co-administration with metformin or a pharmaceutically acceptable salt thereof, and wherein the risk is reduced relative to metformin monotherapy.

In another aspect, the invention relates to the use of a DPP-IV inhibitor (preferably vildagliptin or a pharmaceutically acceptable salt thereof), in the manufacture of a medicament for reducing the risk of a cardiovascular event in a patient undergoing treatment for type 2 diabetes mellitus, wherein the DPP-IV inhibitor (preferably vildagliptin or a pharmaceutically acceptable salt thereof) is prepared for co-administration with metformin or a pharmaceutically acceptable salt thereof, and wherein the risk is reduced relative to metformin monotherapy followed by subsequent co-administration of a DPP-IV inhibitor (preferably vildagliptin or a pharmaceutically acceptable salt thereof) and metformin or a pharmaceutically acceptable salt thereof.

In another aspect, the invention relates to the use of vildagliptin or a pharmaceutically acceptable salt thereof, in the manufacture of a medicament for reducing the risk of a cardiovascular event in a patient undergoing treatment for type 2 diabetes mellitus, wherein the vildagliptin or a pharmaceutically acceptable salt thereof, is prepared for co-administration with metformin or a pharmaceutically acceptable salt thereof, and wherein the risk is reduced relative to metformin monotherapy.

In another aspect, the invention relates to the use of vildagliptin or a pharmaceutically acceptable salt thereof, in the manufacture of a medicament for reducing the risk of a cardiovascular event in a patient undergoing treatment for type 2 diabetes mellitus, wherein the vildagliptin or a pharmaceutically acceptable salt thereof, is prepared for co-administration with metformin or a pharmaceutically acceptable salt thereof, and wherein the risk is reduced relative to metformin monotherapy followed by subsequent co-administration of a DPP-IV inhibitor (preferably vildagliptin or a pharmaceutically acceptable salt thereof) and metformin or a pharmaceutically acceptable salt thereof.

In another aspect, the invention relates to the use of a DPP-IV inhibitor (preferably vildagliptin or a pharmaceutically acceptable salt thereof), in the manufacture of a medicament for reducing the risk of a cardiovascular event in a patient undergoing treatment for type 2 diabetes mellitus, wherein the DPP-IV inhibitor (preferably vildagliptin or a pharmaceutically acceptable salt thereof) is prepared for co-administration with metformin or a pharmaceutically acceptable salt thereof, and wherein the risk is reduced relative to metformin monotherapy, and wherein the patient has not previously received pharmaceutical treatment for the type 2 diabetes mellitus.

In another aspect, the invention relates to the use of a DPP-IV inhibitor (preferably vildagliptin or a pharmaceutically acceptable salt thereof), in the manufacture of a medicament for reducing the risk of a cardiovascular event in a patient undergoing treatment for type 2 diabetes mellitus, wherein the DPP-IV inhibitor (preferably vildagliptin or a pharmaceutically acceptable salt thereof) is prepared for co-administration with metformin or a pharmaceutically acceptable salt thereof, and wherein the risk is reduced relative to metformin monotherapy followed by subsequent co-administration of a DPP-IV inhibitor (preferably vildagliptin or a pharmaceutically acceptable salt thereof) and metformin or a pharmaceutically acceptable salt thereof, and wherein the patient has not previously received pharmaceutical treatment for the type 2 diabetes mellitus.

In another aspect, the invention relates to the use of vildagliptin or a pharmaceutically acceptable salt thereof in the manufacture of a medicament for reducing the risk of a cardiovascular event in a patient undergoing treatment for type 2 diabetes mellitus, wherein the vildagliptin or a pharmaceutically acceptable salt thereof, is prepared for co-administration with metformin or a pharmaceutically acceptable salt thereof, and wherein the risk is reduced relative to metformin monotherapy, and wherein the patient has not previously received pharmaceutical treatment for the type 2 diabetes mellitus.

In another aspect, the invention relates to the use of vildagliptin or a pharmaceutically acceptable salt thereof, in the manufacture of a medicament for reducing the risk of a cardiovascular event in a patient undergoing treatment for type 2 diabetes mellitus, wherein the vildagliptin or a pharmaceutically acceptable salt thereof, is prepared for co-administered with metformin or a pharmaceutically acceptable salt thereof, and wherein the risk is reduced relative to metformin monotherapy followed by subsequent co-administration of a DPP-IV inhibitor (preferably vildagliptin or a pharmaceutically acceptable salt thereof) and metformin or a pharmaceutically acceptable salt thereof, and wherein the patient has not previously received pharmaceutical treatment for the type 2 diabetes mellitus.

In another aspect, the invention relates to the use of a DPP-IV inhibitor (preferably vildagliptin or a pharmaceutically acceptable salt thereof), in the manufacture of a medicament for reducing the risk of a cardiovascular event in a patient undergoing treatment for type 2 diabetes mellitus, wherein the DPP-IV inhibitor (preferably vildagliptin or a pharmaceutically acceptable salt thereof) is prepared for co-administration with metformin or a pharmaceutically acceptable salt thereof, and wherein the patient has not previously received pharmaceutical treatment for the type 2 diabetes mellitus.

In another aspect, the invention relates to the use of vildagliptin or a pharmaceutically acceptable salt thereof, in the manufacture of a medicament for reducing the risk of a cardiovascular event in a patient undergoing treatment for type 2 diabetes mellitus, wherein the vildagliptin or a pharmaceutically acceptable salt thereof, is prepared for co-administration with metformin or a pharmaceutically acceptable salt thereof, and wherein the patient has not previously received pharmaceutical treatment for the type 2 diabetes mellitus.

In another aspect, the invention relates to the use of a DPP-IV inhibitor (preferably vildagliptin or a pharmaceutically acceptable salt thereof), in the manufacture of a medicament for treating type 2 diabetes mellitus without concomitant administration of insulin, and wherein the DPP-IV inhibitor (preferably vildagliptin or a pharmaceutically acceptable salt thereof) is prepared for co-administered with metformin or a pharmaceutically acceptable salt thereof.

In another aspect, the invention relates to the use of vildagliptin or a pharmaceutically acceptable salt thereof, in the manufacture of a medicament for treating type 2 diabetes mellitus without concomitant administration of insulin, and wherein the vildagliptin or a pharmaceutically acceptable salt thereof is prepared for co-administration with metformin or a pharmaceutically acceptable salt thereof.

In another aspect, the invention relates to the use of a DPP-IV inhibitor (preferably vildagliptin or a pharmaceutically acceptable salt thereof), in the manufacture of a medicament for treating type 2 diabetes mellitus without concomitant administration of insulin, and wherein the DPP-IV inhibitor (preferably vildagliptin or a pharmaceutically acceptable salt thereof) is prepared for co-administration with metformin or a pharmaceutically acceptable salt thereof, and wherein the patient has not previously received pharmaceutical treatment for the type 2 diabetes mellitus.

In another aspect, the invention relates to the use of vildagliptin or a pharmaceutically acceptable salt thereof, in the manufacture of a medicament for treating type 2 diabetes mellitus without concomitant administration of insulin, and wherein the vildagliptin or a pharmaceutically acceptable salt thereof is prepared for co-administration with metformin or a pharmaceutically acceptable salt thereof, and wherein the patient has not previously received pharmaceutical treatment for the type 2 diabetes mellitus.

In another aspect, the invention relates to the use of metformin or a pharmaceutically acceptable salt thereof, in the manufacture of a medicament for delaying loss of glycaemic control in a patient with type 2 diabetes mellitus, wherein the metformin or a pharmaceutically acceptable salt thereof, is prepared for co-administration with a DPP-IV inhibitor (preferably vildagliptin or a pharmaceutically acceptable salt thereof).

In another aspect, the invention relates to the use of metformin or a pharmaceutically acceptable salt thereof, in the manufacture of a medicament for delaying loss of glycaemic control in a patient with type 2 diabetes mellitus, wherein the metformin or a pharmaceutically acceptable salt thereof, is prepared for co-administration with a DPP-IV inhibitor (preferably vildagliptin or a pharmaceutically acceptable salt thereof), and wherein the loss of glycaemic control is delayed relative to metformin monotherapy.

In another aspect, the invention relates to the use of metformin or a pharmaceutically acceptable salt thereof, in the manufacture of a medicament for delaying loss of glycaemic control in a patient with type 2 diabetes mellitus, wherein the metformin or a pharmaceutically acceptable salt thereof, is prepared for co-administration with vildagliptin or a pharmaceutically acceptable salt thereof, and wherein the loss of glycaemic control is delayed relative to metformin monotherapy.

In another aspect, the invention relates to the use of metformin or a pharmaceutically acceptable salt thereof, in the manufacture of a medicament for delaying loss of glycaemic control in a patient with type 2 diabetes mellitus, wherein the metformin or a pharmaceutically acceptable salt thereof, is prepared for co-administration with a DPP-IV inhibitor (preferably vildagliptin or a pharmaceutically acceptable salt thereof), and wherein the loss of glycaemic control is delayed relative to metformin monotherapy followed by subsequent co-administration of a DPP-IV inhibitor (preferably vildagliptin or a pharmaceutically acceptable salt thereof) and metformin or a pharmaceutically acceptable salt thereof.

In another aspect, the invention relates to the use of metformin or a pharmaceutically acceptable salt thereof, in the manufacture of a medicament for delaying loss of glycaemic control in a patient with type 2 diabetes mellitus, wherein the metformin or a pharmaceutically acceptable salt thereof, is prepared for co-administration with vildagliptin or a pharmaceutically acceptable salt thereof, and wherein the loss of glycaemic control is delayed relative to metformin monotherapy followed by subsequent co-administration of a DPP-IV inhibitor (preferably vildagliptin or a pharmaceutically acceptable salt thereof) and metformin or a pharmaceutically acceptable salt thereof.

In another aspect, the invention relates to the use of metformin or a pharmaceutically acceptable salt thereof, in the manufacture of a medicament for delaying loss of glycaemic control in a patient with type 2 diabetes mellitus, wherein the metformin or a pharmaceutically acceptable salt thereof, is prepared for co-administration with a DPP-IV inhibitor (preferably vildagliptin or a pharmaceutically acceptable salt thereof), and wherein the loss of glycaemic control is delayed relative to metformin monotherapy, and wherein the patient has not previously received pharmaceutical treatment for the type 2 diabetes mellitus.

In another aspect, the invention relates to the use of metformin or a pharmaceutically acceptable salt thereof, in the manufacture of a medicament for delaying loss of glycaemic control in a patient with type 2 diabetes mellitus, wherein the metformin or a pharmaceutically acceptable salt thereof, is prepared for co-administration with vildagliptin or a pharmaceutically acceptable salt thereof, and wherein the loss of glycaemic control is delayed relative to metformin monotherapy, and wherein the patient has not previously received pharmaceutical treatment for the type 2 diabetes mellitus.

In another aspect, the invention relates to the use of metformin or a pharmaceutically acceptable salt thereof, in the manufacture of a medicament for delaying loss of glycaemic control in a patient with type 2 diabetes mellitus, wherein the metformin or a pharmaceutically acceptable salt thereof, is prepared for co-administration with a DPP-IV inhibitor (preferably vildagliptin or a pharmaceutically acceptable salt thereof), and wherein the loss of glycaemic control is delayed relative to metformin monotherapy followed by subsequent co-administration of a DPP-IV inhibitor (preferably vildagliptin or a pharmaceutically acceptable salt thereof) and metformin or a pharmaceutically acceptable salt thereof, and wherein the patient has not previously received pharmaceutical treatment for the type 2 diabetes mellitus.

In another aspect, the invention relates to the use of metformin or a pharmaceutically acceptable salt thereof, in the manufacture of a medicament for delaying loss of glycaemic control in a patient with type 2 diabetes mellitus, wherein the metformin or a pharmaceutically acceptable salt thereof, is prepared for co-administration with vildagliptin or a pharmaceutically acceptable salt thereof, and wherein the loss of glycaemic control is delayed relative to metformin monotherapy followed by subsequent co-administration of a DPP-IV inhibitor (preferably vildagliptin or a pharmaceutically acceptable salt thereof) and metformin or a pharmaceutically acceptable salt thereof, and wherein the patient has not previously received pharmaceutical treatment for the type 2 diabetes mellitus.

In another aspect, the invention relates to the use of metformin or a pharmaceutically acceptable salt thereof, in the manufacture of a medicament for delaying loss of glycaemic control in a patient with type 2 diabetes mellitus, wherein the metformin or a pharmaceutically acceptable salt thereof, is prepared for co-administration with a DPP-IV inhibitor (preferably vildagliptin or a pharmaceutically acceptable salt thereof), and wherein the patient has not previously received pharmaceutical treatment for the type 2 diabetes mellitus.

In another aspect, the invention relates to the use of metformin or a pharmaceutically acceptable salt thereof, in the manufacture of a medicament for delaying loss of glycaemic control in a patient with type 2 diabetes mellitus, wherein the metformin or a pharmaceutically acceptable salt thereof, is prepared for co-administration with vildagliptin or a pharmaceutically acceptable salt thereof, and wherein the patient has not previously received pharmaceutical treatment for the type 2 diabetes mellitus.

In another aspect, the invention relates to the use of metformin or a pharmaceutically acceptable salt thereof, in the manufacture of a medicament for improving glycaemic control in a patient with type 2 diabetes mellitus, wherein the metformin or a pharmaceutically acceptable salt thereof, is prepared for co-administration with a DPP-IV inhibitor (preferably vildagliptin or a pharmaceutically acceptable salt thereof).

In another aspect, the invention relates to the use of metformin or a pharmaceutically acceptable salt thereof, in the manufacture of a medicament for improving glycaemic control in a patient with type 2 diabetes mellitus, wherein the metformin or a pharmaceutically acceptable salt thereof, is prepared for co-administration with a DPP-IV inhibitor (preferably vildagliptin or a pharmaceutically acceptable salt thereof), and wherein the improvement in glycaemic control is relative to metformin monotherapy.

In another aspect, the invention relates to the use of metformin or a pharmaceutically acceptable salt thereof, in the manufacture of a medicament for improving glycaemic control in a patient with type 2 diabetes mellitus, wherein the metformin or a pharmaceutically acceptable salt thereof, is prepared for co-administration with vildagliptin or a pharmaceutically acceptable salt thereof, and wherein the improvement in glycaemic control is relative to metformin monotherapy.

In another aspect, the invention relates to the use of metformin or a pharmaceutically acceptable salt thereof, in the manufacture of a medicament for improving glycaemic control in a patient with type 2 diabetes mellitus, wherein the metformin or a pharmaceutically acceptable salt thereof, is prepared for co-administration with a DPP-IV inhibitor (preferably vildagliptin or a pharmaceutically acceptable salt thereof), and wherein the improvement in glycaemic control is relative to metformin monotherapy followed by subsequent co-administration of a DPP-IV inhibitor (preferably vildagliptin or a pharmaceutically acceptable salt thereof) and metformin or a pharmaceutically acceptable salt thereof.

In another aspect, the invention relates to the use of metformin or a pharmaceutically acceptable salt thereof, in the manufacture of a medicament for improving glycaemic control in a patient with type 2 diabetes mellitus, wherein the metformin or a pharmaceutically acceptable salt thereof, is prepared for co-administered with vildagliptin or a pharmaceutically acceptable salt thereof, and wherein the improvement in glycaemic control is relative to metformin monotherapy followed by subsequent co-administration of a DPP-IV inhibitor (preferably vildagliptin or a pharmaceutically acceptable salt thereof) and metformin or a pharmaceutically acceptable salt thereof.

In another aspect, the invention relates to the use of metformin or a pharmaceutically acceptable salt thereof, in the manufacture of a medicament for improving glycaemic control in a patient with type 2 diabetes mellitus, wherein the metformin or a pharmaceutically acceptable salt thereof, is prepared for co-administration with a DPP-IV inhibitor (preferably vildagliptin or a pharmaceutically acceptable salt thereof), and wherein the improvement in glycaemic control is relative to metformin monotherapy, and the patient has not previously received pharmaceutical treatment for the type 2 diabetes mellitus.

In another aspect, the invention relates to the use of metformin or a pharmaceutically acceptable salt thereof, in the manufacture of a medicament for improving glycaemic control in a patient with type 2 diabetes mellitus, wherein the metformin or a pharmaceutically acceptable salt thereof, is prepared for co-administration with vildagliptin or a pharmaceutically acceptable salt thereof, and wherein the improvement in glycaemic control is relative to metformin monotherapy, and the patient has not previously received pharmaceutical treatment for the type 2 diabetes mellitus.

In another aspect, the invention relates to the use of metformin or a pharmaceutically acceptable salt thereof, in the manufacture of a medicament for improving glycaemic control in a patient with type 2 diabetes mellitus, wherein the metformin or a pharmaceutically acceptable salt thereof, is prepared for co-administration with a DPP-IV inhibitor (preferably vildagliptin or a pharmaceutically acceptable salt thereof), and wherein the improvement in glycaemic control is relative to metformin monotherapy followed by subsequent co-administration of a DPP-IV inhibitor (preferably vildagliptin or a pharmaceutically acceptable salt thereof) and metformin or a pharmaceutically acceptable salt thereof, and the patient has not previously received pharmaceutical treatment for the type 2 diabetes mellitus.

In another aspect, the invention relates to the use of metformin or a pharmaceutically acceptable salt thereof, in the manufacture of a medicament for improving glycaemic control in a patient with type 2 diabetes mellitus, wherein the metformin or a pharmaceutically acceptable salt thereof, is prepared for co-administration with vildagliptin or a pharmaceutically acceptable salt thereof, and wherein the improvement in glycaemic control is relative to metformin monotherapy followed by subsequent co-administration of a DPP-IV inhibitor (preferably vildagliptin or a pharmaceutically acceptable salt thereof) and metformin or a pharmaceutically acceptable salt thereof, and wherein the patient has not previously received pharmaceutical treatment for the type 2 diabetes mellitus.

In another aspect, the invention relates to the use of metformin or a pharmaceutically acceptable salt thereof, in the manufacture of a medicament for improving glycaemic control in a patient with type 2 diabetes mellitus, wherein the metformin or a pharmaceutically acceptable salt thereof, is prepared for co-administration with a DPP-IV inhibitor (preferably vildagliptin or a pharmaceutically acceptable salt thereof), and the patient has not previously received pharmaceutical treatment for the type 2 diabetes mellitus.

In another aspect, the invention relates to the use of metformin or a pharmaceutically acceptable salt thereof, in the manufacture of a medicament for improving glycaemic control in a patient with type 2 diabetes mellitus, wherein the metformin or a pharmaceutically acceptable salt thereof, is prepared for co-administration with vildagliptin or a pharmaceutically acceptable salt thereof, and wherein the patient has not previously received pharmaceutical treatment for the type 2 diabetes mellitus.

In another aspect, the invention relates to the use of metformin or a pharmaceutically acceptable salt thereof, in the manufacture of a medicament for delaying the increase of $HbA_{1c}$ to greater than or equal to 53 mmol/mol (7.0%) in a patient with type 2 diabetes mellitus, wherein the metformin or a pharmaceutically acceptable salt thereof, is prepared for co-administration with a DPP-IV inhibitor (preferably vildagliptin or a pharmaceutically acceptable salt thereof).

In another aspect, the invention relates to the use of metformin or a pharmaceutically acceptable salt thereof, in the manufacture of a medicament for increase of $HbA_{1c}$ to greater than or equal to 53 mmol/mol (7.0%) in a patient with type 2 diabetes mellitus, wherein the metformin or a pharmaceutically acceptable salt thereof, is prepared for co-administration with a DPP-IV inhibitor (preferably vildagliptin or a pharmaceutically acceptable salt thereof), and wherein the delay in the increase of $HbA_{1c}$ is relative to metformin monotherapy.

In another aspect, the invention relates to the use of metformin or a pharmaceutically acceptable salt thereof, in the manufacture of a medicament for delaying the increase of $HbA_{1c}$ to greater than or equal to 53 mmol/mol (7.0%) in a patient with type 2 diabetes mellitus, wherein the metformin or a pharmaceutically acceptable salt thereof, is prepared for co-administration with vildagliptin or a pharmaceutically acceptable salt thereof, and wherein the delay in the increase of $HbA_{1c}$ is relative to metformin monotherapy.

In another aspect, the invention relates to the use of metformin or a pharmaceutically acceptable salt thereof, in the manufacture of a medicament for delaying the increase of $HbA_{1c}$ to greater than or equal to 53 mmol/mol (7.0%) in a patient with type 2 diabetes mellitus, wherein the metformin or a pharmaceutically acceptable salt thereof, is prepared for co-administration with a DPP-IV inhibitor (preferably vildagliptin or a pharmaceutically acceptable salt thereof), and wherein the delay in the increase of $HbA_{1c}$ is relative to metformin monotherapy followed by subsequent co-administration of a DPP-IV inhibitor (preferably vildagliptin or a pharmaceutically acceptable salt thereof) and metformin.

In another aspect, the invention relates to the use of metformin or a pharmaceutically acceptable salt thereof, in the manufacture of a medicament for delaying the increase of $HbA_{1c}$ to greater than or equal to 53 mmol/mol (7.0%) in a patient with type 2 diabetes mellitus, wherein the metformin or a pharmaceutically acceptable salt thereof, is prepared for co-administration with vildagliptin or a pharmaceutically acceptable salt thereof, and wherein the delay in the increase of $HbA_{1c}$ is relative to metformin monotherapy followed by subsequent co-administration of a DPP-IV inhibitor (preferably vildagliptin or a pharmaceutically acceptable salt thereof) and metformin or a pharmaceutically acceptable salt thereof.

In another aspect, the invention relates to the use of metformin or a pharmaceutically acceptable salt thereof, in the manufacture of a medicament for delaying the increase of $HbA_{1c}$ to greater than or equal to 53 mmol/mol (7.0%) in a patient with type 2 diabetes mellitus, wherein the metformin or a pharmaceutically acceptable salt thereof, is prepared for co-administration with a DPP-IV inhibitor (preferably vildagliptin or a pharmaceutically acceptable salt thereof), and wherein the delay in the increase of $HbA_{1c}$ is relative to metformin monotherapy, and wherein the patient has not previously received pharmaceutical treatment for the type 2 diabetes mellitus.

In another aspect, the invention relates to the use of metformin or a pharmaceutically acceptable salt thereof, in the manufacture of a medicament for delaying the increase of $HbA_{1c}$ to greater than or equal to 53 mmol/mol (7.0%) in a patient with type 2 diabetes mellitus, wherein the metformin or a pharmaceutically acceptable salt thereof, is prepared for co-administration with vildagliptin or a pharmaceutically acceptable salt thereof, and wherein the delay in the increase of $HbA_{1c}$ is relative to metformin monotherapy, and wherein the patient has not previously received pharmaceutical treatment for the type 2 diabetes mellitus.

In another aspect, the invention relates to the use of metformin or a pharmaceutically acceptable salt thereof, in the manufacture of a medicament for delaying the increase of $HbA_{1c}$ to greater than or equal to 53 mmol/mol (7.0%) in a patient with type 2 diabetes mellitus, wherein the metformin or a pharmaceutically acceptable salt thereof, is prepared for co-administration with a DPP-IV inhibitor (preferably vildagliptin or a pharmaceutically acceptable salt thereof), and wherein the delay in the increase of $HbA_{1c}$ is relative to metformin monotherapy followed by subsequent co-administration of a DPP-IV inhibitor (preferably vildagliptin or a pharmaceutically acceptable salt thereof) and metformin or a pharmaceutically acceptable salt thereof, and wherein the patient has not previously received pharmaceutical treatment for the type 2 diabetes mellitus.

In another aspect, the invention relates to the use of metformin or a pharmaceutically acceptable salt thereof, in the manufacture of a medicament for delaying the increase of $HbA_{1c}$ to greater than or equal to 53 mmol/mol (7.0%) in a patient with type 2 diabetes mellitus, wherein the metformin or a pharmaceutically acceptable salt thereof, is prepared for co-administration with vildagliptin or a pharmaceutically acceptable salt thereof, and wherein the delay in the increase of $HbA_{1c}$ is relative to metformin monotherapy followed by subsequent co-administration of a DPP-IV inhibitor (preferably vildagliptin or a pharmaceutically acceptable salt thereof) and metformin or a pharmaceutically acceptable salt thereof, and wherein the patient has not previously received pharmaceutical treatment for the type 2 diabetes mellitus.

In another aspect, the invention relates to the use of metformin or a pharmaceutically acceptable salt thereof, in the manufacture of a medicament for delaying the increase of $HbA_{1c}$ to greater than or equal to 53 mmol/mol (7.0%) in a patient with type 2 diabetes mellitus, wherein the metformin or a pharmaceutically acceptable salt thereof, is prepared for co-administration with a DPP-IV inhibitor (preferably vildagliptin or a pharmaceutically acceptable salt thereof), and wherein the patient has not previously received pharmaceutical treatment for the type 2 diabetes mellitus.

In another aspect, the invention relates to the use of metformin or a pharmaceutically acceptable salt thereof, in the manufacture of a medicament for delaying the increase of $HbA_{1c}$ to greater than or equal to 53 mmol/mol (7.0%) in a patient with type 2 diabetes mellitus, wherein the metformin or a pharmaceutically acceptable salt thereof, is prepared for co-administration with vildagliptin or a pharmaceutically acceptable salt thereof, and wherein the patient has not previously received pharmaceutical treatment for the type 2 diabetes mellitus.

In another aspect, the invention relates to the use of metformin or a pharmaceutically acceptable salt thereof, in the manufacture of a medicament for increasing the time taken to reach an $HbA_{1c}$ measurement of greater than or equal to 53 mmol/mol (7.0%) in a patient with type 2 diabetes mellitus, and wherein the metformin or a pharmaceutically acceptable salt thereof, is prepared for co-administration with a DPP-IV inhibitor (preferably vildagliptin or a pharmaceutically acceptable salt thereof).

In another aspect, the invention relates to the use of metformin or a pharmaceutically acceptable salt thereof, in the manufacture of a medicament for increasing the time taken to reach an $HbA_{1c}$ measurement of greater than or equal to 53 mmol/mol (7.0%) in a patient with type 2 diabetes mellitus, wherein the increase is relative to metformin monotherapy, and wherein the metformin or a pharmaceutically acceptable salt thereof, is prepared for co-administration with a DPP-IV inhibitor (preferably vildagliptin or a pharmaceutically acceptable salt thereof).

In another aspect, the invention relates to the use of metformin or a pharmaceutically acceptable salt thereof, in the manufacture of a medicament for increasing the time taken to reach an $HbA_{1c}$ measurement of greater than or equal to 53 mmol/mol (7.0%) in a patient with type 2 diabetes mellitus, wherein the increase is relative to metformin monotherapy, and wherein the metformin or a pharmaceutically acceptable salt thereof, is prepared for co-administration with vildagliptin or a pharmaceutically acceptable salt thereof.

In another aspect, the invention relates to the use of metformin or a pharmaceutically acceptable salt thereof, in the manufacture of a medicament for increasing the time taken to reach an $HbA_{1c}$ measurement of greater than or equal to 53 mmol/mol (7.0%) in a patient with type 2 diabetes mellitus, wherein the increase is relative to metformin monotherapy followed by subsequent co-administration of a DPP-IV inhibitor (preferably vildagliptin or a pharmaceutically acceptable salt thereof) and metformin or a pharmaceutically acceptable salt thereof, and wherein the metformin or a pharmaceutically acceptable salt thereof, is prepared for co-administration with a DPP-IV inhibitor (preferably vildagliptin or a pharmaceutically acceptable salt thereof).

In another aspect, the invention relates to the use of metformin or a pharmaceutically acceptable salt thereof, in the manufacture of a medicament for increasing the time taken to reach an $HbA_{1c}$ measurement of greater than or equal to 53 mmol/mol (7.0%) in a patient with type 2 diabetes mellitus, wherein the increase is relative to metformin monotherapy followed by subsequent co-administration of a DPP-IV inhibitor (preferably vildagliptin or a pharmaceutically acceptable salt thereof) and metformin or a pharmaceutically acceptable salt thereof, and wherein the metformin or a pharmaceutically acceptable salt thereof, is prepared for co-administration with vildagliptin or a pharmaceutically acceptable salt thereof.

In another aspect, the invention relates to the use of metformin or a pharmaceutically acceptable salt thereof, in the manufacture of a medicament for increasing the time taken to reach an $HbA_{1c}$ measurement of greater than or equal to 53 mmol/mol (7.0%) in a patient with type 2 diabetes mellitus, wherein the increase is relative to metformin monotherapy, and wherein the metformin or a pharmaceutically acceptable salt thereof, is prepared for co-administration with a DPP-IV inhibitor (preferably vildagliptin or a pharmaceutically acceptable salt thereof), and wherein the patient has not previously received pharmaceutical treatment for the type 2 diabetes mellitus.

In another aspect, the invention relates to the use of metformin or a pharmaceutically acceptable salt thereof, in the manufacture of a medicament for increasing the time taken to reach an $HbA_{1c}$ measurement of greater than or equal to 53 mmol/mol (7.0%) in a patient with type 2 diabetes mellitus, wherein the increase is relative to metformin monotherapy, and wherein the metformin or a pharmaceutically acceptable salt thereof, is prepared for co-administration with vildagliptin or a pharmaceutically acceptable salt thereof, and wherein the patient has not previously received pharmaceutical treatment for the type 2 diabetes mellitus.

In another aspect, the invention relates to the use of metformin or a pharmaceutically acceptable salt thereof, in the manufacture of a medicament for increasing the time taken to reach an $HbA_{1c}$ measurement of greater than or equal to 53 mmol/mol (7.0%) in a patient with type 2 diabetes mellitus, wherein the increase is relative to metformin monotherapy followed by subsequent co-administration of a DPP-IV inhibitor (preferably vildagliptin or a pharmaceutically acceptable salt thereof) and metformin or a pharmaceutically acceptable salt thereof, and wherein the metformin or a pharmaceutically acceptable salt thereof, is prepared for co-administration with a DPP-IV inhibitor (preferably vildagliptin or a pharmaceutically acceptable salt thereof), and wherein the patient has not previously received pharmaceutical treatment for the type 2 diabetes mellitus.

In another aspect, the invention relates to the use of metformin or a pharmaceutically acceptable salt thereof, in the manufacture of a medicament for increasing the time taken to reach an $HbA_{1c}$ measurement of greater than or equal to 53 mmol/mol (7.0%) in a patient with type 2 diabetes mellitus, wherein the increase is relative to metformin monotherapy followed by subsequent co-administration of a DPP-IV inhibitor (preferably vildagliptin or a pharmaceutically acceptable salt thereof) and metformin or a pharmaceutically acceptable salt thereof, and wherein the metformin or a pharmaceutically acceptable salt thereof, is prepared for co-administration with vildagliptin or a pharmaceutically acceptable salt thereof, and wherein the patient has not previously received pharmaceutical treatment for the type 2 diabetes mellitus.

In another aspect, the invention relates to the use of metformin or a pharmaceutically acceptable salt thereof, in the manufacture of a medicament for increasing the time taken to reach an $HbA_{1c}$ measurement of greater than or equal to 53 mmol/mol (7.0%) in a patient with type 2 diabetes mellitus, wherein the patient has not previously received pharmaceutical treatment for the type 2 diabetes mellitus, and wherein the metformin or a pharmaceutically acceptable salt thereof, is prepared for co-administration with a DPP-IV inhibitor (preferably vildagliptin or a pharmaceutically acceptable salt thereof).

In another aspect, the invention relates to the use of metformin or a pharmaceutically acceptable salt thereof, in the manufacture of a medicament for increasing the time taken to reach an $HbA_{1c}$ measurement of greater than or equal to 53 mmol/mol (7.0%) in a patient with type 2 diabetes mellitus, wherein the patient has not previously received pharmaceutical treatment for the type 2 diabetes mellitus, and wherein the metformin or a pharmaceutically acceptable salt thereof, is prepared for co-administration with vildagliptin or a pharmaceutically acceptable salt thereof.

In another aspect, the invention relates to the use of metformin or a pharmaceutically acceptable salt thereof, in the manufacture of a medicament for preventing loss of glycaemic control in a patient with type 2 diabetes mellitus, wherein the metformin or a pharmaceutically acceptable salt thereof, is prepared for co-administration with a DPP-IV inhibitor (preferably vildagliptin or a pharmaceutically acceptable salt thereof).

In another aspect, the invention relates to the use of metformin or a pharmaceutically acceptable salt thereof, in the manufacture of a medicament for preventing loss of glycaemic control in a patient with type 2 diabetes mellitus, wherein the metformin or a pharmaceutically acceptable salt thereof, is prepared for co-administration with vildagliptin or a pharmaceutically acceptable salt thereof.

In another aspect, the invention relates to the use of metformin or a pharmaceutically acceptable salt thereof, in the manufacture of a medicament for preventing loss of glycaemic control in a patient with type 2 diabetes mellitus, wherein the metformin or a pharmaceutically acceptable salt thereof, is prepared for co-administration with a DPP-IV inhibitor (preferably vildagliptin or a pharmaceutically acceptable salt thereof), and wherein the patient has not previously received pharmaceutical treatment for the type 2 diabetes mellitus.

In another aspect, the invention relates to the use of metformin or a pharmaceutically acceptable salt thereof, in the manufacture of a medicament for preventing loss of glycaemic control in a patient with type 2 diabetes mellitus, wherein the metformin or a pharmaceutically acceptable salt thereof, is prepared for co-administration with vildagliptin or a pharmaceutically acceptable salt thereof, and wherein the patient has not previously received pharmaceutical treatment for the type 2 diabetes mellitus.

In another aspect, the invention relates to the use of metformin or a pharmaceutically acceptable salt thereof, in the manufacture of a medicament for reducing the risk of a cardiovascular event in a patient undergoing treatment for type 2 diabetes mellitus, wherein the metformin or a pharmaceutically acceptable salt thereof, is prepared for co-administration with a DPP-IV inhibitor (preferably vildagliptin or a pharmaceutically acceptable salt thereof).

In another aspect, the invention relates to the use of metformin or a pharmaceutically acceptable salt thereof, in the manufacture of a medicament for reducing the risk of a cardiovascular event in a patient undergoing treatment for type 2 diabetes mellitus, wherein the metformin or a pharmaceutically acceptable salt thereof, is prepared for co-administration with vildagliptin or a pharmaceutically acceptable salt thereof.

In another aspect, the invention relates to the use of metformin or a pharmaceutically acceptable salt thereof, in the manufacture of a medicament for reducing the risk of a cardiovascular event in a patient undergoing treatment for type 2 diabetes mellitus, wherein the metformin or a pharmaceutically acceptable salt thereof, is prepared for co-administration with a DPP-IV inhibitor (preferably vildagliptin or a pharmaceutically acceptable salt thereof), and wherein the patient has not previously received pharmaceutical treatment for the type 2 diabetes mellitus.

In another aspect, the invention relates to the use of metformin or a pharmaceutically acceptable salt thereof, in the manufacture of a medicament for reducing the risk of a cardiovascular event in a patient undergoing treatment for type 2 diabetes mellitus, wherein the metformin or a pharmaceutically acceptable salt thereof, is prepared for co-administration with vildagliptin or a pharmaceutically acceptable salt thereof, and wherein the patient has not previously received pharmaceutical treatment for the type 2 diabetes mellitus.

In another aspect, the invention relates to the use of metformin or a pharmaceutically acceptable salt thereof, in the manufacture of a medicament for reducing the risk of a cardiovascular event in a patient undergoing treatment for type 2 diabetes mellitus, wherein the metformin or a pharmaceutically acceptable salt thereof, is prepared for co-administration with a DPP-IV inhibitor (preferably vildagliptin or a pharmaceutically acceptable salt thereof), and wherein the risk of a cardiovascular event is reduced relative to metformin monotherapy.

In another aspect, the invention relates to the use of metformin or a pharmaceutically acceptable salt thereof, in the manufacture of a medicament for reducing the risk of a cardiovascular event in a patient undergoing treatment for type 2 diabetes mellitus, wherein the metformin or a pharmaceutically acceptable salt thereof, is prepared for co-administration with vildagliptin or a pharmaceutically acceptable salt thereof, and wherein the risk of a cardiovascular event is reduced relative to metformin monotherapy.

In another aspect, the invention relates to the use of metformin or a pharmaceutically acceptable salt thereof, in the manufacture of a medicament for reducing the risk of a cardiovascular event in a patient undergoing treatment for type 2 diabetes mellitus, wherein the metformin or a pharmaceutically acceptable salt thereof, is prepared for co-administration with a DPP-IV inhibitor (preferably vildagliptin or a pharmaceutically acceptable salt thereof), and wherein the risk of a cardiovascular event is reduced relative to metformin monotherapy followed by subsequent co-administration of a DPP-IV inhibitor (preferably vildagliptin or a pharmaceutically acceptable salt thereof) and metformin or a pharmaceutically acceptable salt thereof.

In another aspect, the invention relates to the use of metformin or a pharmaceutically acceptable salt thereof, in the manufacture of a medicament for reducing the risk of a cardiovascular event in a patient undergoing treatment for type 2 diabetes mellitus, wherein the metformin or a pharmaceutically acceptable salt thereof, is prepared for co-administration with vildagliptin or a pharmaceutically acceptable salt thereof, and wherein the risk of a cardiovascular event is reduced relative to metformin monotherapy followed by subsequent co-administration of a DPP-IV inhibitor (preferably vildagliptin or a pharmaceutically acceptable salt thereof) and metformin or a pharmaceutically acceptable salt thereof.

In another aspect, the invention relates to the use of metformin or a pharmaceutically acceptable salt thereof, in the manufacture of a medicament for reducing the risk of a cardiovascular event in a patient undergoing treatment for type 2 diabetes mellitus, wherein the metformin or a pharmaceutically acceptable salt thereof, is prepared for co-administration with a DPP-IV inhibitor (preferably vildagliptin or a pharmaceutically acceptable salt thereof), and wherein the risk of a cardiovascular event is reduced relative to metformin monotherapy, and wherein the patient has not previously received pharmaceutical treatment for the type 2 diabetes mellitus.

In another aspect, the invention relates to the use of metformin or a pharmaceutically acceptable salt thereof, in the manufacture of a medicament for reducing the risk of a cardiovascular event in a patient undergoing treatment for type 2 diabetes mellitus, wherein the metformin or a pharmaceutically acceptable salt thereof, is prepared for co-administration with vildagliptin or a pharmaceutically acceptable salt thereof, and wherein the risk of a cardiovascular event is reduced relative to metformin monotherapy, and wherein the patient has not previously received pharmaceutical treatment for the type 2 diabetes mellitus.

In another aspect, the invention relates to the use of metformin or a pharmaceutically acceptable salt thereof, in the manufacture of a medicament for reducing the risk of a cardiovascular event in a patient undergoing treatment for type 2 diabetes mellitus, wherein the metformin or a pharmaceutically acceptable salt thereof, is prepared for co-administration with a DPP-IV inhibitor (preferably vildagliptin or a pharmaceutically acceptable salt thereof), and wherein the risk of a cardiovascular event is reduced relative to metformin monotherapy followed by subsequent co-administration of a DPP-IV inhibitor (preferably vildagliptin or a pharmaceutically acceptable salt thereof) and metformin or a pharmaceutically acceptable salt thereof, and wherein the patient has not previously received pharmaceutical treatment for the type 2 diabetes mellitus.

In another aspect, the invention relates to the use of metformin or a pharmaceutically acceptable salt thereof, in the manufacture of a medicament for reducing the risk of a cardiovascular event in a patient undergoing treatment for type 2 diabetes mellitus, wherein the metformin or a pharmaceutically acceptable salt thereof, is prepared for co-administration with vildagliptin or a pharmaceutically acceptable salt thereof, and wherein the risk of a cardiovascular event is reduced relative to metformin monotherapy followed by subsequent co-administration of a DPP-IV inhibitor (preferably vildagliptin or a pharmaceutically acceptable salt thereof) and metformin or a pharmaceutically acceptable salt thereof, and wherein the patient has not previously received pharmaceutical treatment for the type 2 diabetes mellitus.

In another aspect, the invention relates to the use of metformin or a pharmaceutically acceptable salt thereof, in the manufacture of a medicament for treating type 2 diabetes mellitus without concomitant administration of insulin, and wherein the metformin or a pharmaceutically acceptable salt thereof, is prepared for co-administration with DPP-IV inhibitor (preferably vildagliptin or a pharmaceutically acceptable salt thereof).

In another aspect, the invention relates to the use of metformin or a pharmaceutically acceptable salt thereof, in the manufacture of a medicament for treating type 2 diabetes mellitus without concomitant administration of insulin, wherein the metformin or a pharmaceutically acceptable salt thereof, is prepared for co-administration with vildagliptin or a pharmaceutically acceptable salt thereof.

In another aspect, the invention relates to the use of metformin or a pharmaceutically acceptable salt thereof, in the manufacture of a medicament for treating type 2 diabetes mellitus without concomitant administration of insulin, and wherein the metformin or a pharmaceutically acceptable salt thereof, is prepared for co-administration with DPP-IV inhibitor (preferably vildagliptin or a pharmaceutically acceptable salt thereof), wherein the patient has not previously received pharmaceutical treatment for the type 2 diabetes mellitus.

In another aspect, the invention relates to the use of metformin or a pharmaceutically acceptable salt thereof, in the manufacture of a medicament for treating type 2 diabetes mellitus without concomitant administration of insulin, wherein the metformin or a pharmaceutically acceptable salt thereof, is prepared for co-administration with vildagliptin or a pharmaceutically acceptable salt thereof, wherein the patient has not previously received pharmaceutical treatment for the type 2 diabetes mellitus.

DETAILED DESCRIPTION OF THE INVENTION

Figure 1:
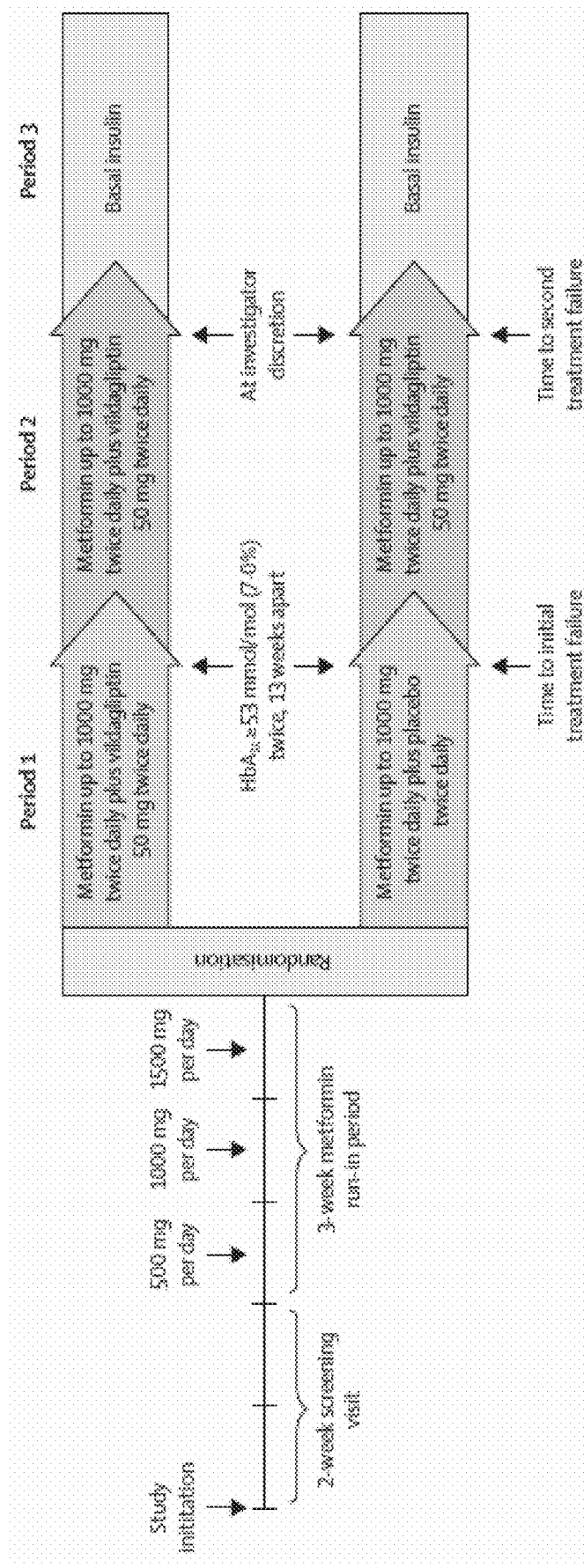
FIG. 1 is a diagram of the VERIFY study design.

Preferred embodiments of the invention are defined below. These preferred embodiments are applicable to all of the aspects of the invention defined above.

Patient Population

In one embodiment, the patient has been diagnosed with type 2 diabetes mellitus for less than 2 years prior to the beginning of treatment. In one embodiment, the patient has not previously received pharmaceutical treatment for the type 2 diabetes mellitus. In one embodiment, the patient has not been previously treated with metformin or a pharmaceutically acceptable salt thereof.

In one embodiment, the patient has been diagnosed with type 2 diabetes mellitus for less than 2 years prior to the beginning of treatment and the patient has not previously received pharmaceutical treatment for the type 2 diabetes mellitus. In one embodiment, the patient has been diagnosed with type 2 diabetes mellitus for less than 2 years prior to the beginning of treatment and the patient has not been previously treated with metformin or a pharmaceutically acceptable salt thereof.

In one embodiment, the patient has received metformin monotherapy for no longer than 12 months prior to the beginning of combination therapy. In one embodiment, the patient has received metformin monotherapy for no longer than 6 months prior to the beginning of combination therapy. In one embodiment, the patient has received metformin monotherapy for no longer than 3 months prior to the beginning of combination therapy. In one embodiment, the patient has received metformin monotherapy for no longer than 1 month prior to the beginning of combination therapy. Preferably, the patient has not been previously treated with metformin or a pharmaceutically acceptable salt thereof prior to the beginning of combination therapy.

In one embodiment, the combination therapy is commenced within 24 months of a diagnosis of type 2 diabetes mellitus. In one embodiment, the combination therapy is commenced within 12 months of a diagnosis of type 2 diabetes mellitus. In one embodiment, the combination therapy is commenced within 6 months of a diagnosis of type 2 diabetes mellitus. In one embodiment, the combination therapy is commenced within 3 months of a diagnosis of type 2 diabetes mellitus. In one embodiment, the combination therapy is commenced within 1 month of a diagnosis of type 2 diabetes mellitus.

In one embodiment, the combination therapy is commenced within 24 months of the first measured $HbA_{1c}$ level of greater than or equal to 53 mmol/mol (7.0%) in a patient. In one embodiment, the combination therapy is commenced within 12 months of the first measured $HbA_{1c}$ level of greater than or equal to 53 mmol/mol (7.0%) in a patient. In one embodiment, the combination therapy is commenced within 6 months of the first measured $HbA_{1c}$ level of greater than or equal to 53 mmol/mol (7.0%) in a patient. In one embodiment, the combination therapy is commenced within 3 months of the first measured $HbA_{1c}$ level of greater than or equal to 53 mmol/mol (7.0%) in a patient. In one embodiment, the combination therapy is commenced within 1 month of the first measured $HbA_{1c}$ level of greater than or equal to 53 mmol/mol (7.0%) in a patient.

Clinical Outcomes

In one embodiment, the delayed loss of glycaemic control in a patient with type 2 diabetes mellitus is relative to metformin monotherapy. In one embodiment, the delayed loss of glycaemic control in a patient with type 2 diabetes mellitus occurs without concomitant administration of insulin to the patient. In one embodiment, the delayed loss of glycaemic control in a patient with type 2 diabetes mellitus is relative to metformin monotherapy followed by subsequent co-administration of a DPP-IV inhibitor and metformin or a pharmaceutically acceptable salt thereof. In one embodiment, the delayed loss of glycaemic control in a patient with type 2 diabetes mellitus is relative to metformin monotherapy followed by subsequent co-administration of vildagliptin or a pharmaceutically acceptable salt thereof and metformin or a pharmaceutically acceptable salt thereof. In one embodiment, the patient has not previously received pharmaceutical treatment for the type 2 diabetes mellitus. In one embodiment, the delay in loss of glycaemic control lasts for 5 years or more.

In one embodiment, the improvement in glycaemic control in a patient with type 2 diabetes mellitus is relative to metformin monotherapy. In one embodiment, the improvement in glycaemic control in a patient with type 2 diabetes mellitus occurs without concomitant administration of insulin to the patient. In one embodiment, the improvement in glycaemic control in a patient with type 2 diabetes mellitus is relative to metformin monotherapy followed by subsequent co-administration of a DPP-IV inhibitor and metformin or a pharmaceutically acceptable salt thereof. In one embodiment, the improvement in glycaemic control in a patient with type 2 diabetes mellitus is relative to metformin monotherapy followed by subsequent co-administration of vildagliptin or a pharmaceutically acceptable salt thereof, and metformin or a pharmaceutically acceptable salt thereof, or a pharmaceutically acceptable salt thereof. In one embodiment, the patient has not previously received pharmaceutical treatment for the type 2 diabetes mellitus. In one embodiment, the improvement in glycaemic control lasts for 5 years or more.

In one embodiment, the delay in the increase of $HbA_{1c}$ to greater than or equal to 53 mmol/mol (7.0%) in a patient with type 2 diabetes mellitus occurs relative to metformin monotherapy. In one embodiment, the delay in the increase of $HbA_{1c}$ to greater than or equal to 53 mmol/mol (7.0%) in a patient with type 2 diabetes mellitus occurs without concomitant administration of insulin to the patient. In one embodiment, the delay in the increase of $HbA_{1c}$ to greater than or equal to 53 mmol/mol (7.0%) in a patient with type 2 diabetes mellitus is relative to metformin monotherapy followed by subsequent co-administration of a DPP-IV inhibitor and metformin or a pharmaceutically acceptable salt thereof. In one embodiment, the delay in the increase of $HbA_{1c}$ to greater than or equal to 53 mmol/mol (7.0%) in a patient with type 2 diabetes mellitus is relative to metformin monotherapy followed by subsequent co-administration of vildagliptin or a pharmaceutically acceptable salt thereof, and metformin or a pharmaceutically acceptable salt thereof. In one embodiment, the patient has not previously received pharmaceutical treatment for the type 2 diabetes mellitus. In one embodiment, the delay in the increase of $HbA_{1c}$ last for 5 years or more.

In one embodiment, the increase in the time taken to reach an $HbA_{1c}$ measurement of greater than or equal to 53 mmol/mol (7.0%) in a patient with type 2 diabetes mellitus is relative to metformin monotherapy. In one embodiment, the increase in the time taken to reach an $HbA_{1c}$ measurement of greater than or equal to 53 mmol/mol (7.0%) in a patient with type 2 diabetes mellitus occurs without concomitant administration of insulin to the patient. In one embodiment, the increase in the time taken to reach an $HbA_{1c}$ measurement of greater than or equal to 53 mmol/mol (7.0%) in a patient with type 2 diabetes mellitus is relative to metformin monotherapy followed by subsequent co-administration of a DPP-IV inhibitor and metformin or a pharmaceutically acceptable salt thereof. In one embodiment, the increase in the time taken to reach an $HbA_{1c}$ measurement of greater than or equal to 53 mmol/mol (7.0%) in a patient with type 2 diabetes mellitus is relative to metformin monotherapy followed by subsequent co-administration of vildagliptin or a pharmaceutically acceptable salt thereof, and metformin or a pharmaceutically acceptable salt thereof. In one embodiment, the patient has not previously received pharmaceutical treatment for the type 2 diabetes mellitus.

In one embodiment, the method does not comprises the administration of insulin to the patient. In another embodiment, the method comprises administration of insulin in combination with vildagliptin or a pharmaceutically acceptable salt thereof, and metformin or a pharmaceutically acceptable salt thereof. In one embodiment, the patient has not previously received pharmaceutical treatment for the type 2 diabetes mellitus.

In one embodiment, the method comprises a first phase and a second phase. The first phase comprises the administration of vildagliptin or a pharmaceutically acceptable salt thereof, and metformin or a pharmaceutically acceptable salt thereof, as defined above, and does not comprises the administration of insulin. The second phase comprises the administration of vildagliptin or a pharmaceutically acceptable salt thereof, and metformin or a pharmaceutically acceptable salt thereof, and insulin. In one embodiment, the patient transitions from the first phase to the second phase if/when the patient's glycaemic levels cease to be adequately controlled (for example, when the patient's HbA$_{1c}$ increases to greater than or equal to 53 mmol/mol (7.0%)). In one embodiment, the patient has not previously received pharmaceutical treatment for the type 2 diabetes mellitus when the first phase begins.

Safety and Adverse Events

In one embodiment, the method reduces the risk of the patient having type 2 diabetes mellitus experiencing an adverse event. In one embodiment, the method does not increase the risk of a patient experiencing an adverse event. In one embodiment, the method does not increase the risk of a patient experiencing an adverse event relative to metformin monotherapy. In one embodiment, the method does not increase the risk of a patient experiencing an adverse event relative to metformin monotherapy followed by subsequent co-administration of a DPP-IV inhibitor and metformin or a pharmaceutically acceptable salt thereof. In one embodiment the method does not increase the risk of a patient experiencing an adverse event relative to metformin monotherapy followed by subsequent co-administration of vildagliptin or a pharmaceutically acceptable salt thereof, and metformin or a pharmaceutically acceptable salt thereof. In one embodiment, the patient has not previously received pharmaceutical treatment for the type 2 diabetes mellitus.

In one embodiment, the method does not increase the patient's risk of hypoglycaemia. In one embodiment, the method does not increase the patient's risk of pancreatitis. In one embodiment, the method does not increase the patient's risk of pancreatic carcinoma. In one embodiment, the method does not increase the patient's risk of neoplasms. In one embodiment, the method does not increase the patient's risk of bullous pemphigoids. In one embodiment, the patient has not previously received pharmaceutical treatment for the type 2 diabetes mellitus.

In one embodiment, the method does not increase the patient's risk of hypoglycaemia relative to metformin monotherapy. In one embodiment, the method does not increase the patient's risk of pancreatitis relative to metformin monotherapy. In one embodiment, the method does not increase the patient's risk of pancreatic carcinoma relative to metformin monotherapy. In one embodiment, the method does not increase the patient's risk of neoplasms relative to metformin monotherapy. In one embodiment, the method does not increase the patient's risk of bullous pemphigoids relative to metformin monotherapy. In one embodiment, the patient has not previously received pharmaceutical treatment for the type 2 diabetes mellitus.

In one embodiment, the method does not increase the patient's risk of hypoglycaemia relative to metformin monotherapy followed by subsequent co-administration of a DPP-IV inhibitor and metformin or a pharmaceutically acceptable salt thereof. In one embodiment, the method does not increase the patient's risk of pancreatitis relative to metformin monotherapy followed by subsequent co-administration of a DPP-IV inhibitor and metformin or a pharmaceutically acceptable salt thereof. In one embodiment, the method does not increase the patient's risk of pancreatic carcinoma relative to metformin monotherapy followed by subsequent co-administration of a DPP-IV inhibitor and metformin or a pharmaceutically acceptable salt thereof. In one embodiment, the method does not increase the patient's risk of neoplasms relative to metformin monotherapy followed by subsequent co-administration of a DPP-IV inhibitor and metformin or a pharmaceutically acceptable salt thereof. In one embodiment, the method does not increase the patient's risk of bullous pemphigoids relative to metformin monotherapy followed by subsequent co-administration of a DPP-IV inhibitor and metformin or a pharmaceutically acceptable salt thereof. In one embodiment, the patient has not previously received pharmaceutical treatment for the type 2 diabetes mellitus.

In one embodiment, the method reduces the risk of the patient experiencing a cardiovascular event. In one embodiment, the cardiovascular event is a macrovascular event. In one embodiment, the macrovascular event is selected from the group consisting of cardiovascular death, non-fatal myocardial infarction or stroke, and hospital admission for heart failure. In one embodiment, the macrovascular event is cardiovascular death. In one embodiment, the macrovascular event is non-fatal myocardial infarction. In one embodiment, the macrovascular event is stroke. In one embodiment, the macrovascular event is hospital admission for heart failure. In one embodiment, the patient has not previously received pharmaceutical treatment for the type 2 diabetes mellitus.

In one embodiment, the risk of experiencing a cardiovascular event is reduced relative to metformin monotherapy. In one embodiment, the risk of experiencing a cardiovascular event is reduced relative to metformin monotherapy followed by subsequent co-administration of a DPP-IV inhibitor and metformin or a pharmaceutically acceptable salt thereof. In one embodiment, the risk of experiencing a cardiovascular event is reduced relative to metformin monotherapy followed by subsequent co-administration of vildagliptin or a pharmaceutically acceptable salt thereof, and metformin or a pharmaceutically acceptable salt thereof. In one embodiment, the patient has not previously received pharmaceutical treatment for the type 2 diabetes mellitus.

Metformin

Metformin is the International Nonproprietary Name (INN) for the compound N,N-dimethylbiguanide. Metformin has the structure depicted below.

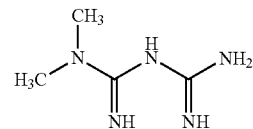

Metformin is commercially available, for example in the form of the product GLUCOPHAGE®. It is also available in a fixed-dose combination with vildagliptin as, for example, the product Eucreas®. In the present invention, metformin may be administered in free base form or in the form of a pharmaceutically acceptable salt. Preferably, metformin is administered as metformin hydrochloride. As used herein, dosages of metformin expressed in mg (milligrams) refer to amounts of metformin hydrochloride, unless stated otherwise.

DPP-IV Inhibitors

Dipeptidyl pepidase-IV inhibitors ("DPP-IV inhibitors") are a class of drugs which are known to treat type 2 diabetes mellitus by inhibition of the enzyme dipeptidyl peptidase-IV. Without wishing to be bound by theory, it is believed that DPP-IV inhibitors act to increase incretin (GLP-1 and GIP) in vivo, and that this results in inhibited glucagon release and increased insulin secretion, decreased gastric emptying, and decreased blood glucose levels. Inhibitors of DPP-IV can be readily identified by the skilled person. For example, DPP-IV inhibitors may be identified by the skilled person using the "DPP (IV) Screening Assay Kit", which is commercially available from Cayman Chemical (Item No. 700210).

Any entity (e.g. a small molecule, or a larger molecule such as a peptide, protein, or antibody) which is able to inhibit the DPP-IV enzyme may be used in the present invention. The DPP-IV inhibitor may be administered as a free base compound, or it may be administered as a pharmaceutically acceptable salt of the free base. Specific DPP-IV inhibitors which may be used in the present invention include, but are not limited to, sitagliptin, vildagliptin, saxagliptin, linagliptin, gemigliptin, anagliptin, tenegliptin, alogliptin, trelagliptin, omarigliptin, evogliptin, gosogliptin, dutogliptin, and pharmaceutically acceptable salts thereof. Preferably, the DPP-IV inhibitor used in the present invention is vildagliptin or a pharmaceutically acceptable salt thereof.

Vildagliptin

Vildagliptin is the INN of the compound (2S)-1-{2-[(3-hydroxy-1-adamantyl)amino]acetyl}pyrrolidine-2-carbonitrile. Vildagliptin has the structure depicted below.

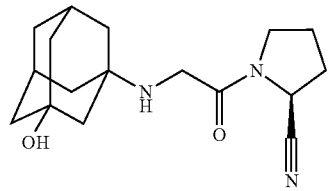 [SMILES: N#C[C@@H]1CCCN1C(=O)CNC12CC3CC(CC(O)(C3)C1)C2]

Vildagliptin is commercially available, for example as the product Galvus®. It is also available in a fixed-dose combination with metformin as, for example, the product Eucreas®. In the invention, vildagliptin may be administered as a free base or in the form of a pharmaceutically acceptable salt (e.g. vildagliptin hydrochloride). Preferably, vildagliptin is administered as a free base compound. As used herein, doses of vildagliptin expressed in mg (milligrams) refer to amounts of vildagliptin free base, unless stated otherwise.

Sitagliptin

Sitagliptin is the INN of the compound 4-oxo-4-(3-(trifluoromethyl)-5,6-dihydro(1,2,4)triazolo(4,3-a)pyrazin-7(8H)-yl)-1-(2,4,5-trifluorophenyl)butan-2-amine. Sitagliptin has the structure depicted below:

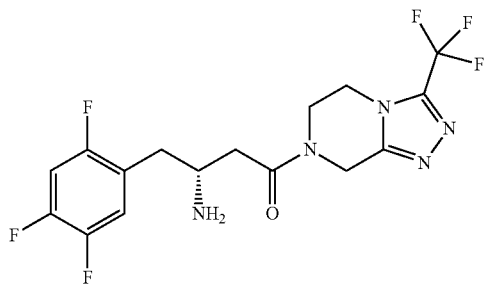 [SMILES: N[C@@H](CC(=O)N1CCn2c(nnc2C(F)(F)F)C1)Cc1cc(F)c(F)cc1F]

Sitagliptin is commercially available, for example, as the product Januvia®. It is also available in a fixed-dose combination with metformin as, for example, the product Janumet®. In the invention, sitagliptin may be administered as a free base or in the form of a pharmaceutically acceptable salt. Preferably, sitagliptin is administered as a phosphate monohydrate salt. As used herein, doses of sitagliptin expressed in mg (milligrams) refer to amounts of sitagliptin free base, unless stated otherwise.

In some embodiments of the invention, sitagliptin or a pharmaceutically acceptable salt thereof, is co-administered with metformin, or a pharmaceutically acceptable salt thereof. In one embodiment, sitagliptin or a pharmaceutically acceptable salt thereof is administered at a dose of 100 mg per day.

Saxagliptin

Saxagliptin is the INN of the compound (1S,3S,5S)-2-[(2S)-2-amino-2-(3-hydroxyadamantan-1-yl)acetyl]-2-azabicyclo[3.1.0]hexane-3-carbonitrile. Saxagliptin has the structure depicted below:

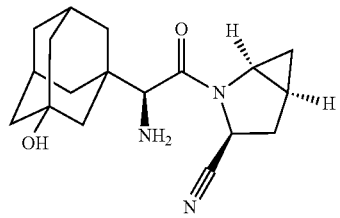 [SMILES: N#C[C@@H]1C[C@@H]2C[C@@H]2N1C(=O)[C@@H](N)C12CC3CC(CC(O)(C3)C1)C2]

Saxagliptin is commercially available, for example, as the product Onglyza®. It is also available as a fixed-dose combination with metformin as, for example, the product Kombiglyze XR® (marketed under the trade name Komboglyze® in the European Union). It is also available as a fixed-dose combination with dapagliflozin as, for example, the product Qtern®. In the invention, saxagliptin is administered as a free base or in the form of a pharmaceutically acceptable salt. Preferably, saxagliptin is administered as the hydrochloride salt. As used herein, doses of saxagliptin expressed in mg (milligrams) refer to amounts of saxagliptin free base, unless stated otherwise.

In some embodiments of the invention, saxagliptin or a pharmaceutically acceptable salt thereof, is co-administered with metformin, or a pharmaceutically acceptable salt thereof. In one embodiment, saxagliptin or a pharmaceutically acceptable salt thereof is administered at a dose of 2.5 mg or 5 mg once daily.

Linagliptin

Linagliptin is the INN of the compound 8-[(3R)-3-aminopiperidin-1-yl]-7-but-2-ynyl-3-methyl-1-[(4-methylquinazolin-2-yl)methyl]purine-2,6-dione. Linagliptin has the structure depicted below:

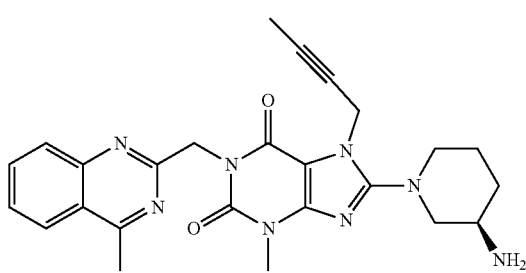 [SMILES: CC#CCn1c(N2CCC[C@@H](N)C2)nc2c1c(=O)n(Cc1nc(C)c3ccccc3n1)c(=O)n2C]

Linagliptin is commercially available, for example, as the product Tradjenta®. It is also available as a fixed-dose combination with metformin as, for example, the products Jentadueto® and Jentaduento XR®. It is also available as a fixed-dose combination with empagliflozin in the product Glyxambi®. In the invention, linagliptin may be administered as a free base or in the form of a pharmaceutically acceptable salt (e.g. linagliptin hydrochloride). Preferably, linagliptin is administered as a free base compound. As used herein, doses of linagliptin expressed in mg (milligrams) refer to amounts of linagliptin free base, unless stated otherwise.

In some embodiments of the invention, linagliptin or a pharmaceutically acceptable salt thereof, is co-administered with metformin, or a pharmaceutically acceptable salt thereof. In one embodiment, linagliptin or a pharmaceutically acceptable salt thereof is administered at a dose of 5 mg once daily.

Alogliptin

Alopgliptin is the INN of the compound 2-[[6-[(3R)-3-aminopiperidin-1-yl]-3-methyl-2,4-dioxopyrimidin-1-yl] methyl]benzonitrile. Alogliptin has the structure depicted below:

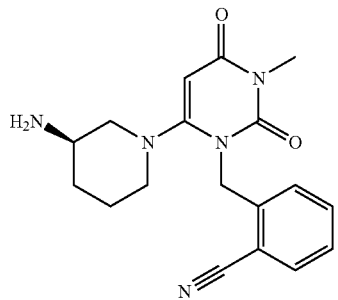 [SMILES: Cn1c(=O)cc(N2CCC[C@@H](N)C2)n(Cc2ccccc2C#N)c1=O]

Alogliptin is commercially available, for example, as the product Nesina® (marketed under the trade name Vipidia® in the European Union). It is also available as a fixed-dose combination with metformin as, for example, the product Kazano® (marketed under the trade name Vipdomet® in the European Union). It is also available as a fixed-dose combination with pioglitazone as, for example, the product Oseni® (marketed as Incresync® in the European Union). In the invention, alogliptin may be administered as a free base or in the form of a pharmaceutically acceptable salt (e.g. alogliptin benzoate). Preferably, alogliptin is administered as the benzoate salt. As used herein, doses of alogliptin expressed in mg (milligrams) refer to amounts of alogliptin free base, unless stated otherwise.

In some embodiments of the invention, alogliptin or a pharmaceutically acceptable salt thereof, is co-administered with metformin, or a pharmaceutically acceptable salt thereof. In one embodiment, alogliptin or a pharmaceutically acceptable salt thereof is administered at a dose of 25 mg once daily.

Combinations

In one embodiment, the combination of vildagliptin or a pharmaceutically acceptable salt thereof, and metformin or a pharmaceutically acceptable salt thereof is comprised within a single oral dosage form. In one embodiment, the oral dosage form is a tablet, capsule, powder or granule. In one embodiment, the oral dosage form is a tablet. In one embodiment, the tablet is a fixed-dose combination tablet. In one embodiment, the fixed-dose combination tablet comprises 50 mg vildagliptin or a pharmaceutically acceptable salt thereof (preferably vildagliptin free base) and 850 mg metformin or a pharmaceutically acceptable salt thereof (preferably metformin hydrochloride). In one embodiment, the fixed-dose combination tablet comprises 50 mg vildagliptin or a pharmaceutically acceptable salt thereof (preferably vildagliptin free base) and 1000 mg metformin or a pharmaceutically acceptable salt thereof (preferably metformin hydrochloride). In one embodiment, the fixed-dose combination tablet comprises 50 mg vildagliptin or a pharmaceutically acceptable salt thereof (preferably vildagliptin free base) and 500 mg metformin or a pharmaceutically acceptable salt thereof (preferably metformin hydrochloride). In one embodiment, the fixed-dose combination tablet is a Eucreas® tablet.

In one embodiment, the combination of vildagliptin or a pharmaceutically acceptable salt thereof, and metformin or a pharmaceutically acceptable salt thereof is made up of a first oral dosage form comprising vildagliptin or a pharmaceutically acceptable salt thereof, and a second, separate oral dosage form comprising metformin or a pharmaceutically acceptable salt thereof. In one embodiment, one or both of the first oral dosage form and the second oral dosage form are a tablet, capsule, powder or granule. In one embodiment, one or both of the first oral dosage form and the second oral dosage form are a tablet. In one embodiment, both the first oral dosage form and the second oral dosage form are tablets. In one embodiment, the tablet comprising vildagliptin or a pharmaceutically acceptable salt thereof comprises 50 mg vildagliptin or a pharmaceutically acceptable salt thereof (preferably vildagliptin free base). In one embodiment, the tablet comprising vildagliptin or a pharmaceutically acceptable salt thereof is a Galvus® tablet. In one embodiment, the tablet comprising metformin or a pharmaceutically acceptable salt thereof comprises 500 mg metformin or a pharmaceutically acceptable salt thereof (preferably metformin hydrochloride). In one embodiment, the tablet comprising metformin or a pharmaceutically acceptable salt thereof comprises 850 mg metformin or a pharmaceutically acceptable salt thereof (preferably metformin hydrochloride). In one embodiment, the tablet comprising metformin or a pharmaceutically acceptable salt thereof comprises 1000 mg metformin or a pharmaceutically acceptable salt thereof (preferably metformin hydrochloride).

Dosage Regimen and Pharmaceutical Form

In one embodiment, the metformin monotherapy is administered at a dose of 2000 mg per day. In one embodiment, the metformin monotherapy is administered at a dose of 1700 mg per day. In one embodiment, the metformin monotherapy is administered at a dose of 1500 mg per day. In one embodiment, the metformin monotherapy is administered at a dose of 1000 mg per day.

In one embodiment, the metformin monotherapy is administered at a dose of 1000 mg twice per day. In one embodiment, the metformin monotherapy is administered at a dose of 850 mg twice per day. In one embodiment, the metformin monotherapy is administered at a dose of 750 mg twice per day. In one embodiment, the metformin monotherapy is administered at a dose of 500 mg twice per day.

The metformin or a pharmaceutically acceptable salt thereof and DPP-IV inhibitor (preferably vildagliptin or a pharmaceutically acceptable salt thereof) are administered in therapeutically effective amounts. Therapeutically effective amounts of DPP-IV inhibitors metformin or a pharmaceutically acceptable salt thereof are known to the skilled person. As used herein, "a therapeutically effective amount" refers to an amount of drug that will elicit the desired biological and/or medical response of a tissue, system or animal (including a human) that is being sought by a researcher or clinician.

In one embodiment, the metformin or a pharmaceutically acceptable salt thereof and DPP-IV inhibitor are administered in therapeutically effective amounts for a period which is sufficient to delay loss of glycaemic control in a patient with type 2 diabetes mellitus. In one embodiment, the period is 5 years or more and the loss of glycaemic control is delayed by 5 years or more. In one embodiment, the therapeutically effective amount of metformin or a pharmaceutically acceptable salt thereof is 200 mg per day (administered, e.g., as 1000 mg twice a day), 1700 mg per day (administered, e.g., as 850 mg twice a day), 1500 mg per day (administered, e.g., as 750 mg per day), or 1000 mg per day (administered, e.g. as 500 mg twice a day). In some embodiments where the DPP-IV inhibitor is vildagliptin or a pharmaceutically acceptable salt thereof, the therapeutically effective amount is 100 mg per day (administered, e.g., as 50 mg twice per day). In some embodiments where the DPP-IV inhibitor is sitagliptin or a pharmaceutically acceptable salt thereof, the therapeutically effective amount is 100 mg per day. In some embodiments where the DPP-IV inhibitor is saxagliptin or a pharmaceutically acceptable salt thereof, the therapeutically effective amount is 2.5 mg or 5 mg once daily. In some embodiments where the DPP-IV inhibitor is linagliptin or a pharmaceutically acceptable salt thereof, the therapeutically effective amount is 5 mg once daily. In some embodiments where the DPP-IV inhibitor is alogliptin or a pharmaceutically acceptable salt thereof, the therapeutically effective amount is 25 mg once daily.

In one embodiment, the metformin or a pharmaceutically acceptable salt thereof and DPP-IV inhibitor are administered in therapeutically effective amounts for a period which is sufficient to improve glycaemic control in a patient with type 2 diabetes mellitus. In one embodiment, the period is 5 years or more and the improvement lasts for 5 years or more. In one embodiment, the therapeutically effective amount of metformin or a pharmaceutically acceptable salt thereof is 200 mg per day (administered, e.g., as 1000 mg twice a day), 1700 mg per day (administered, e.g., as 850 mg twice a day), 1500 mg per day (administered, e.g., as 750 mg per day), or 1000 mg per day (administered, e.g. as 500 mg twice a day). In some embodiments where the DPP-IV inhibitor is vildagliptin or a pharmaceutically acceptable salt thereof, the therapeutically effective amount is 100 mg per day (administered, e.g., as 50 mg twice per day). In some embodiments where the DPP-IV inhibitor is sitagliptin or a pharmaceutically acceptable salt thereof, the therapeutically effective amount is 100 mg per day. In some embodiments where the DPP-IV inhibitor is saxagliptin or a pharmaceutically acceptable salt thereof, the therapeutically effective amount is 2.5 mg or 5 mg once daily. In some embodiments where the DPP-IV inhibitor is linagliptin or a pharmaceutically acceptable salt thereof, the therapeutically effective amount is 5 mg once daily. In some embodiments where the DPP-IV inhibitor is alogliptin or a pharmaceutically acceptable salt thereof, the therapeutically effective amount is 25 mg once daily.

In one embodiment, the metformin or a pharmaceutically acceptable salt thereof and DPP-IV inhibitor are administered in therapeutically effective amounts for a period which is sufficient to delay the increase of $HbA_{1c}$ to greater than or equal to 53 mmol/mol (7.0%) in a patient with type 2 diabetes mellitus. In one embodiment, the period is 5 years or more and the increase of $HbA_{1c}$ to greater than or equal to 53 mmol/mol (7.0%) is delayed for 5 years or more. In one embodiment, the therapeutically effective amount of metformin or a pharmaceutically acceptable salt thereof is 200 mg per day (administered, e.g., as 1000 mg twice a day), 1700 mg per day (administered, e.g., as 850 mg twice a day), 1500 mg per day (administered, e.g., as 750 mg per day), or 1000 mg per day (administered, e.g. as 500 mg twice a day). In some embodiments where the DPP-IV inhibitor is vildagliptin or a pharmaceutically acceptable salt thereof, the therapeutically effective amount is 100 mg per day (administered, e.g., as 50 mg twice per day). In some embodiments where the DPP-IV inhibitor is sitagliptin or a pharmaceutically acceptable salt thereof, the therapeutically effective amount is 100 mg per day. In some embodiments where the DPP-IV inhibitor is saxagliptin or a pharmaceutically acceptable salt thereof, the therapeutically effective amount is 2.5 mg or 5 mg once daily. In some embodiments where the DPP-IV inhibitor is linagliptin or a pharmaceutically acceptable salt thereof, the therapeutically effective amount is 5 mg once daily. In some embodiments where the DPP-IV inhibitor is alogliptin or a pharmaceutically acceptable salt thereof, the therapeutically effective amount is 25 mg once daily.

In one embodiment, the metformin or a pharmaceutically acceptable salt thereof and DPP-IV inhibitor are administered in therapeutically effective amounts for a period which is sufficient to increase the time taken to reach an $HbA_{1c}$ measurement of greater than or equal to 53 mmol/mol (7.0%) in a patient with type 2 diabetes mellitus. In one embodiment, the period is 5 years or more and the increase in the time taken is 5 years or more. In one embodiment, the therapeutically effective amount of metformin or a pharmaceutically acceptable salt thereof is 200 mg per day (administered, e.g., as 1000 mg twice a day), 1700 mg per day (administered, e.g., as 850 mg twice a day), 1500 mg per day (administered, e.g., as 750 mg per day), or 1000 mg per day (administered, e.g. as 500 mg twice a day). In some embodiments where the DPP-IV inhibitor is vildagliptin or a pharmaceutically acceptable salt thereof, the therapeutically effective amount is 100 mg per day (administered, e.g., as 50 mg twice per day). In some embodiments where the DPP-IV inhibitor is sitagliptin or a pharmaceutically acceptable salt thereof, the therapeutically effective amount is 100 mg per day. In some embodiments where the DPP-IV inhibitor is saxagliptin or a pharmaceutically acceptable salt thereof, the therapeutically effective amount is 2.5 mg or 5 mg once daily. In some embodiments where the DPP-IV inhibitor is linagliptin or a pharmaceutically acceptable salt thereof, the therapeutically effective amount is 5 mg once daily. In some embodiments where the DPP-IV inhibitor is alogliptin or a pharmaceutically acceptable salt thereof, the therapeutically effective amount is 25 mg once daily.

In one embodiment, the metformin or a pharmaceutically acceptable salt thereof and DPP-IV inhibitor are administered in therapeutically effective amounts for a period which is sufficient to prevent loss of glycaemic control in a patient with type 2 diabetes mellitus. In one embodiment, the period is 5 years or more and the prevention lasts for 5 years or more. In one embodiment, the therapeutically effective amount of metformin or a pharmaceutically acceptable salt thereof is 200 mg per day (administered, e.g., as 1000 mg twice a day), 1700 mg per day (administered, e.g., as 850 mg twice a day), 1500 mg per day (administered, e.g., as 750 mg per day), or 1000 mg per day (administered, e.g. as 500 mg twice a day). In some embodiments where the DPP-IV inhibitor is vildagliptin or a pharmaceutically acceptable salt thereof, the therapeutically effective amount is 100 mg per day (administered, e.g. as 50 mg twice per day). In some embodiments where the DPP-IV inhibitor is sitagliptin or a pharmaceutically acceptable salt thereof, the therapeutically effective amount is 100 mg per day. In some embodiments where the DPP-IV inhibitor is saxagliptin or a pharmaceutically acceptable salt thereof, the therapeutically effective amount is 2.5 mg or 5 mg once daily. In some embodiments where the DPP-IV inhibitor is linagliptin or a pharmaceutically acceptable salt thereof, the therapeutically effective amount is 5 mg once daily. In some embodiments where the DPP-IV inhibitor is alogliptin or a pharmaceutically acceptable salt thereof, the therapeutically effective amount is 25 mg once daily.

In one embodiment, the metformin or a pharmaceutically acceptable salt thereof and DPP-IV inhibitor are administered in therapeutically effective amounts for a period which is sufficient to reduce the risk of a cardiovascular event in a patient undergoing treatment for type 2 diabetes mellitus. In one embodiment, the period is 5 years or more and the risk is reduced for 5 years or more. In one embodiment, the therapeutically effective amount of metformin or a pharmaceutically acceptable salt thereof is 200 mg per day (administered, e.g., as 1000 mg twice a day), 1700 mg per day (administered, e.g., as 850 mg twice a day), 1500 mg per day (administered, e.g., as 750 mg per day), or 1000 mg per day (administered, e.g. as 500 mg twice a day). In some embodiments where the DPP-IV inhibitor is vildagliptin or a pharmaceutically acceptable salt thereof, the therapeutically effective amount is 100 mg per day (administered, e.g., as 50 mg twice per day). In some embodiments where the DPP-IV inhibitor is sitagliptin or a pharmaceutically acceptable salt thereof, the therapeutically effective amount is 100 mg per day. In some embodiments where the DPP-IV inhibitor is saxagliptin or a pharmaceutically acceptable salt thereof, the therapeutically effective amount is 2.5 mg or 5 mg once daily. In some embodiments where the DPP-IV inhibitor is linagliptin or a pharmaceutically acceptable salt thereof, the therapeutically effective amount is 5 mg once daily. In some embodiments where the DPP-IV inhibitor is alogliptin or a pharmaceutically acceptable salt thereof, the therapeutically effective amount is 25 mg once daily.

In one embodiment, the metformin or a pharmaceutically acceptable salt thereof and DPP-IV inhibitor are administered in therapeutically effective amounts for a period which is sufficient to treat type 2 diabetes mellitus without concomitant administration of insulin. In one embodiment, the period is 5 years or more and the period without concomitant administration of insulin is 5 years or more. In one embodiment, the therapeutically effective amount of metformin or a pharmaceutically acceptable salt thereof is 200 mg per day (administered, e.g., as 1000 mg twice a day), 1700 mg per day (administered, e.g., as 850 mg twice a day), 1500 mg per day (administered, e.g., as 750 mg per day), or 1000 mg per day (administered, e.g. as 500 mg twice a day). In some embodiments where the DPP-IV inhibitor is vildagliptin or a pharmaceutically acceptable salt thereof, the therapeutically effective amount is 100 mg per day (administered, e.g., as 50 mg twice per day). In some embodiments where the DPP-IV inhibitor is sitagliptin or a pharmaceutically acceptable salt thereof, the therapeutically effective amount is 100 mg per day. In some embodiments where the DPP-IV inhibitor is saxagliptin or a pharmaceutically acceptable salt thereof, the therapeutically effective amount is 2.5 mg or 5 mg once daily. In some embodiments where the DPP-IV inhibitor is linagliptin or a pharmaceutically acceptable salt thereof, the therapeutically effective amount is 5 mg once daily. In some embodiments where the DPP-IV inhibitor is alogliptin or a pharmaceutically acceptable salt thereof, the therapeutically effective amount is 25 mg once daily.

In one embodiment, metformin or a pharmaceutically acceptable salt thereof (preferably metformin hydrochloride), when administered in combination with vildagliptin or a pharmaceutically acceptable salt thereof (preferably vildagliptin free base), is administered at a dose of 2000 mg per day. In one embodiment, metformin or a pharmaceutically acceptable salt thereof (preferably metformin hydrochloride), when administered in combination with vildagliptin or a pharmaceutically acceptable salt thereof (preferably vildagliptin free base), is administered at a dose of 1700 mg per day. In one embodiment, metformin or a pharmaceutically acceptable salt thereof (preferably metformin hydrochloride), when administered in combination with vildagliptin or a pharmaceutically acceptable salt thereof (preferably vildagliptin free base), is administered at a dose of 1500 mg per day. In one embodiment, metformin or a pharmaceutically acceptable salt thereof (preferably metformin hydrochloride), when administered in combination with vildagliptin or a pharmaceutically acceptable salt thereof (preferably vildagliptin free base), is administered at a dose of 1000 mg per day.

In one embodiment, metformin or a pharmaceutically acceptable salt thereof (preferably metformin hydrochloride), when administered in combination with vildagliptin or a pharmaceutically acceptable salt thereof (preferably vildagliptin free base), is administered at a dose of 1000 mg twice per day. In one embodiment, metformin or a pharmaceutically acceptable salt thereof (preferably metformin hydrochloride), when administered in combination with vildagliptin or a pharmaceutically acceptable salt thereof (preferably vildagliptin free base), is administered at a dose of 850 mg twice per day. In one embodiment, metformin or a pharmaceutically acceptable salt thereof (preferably metformin hydrochloride), when administered in combination with vildagliptin or a pharmaceutically acceptable salt thereof (preferably vildagliptin free base), is administered at a dose of 750 mg twice per day. In one embodiment, metformin or a pharmaceutically acceptable salt thereof (preferably metformin hydrochloride), when administered in combination with vildagliptin or a pharmaceutically acceptable salt thereof (preferably vildagliptin free base), is administered at a dose of 500 mg twice per day.

In one embodiment, vildagliptin or a pharmaceutically acceptable salt thereof (preferably vildagliptin free base) is administered at a dose of 100 mg per day. In one embodiment, vildagliptin or a pharmaceutically acceptable salt thereof (preferably vildagliptin free base) is administered at a dose of 50 mg twice per day.

In one embodiment, the method comprises administration of vildagliptin or a pharmaceutically acceptable salt thereof (preferably vildagliptin free base) at a dose of 100 mg per day and administration of metformin or a pharmaceutically acceptable salt thereof (preferably metformin hydrochloride) at a dose of 2000 mg per day. In one embodiment, the method comprises administration of vildagliptin or a pharmaceutically acceptable salt thereof (preferably vildagliptin free base) at a dose of 100 mg per day and administration of metformin or a pharmaceutically acceptable salt thereof (preferably metformin hydrochloride) at a dose of 1700 mg per day. In one embodiment, the method comprises administration of vildagliptin or a pharmaceutically acceptable salt thereof (preferably vildagliptin free base) at a dose of 100 mg per day and administration of metformin or a pharmaceutically acceptable salt thereof (preferably metformin hydrochloride) at a dose of 1500 mg per day. In one embodiment, the method comprises administration of vildagliptin or a pharmaceutically acceptable salt thereof (preferably vildagliptin free base) at a dose of 100 mg per day and administration of metformin or a pharmaceutically acceptable salt thereof (preferably metformin hydrochloride) at a dose of 1000 mg per day.

In one embodiment, the method comprises administration of vildagliptin or a pharmaceutically acceptable salt thereof (preferably vildagliptin free base) at a dose of 50 mg twice per day and administration of metformin or a pharmaceutically acceptable salt thereof (preferably metformin hydrochloride) at a dose of 2000 mg per day. In one embodiment, the method comprises administration of vildagliptin or a pharmaceutically acceptable salt thereof (preferably vildagliptin free base) at a dose of 50 mg twice per day and administration of metformin (preferably metformin hydrochloride) or a pharmaceutically acceptable salt thereof at a dose of 1700 mg per day. In one embodiment, the method comprises administration of vildagliptin or a pharmaceutically acceptable salt thereof (preferably vildagliptin free base) at a dose of 50 mg twice per day and administration of metformin or a pharmaceutically acceptable salt thereof (preferably metformin hydrochloride) at a dose of 1500 mg per day. In one embodiment, the method comprises administration of vildagliptin or a pharmaceutically acceptable salt thereof (preferably vildagliptin free base) at a dose of 50 mg twice per day and administration of metformin or a pharmaceutically acceptable salt thereof (preferably metformin hydrochloride) at a dose of 1000 mg per day.

In one embodiment, the method comprises administration of vildagliptin or a pharmaceutically acceptable salt thereof (preferably vildagliptin free base) at a dose of 100 mg per day and administration of metformin or a pharmaceutically acceptable salt thereof (preferably metformin hydrochloride) at a dose of 1000 mg twice per day. In one embodiment, the method comprises administration of vildagliptin or a pharmaceutically acceptable salt thereof (preferably vildagliptin free base) at a dose of 100 mg per day and administration of metformin or a pharmaceutically acceptable salt thereof (preferably metformin hydrochloride) at a dose of 850 mg twice per day. In one embodiment, the method comprises administration of vildagliptin or a pharmaceutically acceptable salt thereof (preferably vildagliptin free base) at a dose of 100 mg per day and administration of metformin or a pharmaceutically acceptable salt thereof (preferably metformin hydrochloride) at a dose of 750 mg twice per day. In one embodiment, the method comprises administration of vildagliptin or a pharmaceutically acceptable salt thereof (preferably vildagliptin free base) at a dose of 100 mg per day and administration of metformin (preferably metformin hydrochloride) or a pharmaceutically acceptable salt thereof at a dose of 500 mg twice per day.

In one embodiment, the method comprises administration of vildagliptin or a pharmaceutically acceptable salt thereof (preferably vildagliptin free base) at a dose of 50 mg twice per day and administration of metformin or a pharmaceutically acceptable salt thereof (preferably metformin hydrochloride) at a dose of 1000 mg twice per day. In one embodiment, the method comprises administration of vildagliptin or a pharmaceutically acceptable salt thereof (preferably vildagliptin free base) at a dose of 50 mg twice per day and administration of metformin (preferably metformin hydrochloride) or a pharmaceutically acceptable salt thereof at a dose of 850 mg twice per day. In one embodiment, the method comprises administration of vildagliptin or a pharmaceutically acceptable salt thereof (preferably vildagliptin free base) at a dose of 50 mg twice per day and administration of metformin or a pharmaceutically acceptable salt thereof (preferably metformin hydrochloride) at a dose of 750 mg twice per day. In one embodiment, the method comprises administration of vildagliptin or a pharmaceutically acceptable salt thereof (preferably vildagliptin free base) at a dose of 50 mg twice per day and administration of metformin or a pharmaceutically acceptable salt thereof (preferably metformin hydrochloride) at a dose of 500 mg twice per day.

The metformin or a pharmaceutically acceptable salt thereof and vildagliptin or a pharmaceutically acceptable salt thereof are typically administered orally. In one embodiment, metformin or a pharmaceutically acceptable salt thereof and vildagliptin or a pharmaceutically acceptable salt thereof are administered in a single oral dosage form. In one embodiment, the oral dosage form is a tablet, a capsule, a powder or a granule. In one embodiment, the oral dosage form is a tablet. In one embodiment, the tablet is a fixed-dose combination tablet. In one embodiment, the fixed-dose combination tablet comprises 50 mg of vildagliptin or a pharmaceutically acceptable salt thereof, preferably vildagliptin free base) and 850 mg of metformin or a pharmaceutically acceptable salt thereof (preferably metformin hydrochloride). In one embodiment, the fixed-dose combination tablet comprises 50 mg of vildagliptin or a pharmaceutically acceptable salt thereof (preferably vildagliptin free base) and 1000 mg of metformin or a pharmaceutically acceptable salt thereof (preferably metformin hydrochloride). In one embodiment, the fixed-dose combination tablet comprises 50 mg of vildagliptin or a pharmaceutically acceptable salt thereof (preferably vildagliptin free base) and 500 mg of metformin or a pharmaceutically acceptable salt thereof (preferably metformin hydrochloride). In one embodiment, the fixed-dose combination tablet is a Eucreas® tablet.

In one embodiment, metformin or a pharmaceutically acceptable salt thereof and vildagliptin or a pharmaceutically acceptable salt thereof are administered are separate oral dosage forms. In one embodiment, both oral dosage forms are tablets. In one embodiment, the vildagliptin or a pharmaceutically acceptable salt thereof is contained within a tablet comprising 50 mg of vildagliptin or a pharmaceutically acceptable salt thereof (preferably vildagliptin free base) In one embodiment, the vildagliptin tablet is a Galvus® tablet.

In one embodiment, metformin or a pharmaceutically acceptable salt thereof and vildagliptin or a pharmaceutically acceptable salt thereof are administered simultaneously. In one embodiment, metformin or a pharmaceutically acceptable salt thereof and vildagliptin or a pharmaceutically acceptable salt thereof are administered sequentially. In one embodiment, metformin or a pharmaceutically acceptable salt thereof and vildagliptin or a pharmaceutically acceptable salt thereof are administered separately.

In one embodiment, metformin or a pharmaceutically acceptable salt thereof and vildagliptin or a pharmaceutically acceptable salt thereof are not administered with any further antidiabetic agents. In one embodiment, metformin or a pharmaceutically acceptable salt thereof and vildagliptin or a pharmaceutically acceptable salt thereof are administered with one or more additional antidiabetic agents. In one embodiment, the one or more additional antidiabetic agents are selected from the group consisting of insulin, a sulfonylurea and a thiazolidinedione. The term "sulfonylurea" includes, but is not limited to, glibenclamide, gliclazide, glipizide, glimepiride, tolbutamide, chlorpropamide, glyburide, glipizide, and tolazamide. The term "thiazolidinedione" includes, but is not limited to, rosiglitazone, pioglitazone, ciglitazone, lobeglitazone, darglitazone, englitazone, netoglazone, rivoglitazone, troglitazone, and balaglitazonem. In one embodiment, metformin or a pharmaceutically acceptable salt thereof and vildagliptin or a pharmaceutically acceptable salt thereof are administered with a sulfonylurea. In one embodiment, metformin or a pharmaceutically acceptable salt thereof and vildagliptin or a pharmaceutically acceptable salt thereof are administered with a thiazolidinedione. In one embodiment, metformin or a pharmaceutically acceptable salt thereof and vildagliptin or a pharmaceutically acceptable salt thereof are administered with insulin.

It should be understood that the invention described herein, which relates to a DPP-IV inhibitor (preferably vildagliptin or a pharmaceutically acceptable salt thereof), or metformin or a pharmaceutically acceptable salt thereof, or a combination thereof for use in methods of treatment are equally applicable to:

the use of a DPP-IV inhibitor (preferably vildagliptin or a pharmaceutically acceptable salt thereof), or metformin or a pharmaceutically acceptable salt thereof, or a combination thereof in the manufacture of a medicament for the treatments described herein; and a method of treatment comprising the administration of a DPP-IV inhibitor (preferably vildagliptin or a pharmaceutically acceptable salt thereof), or metformin or a pharmaceutically acceptable salt thereof, or a combination thereof.

It should be understood that the present invention also relates to the aforementioned uses and methods of treatment.

Definitions

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describe pharmaceutically acceptable salts in detail in J. Pharmaceutical Sciences, 1977, 66, 1-19, incorporated herein by reference.

As used herein, the term "glycaemic control" refers to a state in patients with type 2 diabetes mellitus where the patient's $HbA_{1c}$ level is below a certain threshold, which is typically 53 mmol/mol (7%). If a patient's $HbA_{1c}$ level is at or above the threshold for a certain amount of time, for example if two measurements taken 13 weeks apart both show an $HbA_{1c}$ level at or above the threshold, the glycaemic control has been lost.

As used herein, the term "monotherapy" is a therapy which uses a single drug to treat a disease or condition. A type 2 diabetes mellitus patient who is treated with a monotherapy will receive only a single antidiabetic drug. The term "metformin monotherapy" refers to a monotherapy which comprises the administration of metformin or a pharmaceutically acceptable salt thereof, to the patient as a sole antidiabetic drug. Typically, the metformin is administered as metformin hydrochloride in metformin monotherapy.

As used herein, the term "subsequent" in the context of "metformin monotherapy followed by subsequent co-administration of a DPP-IV inhibitor (preferably vildagliptin or a pharmaceutically acceptable salt thereof) and metformin or a pharmaceutically acceptable salt thereof" is differentiated from the initial administration of a combination of DPP-IV inhibitor (preferably vildagliptin or a pharmaceutically acceptable salt thereof) and metformin or a pharmaceutically acceptable salt thereof according to the invention. In particular, "subsequent" in this context means that metformin monotherapy has already been administered for a relatively long period of time, e.g. several days, months or years, prior to commencement of the second-line therapy, but has been discontinued prior to commencement of the second-line therapy due, for example, to loss of glycaemic control.

As used herein, the term "patient" includes, but is not limited to mammals. Preferably, the patient is a human patient.

As used herein, the term "treating" and its variants (e.g. "treat", "treatment" etc.) is understood as the management and care of a patient for the purpose of combatting the disease, condition or disorder.

As used herein, the term "prevent" and its variants (e.g. "preventing") refers to the ability of a drug, or a combination of drugs, to stave off the occurrence of a clinically undesirable disease, disorder, symptom, or condition for a clinically significant period of time. For example, the combination of drugs herein may prevent loss of glycaemic control by staving off the loss of glycaemic control for a period of 5 years or more.

As used herein, "$HbA_{1c}$" refers to glycated haemoglobin, i.e. to haemoglobin which is covalently linked to a sugar (e.g. glucose) molecule. Elevated levels of $HbA_{1c}$ in the bloodstream are indicative of diabetes mellitus. Methods of detecting and measuring levels of $HbA_{1c}$ are known to the skilled person. Typically, these methods involve taking a blood sample from a patient and determining the $HbA_{1c}$ level in the sample. This may be done using, for example the Quo-Test® $HbA_{1c}$ Analyzer (available from EKF Diagnostics), the Quo-Lab® $HbA_{1c}$ Analyzer (also available from EKF Diagnostics), or the Afinion™ $HbA_{1c}$ (available from Abbott).

As used herein, the term "adverse event" refers to any unfavourable and unintended sign, symptom, or disease associated with the use of the medicinal product, whether or not considered related to the medicinal product.

As used herein, the term "cardiovascular event" is an event which may cause damage to the heart and/or circulatory system. The term "cardiovascular event" encompasses, but is not limited to a "macrovascular event". Macrovascular events include, but are not limited to, cardiovascular death, non-fatal myocardial infarction or stroke, and hospital admission for heart failure.

As used herein, "hypoglycaemia" is when blood glucose levels fall below the normal range. For example, a patient having hypoglycaemia may have a blood glucose level of less than 4 mmol/L (72 mg/dL).

As used herein, the term "dose" refers to the amount of a drug substance which is administered to a patient. A dose may be given to the patient in a single administration, or a dose may be given in multiple separate administrations.

As used herein, the term "co-administration" and its variants (e.g. "co-administer", "co-administered" etc.) is a reference to the administration of more than one drug to treat a disease or condition in a patient. The term "co-administration" includes, but is not limited to, administration of two or more drugs simultaneously in a single dosage form (e.g. a fixed-dose combination tablet), administration of two or more drugs simultaneously in separate dosage forms, and administration of two or more drugs sequentially in separate dosage forms. When two or more drugs are co-administered sequentially, they are administered separately with a time interval between each administration. This time interval is less than one day, for example less than 12 hours, less than one hour or typically less than several minutes (in particular less than one minute).

The invention will now be described with reference to the following example. For the avoidance of doubt, this example does not limit the scope of the invention, which is defined in the appended claims.

Example 1—the VERIFY Study Protocol and Results

"Vildagliptin Efficacy in combination with metfoRmIn For earlY treatment of type 2 diabetes" (VERIFY) was a randomised, double-blind, parallel-group study of newly diagnosed patients with type 2 diabetes conducted in 254 centres across 34 countries. The study consisted of a 2-week screening visit, a 3-week metformin-alone run-in period, and a 5-year treatment period, which was further split into study periods 1, 2, and 3. During the 5-year treatment period, treatment was initially intensified when loss of glycaemia occurred and thereafter when clinically indicated, at the discretion of study investigators (see FIG. 1).

In the trials, metformin was administered as metformin hydrochloride and vildagliptin was administered as vildagliptin free-base.

The study is registered with clinicaltrials.gov, NCT01528254.

Key Inclusion and Exclusion Criteria

The trial enrolled individuals aged 18-70 years with type 2 diabetes, diagnosed within 2 years as per local diagnostic criteria, with centrally confirmed $HbA_{1c}$ of 48-58 mmol/mol (6.5-7.5%) and body-mass index (BMI) of 22-40 kg/m². Only patients who received appropriate lifestyle modification advice before enrolment, including diet counselling and exercise training were included in the study. Individuals were excluded if they were receiving glucose-lowering treatment (except metformin≤2000 mg daily within 1 month prior to first screening visit) within 3 months prior to screening, or for more than 3 consecutive months or a combined total of more than 3 months in the past 2 years. Individuals were also excluded if they were using any weight-loss medications within 3 months prior to screening, had chronic liver disease or ongoing congestive heart failure (New York Heart Association Functional Classification III-IV), or were pregnant or nursing.

Randomisation and Masking

Patients were randomly assigned in a 1:1 ratio either to the early combination treatment group or to the initial metformin monotherapy group, with the help of an interactive response technology system (Cenduit Interactive Response Technology, version 1.48.1; Nottingham, UK) and simple randomisation without stratification. Patients, investigators, clinical staff performing the assessments, and data analysts were masked to treatment allocation. For the study period 1, patients in the monotherapy group received a placebo in addition to the existing stable dose of metformin. Patients in study periods 2 and 3 were masked for the use of combination therapy. The use of insulin in study period 3 was open label (FIG. 1).

Procedures

After the 2-week screening visit, all eligible participants entered a run-in period of metformin up-titration (targeting 1500 mg per day or maximum tolerated dose). At the end of the run-in period, participants who were able to tolerate at least 1000 mg per day of metformin entered study period 1 and were randomly assigned to receive either the early combination treatment with metformin (stable daily dose of 1000 mg, 1500 mg, or 2000 mg) and vildagliptin 50 mg twice daily, or standard-of-care initial metformin monotherapy (stable daily dose of 1000 mg, 1500 mg, or 2000 mg) and placebo twice daily (FIG. 1) All doses of metformin (500 mg tablet form) and vildagliptin (50 mg tablet form) were administered orally twice daily, as single tablets. Dose adjustment of metformin in both treatment groups was permitted during the first 4 weeks in the trial, to allow adjustment to a dose of 2000 mg per day or the maximum tolerable dose of at least 1000 mg per day post-randomisation. No adjustment was allowed afterwards. $HbA_{1c}$ was measured every 3 months. If the initial treatment did not maintain $HbA_{1c}$ below 53 mmol/mol (7.0%) confirmed at two consecutive scheduled visits which were 13 weeks apart, patients in the metformin monotherapy group received vildagliptin 50 mg twice daily in place of the placebo and entered study period 2, during which all patients received the combination therapy. Patients in both groups received vildagliptin in a medication pack designed differently from the vildagliptin or placebo packs used in period 1. At study period 3, rescue therapy with insulin was added to the metformin and vildagliptin combination therapy, to maintain glycaemic control in patients as per local diabetes treatment guidelines and as per investigator discretion. Patients discontinued study treatment if an alternative glucose-lowering medication was considered by the treating physician. Study procedures were completed every 13 weeks when participants visited the study site. Safety assessments were completed at every study visit and included collection of all adverse events and serious adverse events.

Outcomes

The primary efficacy endpoint was the time from randomisation to initial treatment failure, defined as $HbA_{1c}$ measurement of at least 53 mmol/mol (7.0%) at two consecutive scheduled visits, 13 weeks apart from randomisation through period 1 (the earliest possible failure time is 6 months). The secondary endpoints can be summarised as: progression of $HbA_{1c}$ after the start of period 2 to the end of period 2 assessed by rate of loss in glycaemic control over time, both by threshold (second treatment failure) and slope of glycaemia; progression of fasting plasma glucose over time assessed by estimated annualized slope; change in $HbA_{1c}$ based on baseline characteristics; and safety and tolerability. The specific secondary endpoints were rate of loss of glycaemic control during period 1; rate of loss of $HbA_{1c}$ over time during period 2; rate of loss in glycaemic control in fasting plasma glucose (FPG) during period 1; rate of loss in glycaemic control in FPG during period 2; rate of loss of beta cell function from baseline to end of study; rate of change of insulin sensitivity from baseline to end of study; adverse events, serious adverse events and death. Exploratory endpoints included analysis of cardiovascular outcomes as assessed by time to first adjudicated macrovascular event, including cardiovascular death, non-fatal myocardial infarction or stroke, or hospital admission for heart failure.

Statistical Analysis

The statistical analysis plan with one primary efficacy endpoint was finalised prior to unlocking treatment codes for analysis. A specific order of analysis was redefined for the analysis approach in the updated statistical analysis plan in order to avoid methodological duplication and potential dilution of alpha spending. The planned sample size of 1000 patients per treatment approach was expected to provide an approximate 75% power to detect a risk reduction of 25% in time to initial treatment failure with the combination treatment approach, compared with monotherapy. The full analysis set included patients who received at least one randomised study medication and had at least one post-randomisation efficacy parameter assessed. The safety analysis set included all patients who received at least one dose of randomised study medication. Comparability of the two treatment approaches was assessed by demographic and baseline characteristics.

The primary efficacy endpoint of time to initial treatment failure was measured in the full analysis set with a Cox proportional hazards regression model that included treatment approach and geographical region as factors and baseline $HbA_{1c}$ as a covariate. The time to second treatment failure during period 2 was measured in the full analysis set using the same Cox regression model. Kaplan-Meier estimates for cumulative probability of initial and second treatment failure over time were assessed. In simple terms, in each treatment strategy arm, the first treatment failure is defined as two consecutive values of $HbA_{1c}$ of at least 53 mmol/mol (7.0%) and the second treatment failure as two further consecutive values of $HbA_{1c}$ of at least 53 mmol/mol (7.0%). All patients contributed to the Kaplan-Meier comparator in each group. The monotherapy comparator group comprised patients with one treatment failure (in period 1) who were receiving the vildagliptin combination in period 2, as well as those on metformin monotherapy without treatment failure in period 1. Subgroup analyses for time to initial treatment failure were done using similar Cox regression analyses and treatment-by-subgroup interaction was assessed. Mean $HbA_{1c}$ values and change from baseline by treatment approach and visit were evaluated. The proportion of patients with $HbA_{1c}$ below 53 mmol/mol (7.0%), 48 mmol/mol (6.5%), and 42 mmol/mol (6.0%) were assessed over time during the study. Loss of glycaemic control, assessed by the annualized slope of $HbA_{1c}$ over time from week 26 to the end of period 1, was measured with a linear mixed effect model that included treatment approach and region as factors, baseline $HbA_{1c}$ and time of $HbA_{1c}$ measurement (in years) as covariates, and interaction of treatment approach by time. An unstructured covariance method was used. CIs and p values for secondary endpoints and subgroup effects have not been adjusted for multiplicity. Briefly, for the primary efficacy variable, patients who prematurely discontinued during period 1 were included as no event at the time of discontinuation (i.e., censored for time values at the time of discontinuation). Equally, patients remaining under glycaemic threshold or with no confirmed value above it at the next scheduled visit, were included as no event and only censored for time during the last study visit. When assessing the primary endpoint, available $HbA_{1c}$ values were used without imputation for missing values. For the analysis of second treatment failure, patients remaining in period 1 contributed to the percentage of patients without treatment failure, and for those with treatment failure in period 1 but not in period 2, time from randomisation to the end of period 2 was calculated as no event (censored for time). Significance in the analyses was established on the basis of a two-sided 0.05 significance level (equivalent to a one-sided 0.025 significance level). Adverse events were summarised as number and percentage of patients having any adverse event by treatment group and in each primary system organ class. Hypoglycaemic events, microvascular and macrovascular complications were assessed separately. Time to first adjudicated macrovascular events were assessed using the Cox regression model and all suspected macrovascular events were subject to adjudication. The incidence of neoplasms were compared using the $X^2$ test. The statistics program used for analyses was SAS (version 9.4; Cary, NC, USA).

Results

Figure 2:
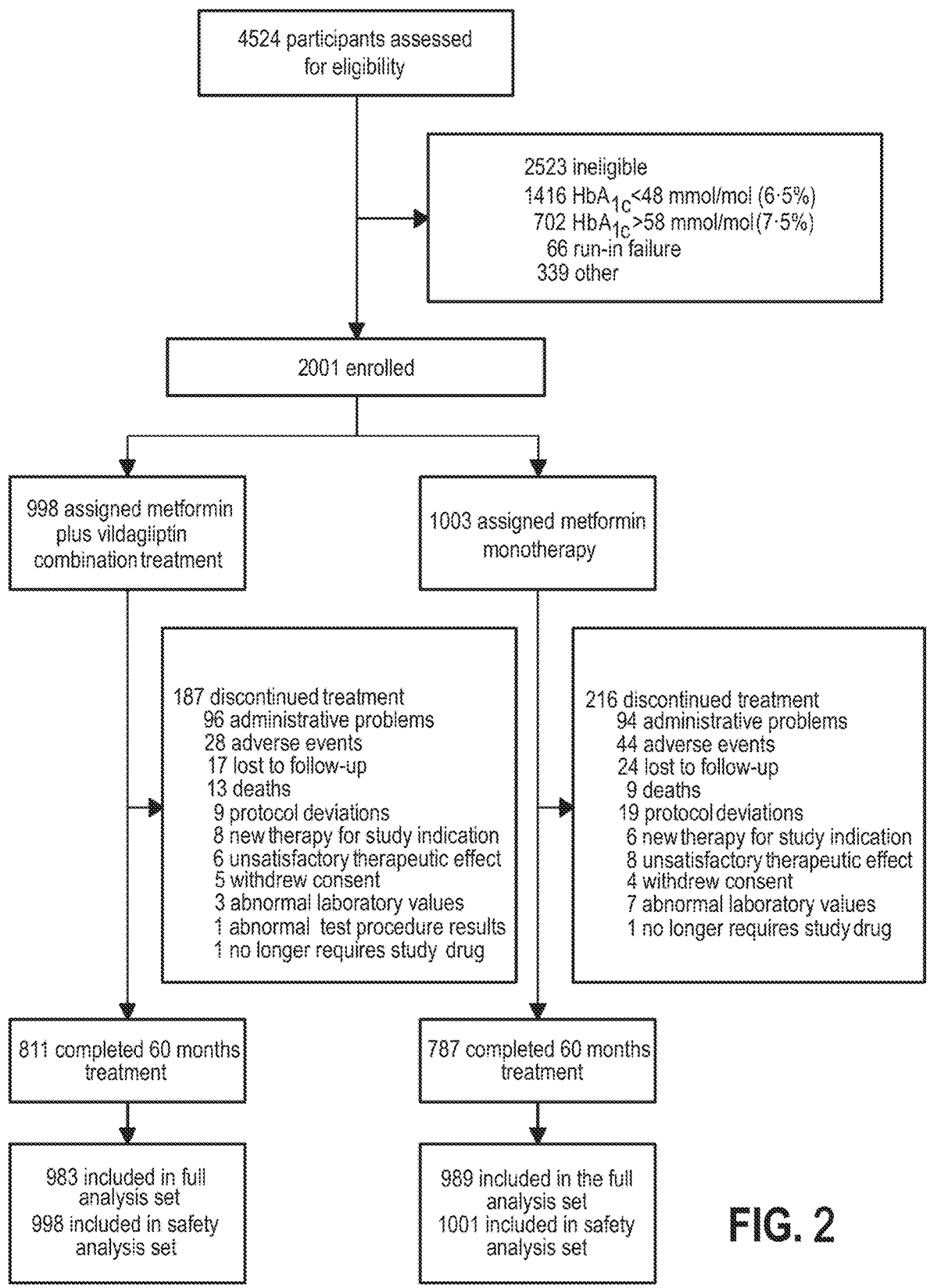
FIG. 2 shows the trial profile for the VERIFY study.

Of the 4524 participants screened, 2001 eligible participants were randomly assigned to either the early combination treatment group (n=998) or the initial metformin monotherapy group (n=1003; FIG. 2). Of the 2001 eligible patients, 1710 were aged between 18 and 64, and 291 patients were aged 65 and over. The most common reasons for study exclusion were $HbA_{1c}$ outside the protocol-defined range and metformin intolerance prior to up-titration. A total of 1598 (79.9%) patients completed the 5-year study; 811 (81.3%) in the early combination therapy group and 787 (78.5%) in the monotherapy group (FIG. 2). The median follow-up time was 59.8 months (IQR 59.4-60.0) for patients in the early combination treatment group and 59.8 months (IQR 59·3-60·0) for patients in the monotherapy group. 17 patients in the combination treatment group and 24 in the monotherapy groups were lost to follow-up. This is summarised in Table 1 below:

TABLE 1

Participant Flow Table, Overall study

| Arm/Group Description | Vilda 50 mg bid + metformin vildagliptin (Vilda 50 mg bid) + metformin | Placebo + metformin Placebo of vildagliptin (Vilda 50 mg bid) + metformin | Total |
|---|---|---|---|
| Started | 998 | 1003 | 2001 |
| Safety Set | 998 | 1001 | 1999 |
| Full Analysis Set (FAS) | 983 | 989 | 1972 |
| Completed Treatment Period 1 | 458 | 273 | 731 |
| Completed Treatment Period 2 | 244 | 399 | 643 |
| Completed Treatment Period 3 | 109 | 115 | 224 |
| Completed | 811 | 787 | 1598 |
| Not Completed | 187 | 216 | 403 |
| Administrave problems | 96 | 94 | 190 |
| Adverse Event | 28 | 44 | 72 |
| Lost to Follow-up | 17 | 24 | 41 |
| Death | 13 | 9 | 22 |
| Protocol deviation | 9 | 19 | 28 |
| New therapy for study indication | 8 | 6 | 14 |
| Unsatisfactory therapeutic effect | 8 | 8 | 14 |
| withdrawal by Subject | 5 | 4 | 9 |
| Abnormal laboratory value(s) | 3 | 7 | 10 |
| Abnormal test procedure result(s) | 1 | 0 | 1 |
| No longer requires study drug | 1 | 1 | 2 |

Baseline demographic and clinical characteristics were similar between treatment groups. Mean age of the patients at randomisation was 54.1 (SD 9.5) years in the combination treatment group and 54.6 (9.2) years in the monotherapy group, and mean BMI was 31.2 (SD 4.8) kg/m² in the combination treatment group and 31.0 (4.7) kg/m² in the monotherapy group. Mean $HbA_{1c}$ at randomisation was 50.0 (SD 4.4) mmol/mol in the combination treatment group and 50.0 (5.5) mmol/mol in the monotherapy group (table 1). 937 (93.9%) of 998 patients in the combination treatment group and 937 (93.4%) of 1003 patients in the monotherapy group had concomitant medications equally administered during the study for management of prevalent concomitant conditions. A similar proportion of patients in both treatment groups (405 [40.6%] in the combination treatment group and 412 [41.1%] in the monotherapy group) received metformin less than 4 weeks prior to study entry. A few female patients (one in the combination treatment group and three in the monotherapy group) received short-term insulin because of gestational diabetes prior to having been diagnosed with type 2 diabetes. This is summarised in Table 2 below.

TABLE 2

| Baseline Characteristics | | | |
|---|---|---|---|
| | Vilda 50 mg bid + metformin | Placebo + metformin | |
| | Arm/Group Description | | |
| | Placebo of vildagliptin (Vilda 50 mg bid) + Metformin | vildagliptin (Vilda 50 mg bid) + Metformin | Total |
| Number of Participants [units: participants] Age Continuous (units: Years) | 998 | 1003 | 2001 |
| Mean ± Standard Deviation Sex: Female, Male (units: Participants) Court of Participants (Not Applicable) | 54.1 ± 9.54 | 54.6 ± 9.24 | 54.3 ± 9.39 |
| Female | 545 | 515 | 1060 |
| Male | 453 | 488 | 941 |
| Race/Ethnicity, Customized (units: Participants) | | | |
| Caucasian | 605 | 612 | 1217 |
| Black | 26 | 23 | 49 |
| Asian | 186 | 187 | 373 |
| Native American | 103 | 107 | 210 |
| Other | 78 | 74 | 152 |
| Glycosylated hemoglobin (HbA1c)[1] (units: Percent) | | | |
| Mean ± Standard Deviation fasting plasma glucose (FPG)[2] (units: mmol/l) | 6.7 ± 0.45 | 6.7 ± 0.47 | 6.7 ± 0.46 |
| Mean ± Standard Deviation Duration of type 2 diabetes[3] (units: mmol/l) | 7.1 ± 1.40 | 7.2 ± 1.47 | 7.1 ± 1.44 |
| Mean ± Standard Deviation Glomerular Filtration Rate (Modification of Diet in Renal Disease)[4] (units: Participants) Count of Participants (Not Applicable) | 6.2 ± 7.00 | 6.6 ± 8.05 | 6.4 ± 7.55 |
| Normal (>80) | 660 | 661 | 1321 |
| Mild (>=50-<= 80) | 333 | 337 | 670 |
| Moderate (>=30-<50) | 3 | 4 | 7 |
| Severe (<30) | 0 | 1 | 1 |
| Missing | 2 | 0 | 2 |
| Is subject a current smoker?[5] (units: Participants) Count of Participants (Not Applicable) | | | |
| Is subject a current smoker? = Yes | 154 | 136 | 290 |
| Is subject a current smoker? = No | 844 | 867 | 1711 |

[1]Baseline $HbA_{1c}$ is the sample obtained on day 1, or the sample obtained at an earlier visit (scheduled or unscheduled) which was closest to Day 1, if the Day 1 measurement is missing.
[2]Based FPG is the sample obtained on day 1, or the sample obtained at an earlier visit (scheduled or unscheduled) which was closest to Day 1, if the Day 1 measurement is missing.
[3]Duration of type 2 diabetes is collected on the day of the screening measurement (Week-5, Visit 1).
[4]GFR (MDRD) = GFR estimated using the MDRD formula. Baseline GFR is calculated using the serum creatinine and body weight value at the Day 1 measurement, or the value obtained at an earlier visit (scheduled or unscheduled) which was closest to Day 1, if the Day 1 measurement is missing. Age is the value at screening.
[5]Smoking status is collected on the day of the screening measurement (Week-5, Visit 1).

Figure 3A:
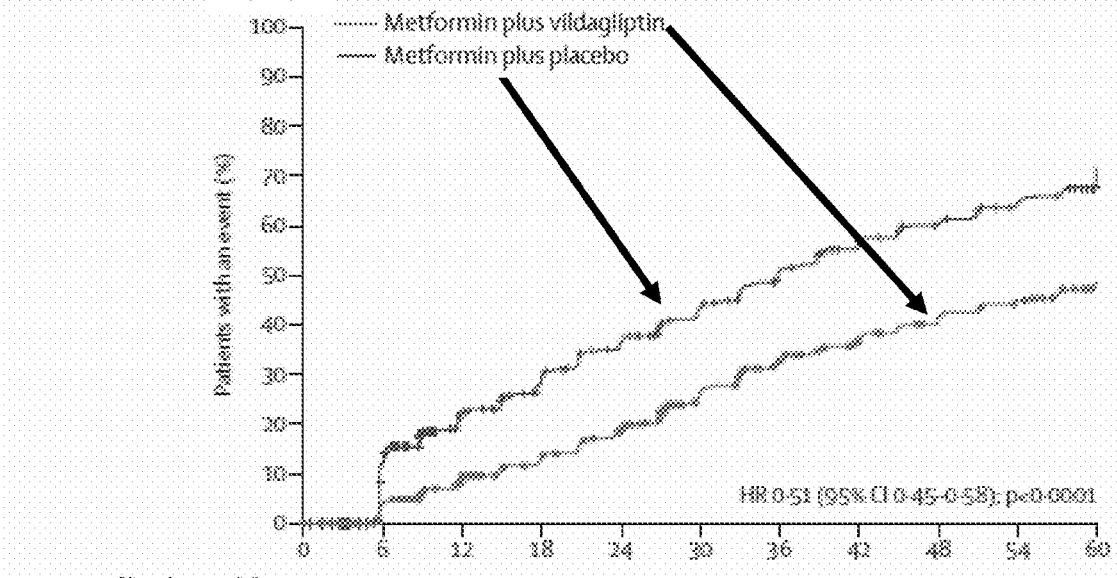
FIG. 3A shows the cumulative probability of initial treatment failure.
Figure 3B:
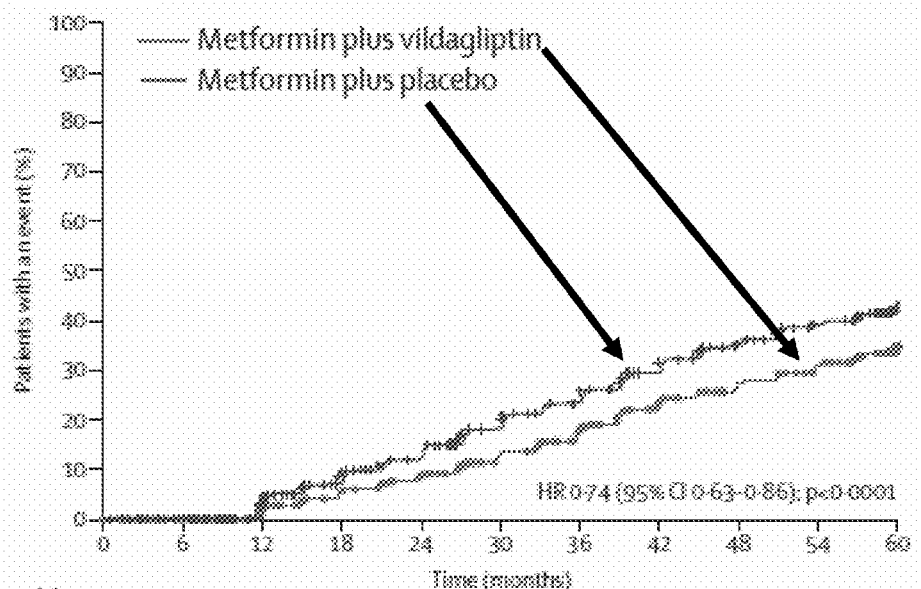
FIG. 3B shows the cumulative probability of second treatment failure. Hazard ratios are based on Cox regression analysis.
Figure 4:
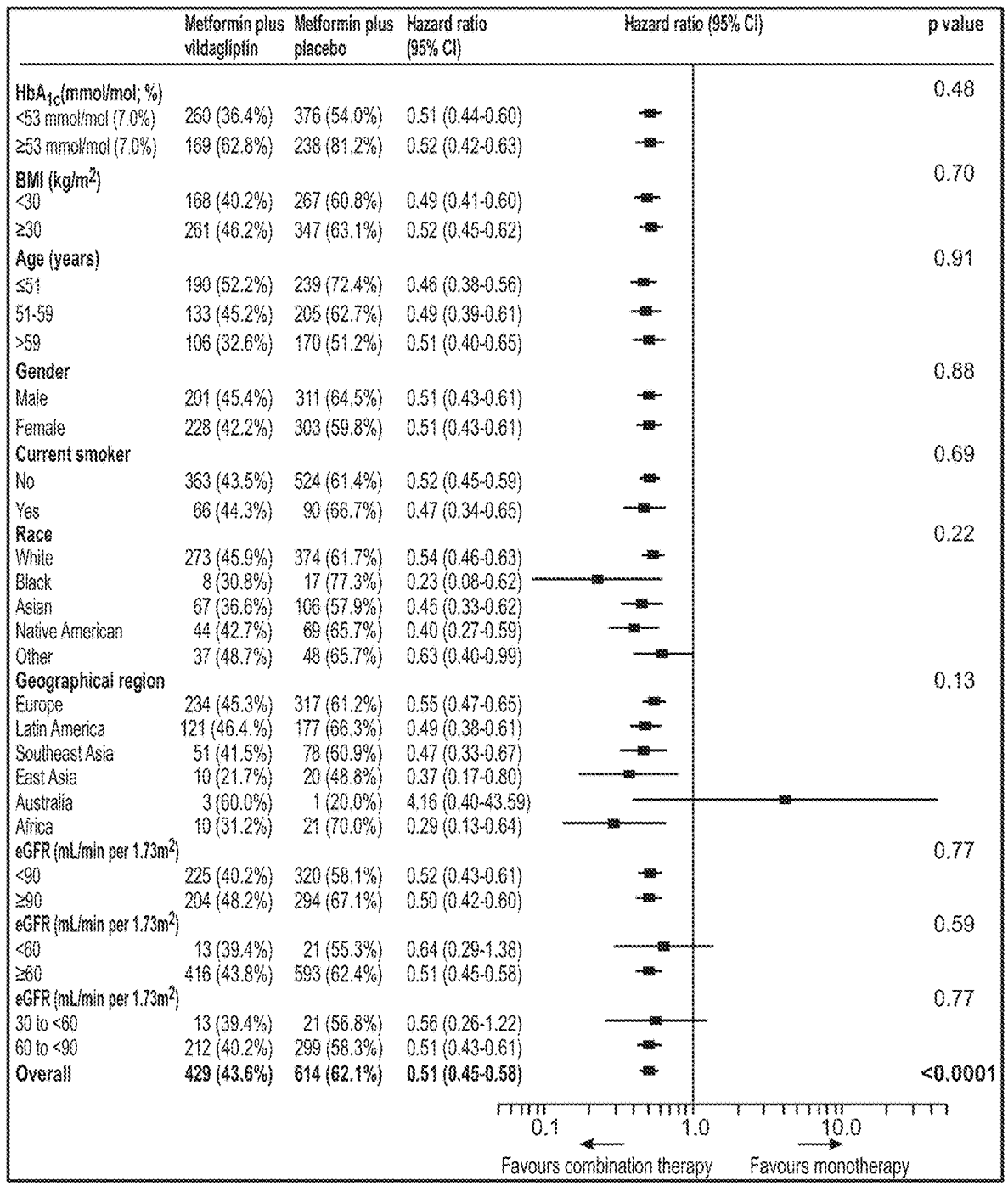
FIG. 4 shows the subgroup analysis of time to initial treatment failure. Hazard ratios and the associated CIs and p values were obtained from a Cox proportional hazards model containing terms for treatment approach, geographical region, and baseline $HbA_{1c}$. Significance was established on the basis of a two-sided 0.05 significance level. The treatment-by-subgroup interaction p values are provided for tests of homogeneity of between-group differences among subgroups, with no adjustment for multiple testing. The p value for treatment comparison in the overall population is also provided. $HbA_{1c}$=glycated haemoglobin A1c. eGFR=estimated glomerular filtration rate.

The incidence of initial treatment failure during period 1 was 429 (43.6%) patients in the combination treatment group and 614 (62.1%) patients in the monotherapy group. The median observed time to treatment failure in the monotherapy group was 36.1 (IQR 15.3—not reached [NR]) months, while the median time to treatment failure time for those receiving early combination therapy could only be estimated to be beyond the study duration at 61.9 (29.9—NR) months. A significant reduction in the relative risk (RR) for time to initial treatment failure was observed in the early combination treatment group compared with the monotherapy group over the 5-year study duration (hazard ratio [HR] 0.51 [95% CI 0.45-0.58]; p<0.0001; FIG. 3A). The RR for time to second treatment failure during period 2 was also significantly reduced in the combination treatment group compared with monotherapy group (HR [95% CI]: 0.74 [0.63, 0.86], p<0.0001) (FIG. 3B). There was also a consistently lower $HbA_{1c}$ observed over time with the combination treatment group compared with the monotherapy throughout the study duration, with a greater proportion of patients in the early combination treatment group with $HbA_{1c}$ below 53 mmol/mol (7.0%), 48 mmol/mol (6.5%), and 42 mmol/mol (6.0%). Subgroup analyses for time to initial treatment failure revealed a consistently significant benefit of early combination treatment over monotherapy for the primary outcome (FIG. 4). This benefit was shown for predefined subgroups of $HbA_{1c}$, BMI, age, gender, smoking status, race, geographical regions, and estimated glomerular filtration rate (eGFR) categories, with no evidence of heterogeneity. Results and statistical analysis associated with the primary efficacy endpoint (time to initial treatment failure) are given below in Tables 3 and 4.

TABLE 3 primary efficacy endpoint data
(Time Frame: Visit 4 (Week 13) up to End of Study (Study Drug Discontinuation or Premature Subject Discontinuation))

| Arm/Group Description | Vilda 50 mg bid + metformin vildagliptin (Vilda 50 mg bid) + metformin | Placebo + metformin Placebo of vildagliptin (Vilda 50 mg bid) + metformin |
|---|---|---|
| Number of Participants Analyzed [units: participants] | 983 | 989 |
| Time to initial treatment failure (unit Rate (%)) Number (95% Confidence Interval) | | |
| Weeks 13-52 | 7.81 (6.28 to 9.70) | 19.97 (17.58 to 22.65) |
| Year 2 | 17.79 (15.49 to 20.38) | 34.67 (31.72 to 37.62) |
| Year 3 | 31.24 (28.35 to 34.33) | 48.21 (45.12 to 51.61) |
| Year 4 | 39.64 (36.74 to 43.11) | 59.29 (56.08 to 62.53) |
| Year 5 | 45.41 (43.20 to 49.74) | 66.57 (63.43 to 69.69) |
| >Year 5 | 52.67 (44.29 to 61.58) | 74.39 (68.39 to 80.04) |

TABLE 4 statistical analysis of primary efficacy endpoint data

| Group | Vilda 50 mg bid + metformin, Placebo + melgormin |
|---|---|
| P Value | <0.001 |
| Method | Regression, Cox |
| Hazard Ratio (HR) | 0.51 |
| 95% Confidence interval 2-sided | 0.45 to 0.58 |

Glycaemic control also deteriorated more rapidly in the monotherapy group than in the early combination treatment group. The difference in adjusted mean rate of change in $HbA_{1c}$ per year (coefficient of failure) was −0.02 (SD 0.01; 95% CI −0.05 to 0.00; two-sided p=0.085) at the end of period 1. Over the 5-year study, mild reduction in body weight from baseline was reported in patients treated with early combination therapy as well as metformin monotherapy. Results and statistical analysis associated with the secondary endpoints are given below in Tables 5-17.

TABLE 5 rate of loss in glycaemic control during Period 1 efficacy endpoint data

| Arm/Group Description | Vilda 50 mg bid + metformin vildaglipin (Vilda 50 mg bid) + metformin | Placebo + metforinin Placebo of vildaglipin (Vilda 50 mg bid) + metformin |
|---|---|---|
| Number of Participants Analyzed ]units: | 983 | 989 |
| Rate of loss in glycemic control during Period 1 (Units: Rate (%)) Mean, ± Standard Error | 0.24 ± 0.01 | 0.27 ± 0.01 |

TABLE 6 statistical analysis of rate of loss in glycaemic control during Period 1 efficacy endpoint data

| Groups | Vilda 50 mg bid + melformin, Placebo + metformin |
|---|---|
| P Value | 0.042 |
| Method | Mixed Models Analysis |

TABLE 6-continued statistical analysis of rate of loss in glycaemic control during Period 1 efficacy endpoint data

| Groups | Vilda 50 mg bid + melformin, Placebo + metformin |
|---|---|
| Slope | −0.02 |
| Standard Error of the mean | 0.01 |
| 95% Confidence interval 2-Sided | −0.05 to 0.00 |

TABLE 7 rate of loss in glycaemic control in $HbA_{1c}$ over time during Period 2 efficacy data

| Arm/Group Description | Vilda 50 mg bid + metformin Placebo of vildagliptin (Vilda 50 mg bid) + Metformin | Placebo + metformin Placebo of vildagliptin (Vilda 50 mg bid) + Metformin |
|---|---|---|
| Number of Participants Analyzed [units: participants] | 410 | 588 |
| Rate of loss in glycemic control in HbA1c over time during Period 2 (units: Rate (%)) Mean ± Standard Error | 1.11 ± 0.15 | 1.02 ± 0.12 |

TABLE 8 statistical analysis of rate of loss in glycaemic control in $HbA_{1c}$ over time during Period 2 efficacy data

| Groups | Vilda 50 mg bid + metformin, Placebo + rnetformin |
|---|---|
| P Value | 0.635 |
| Method | Mixed Models Analysis |
| Slope | 0.09 |
| Standard Error of the mean | 0.19 |
| 95% Confidence Interval 2-Sided | −0.29 to 0.47 |

TABLE 9 rate of loss in glycaemic control in fasting plasma glucose (FPG) during Period 1 efficacy data

| Arm/Group Description | Vilda 50 mg bid + metformin Placebo of vildaglipin (Vilda 50 mg bid) + metformin | Placebo + metformin Placebo of vildaglipin Vilda 50 mg bid) + metformin |
|---|---|---|
| Number of Participants Analyzed [units: participants] | 983 | 989 |
| Rate of loss in glycemic control in Fasting Plasma Glucose (FPG) during Period 1 Units: Rate (%)) Mean ± Standard Error | 0.25 ± 0.01 | 0.26 ± 0.01 |

TABLE 10 statistical analysis of rate of loss in glycaemic control in fasting plasma glucose (FPG) during Period 1 efficacy data

| Groups | Vilda 50 mg bid + metformin, Placebo + metformin |
|---|---|
| P Value | 0.530 |
| Method | Mixed Modets Analysis |
| Slope | −0.01 |
| Standard Error of the mean | 0.02 |
| 95% Confidence Interval 2-Sided | −0.05 to 0.02 |

TABLE 11 rate of loss in glycaemic control in fasting plasma glucose (FPG) during Period 2 efficacy data

| Arm/Group Description | Vilda 50 mg bid + metformin Placebo of vildagliptin (Vilda 50 mg bid) + Metformin | Placebo + metformin Placebo of vildagliptin (Vilda 50 mg bid) + Metformin |
|---|---|---|
| Number of Participants Analyzed [units: participants] | 410 | 588 |
| Rate of loss in glycemic control in Fasting Plasma Glucose (FPG) over time during Period 2 (units: Rate (%)) Mean ± Standard Error | 1.27 ± 0.25 | 0.99 ± 0.19 |

TABLE 12 statistical analysis of rate of loss in glycaemic control in fasting plasma glucose (FPG) during Period 2 efficacy data

| Groups | Vilda 50 mg bid + metformin, Placebo + metformin |
|---|---|
| P Value | 0.381 |
| Method | Models Analysis Method |
| Slope | 0.28 |
| Standard Error of the mean | 0.32 |
| 95% Confidence Interval 2-Sided | −0.35 to 0.90 |

TABLE 13 rate of loss of beta cell function from baseline to end of study efficacy data

| Arm/Group Description | Vilda 50 mg bid + metformin vildaglipin (Vilda 50 mg bid) + metformin | Placebo + metformin Placebo of vilda 50 mg bid) + metformin |
|---|---|---|
| Number of Participants Analyzed [units: participants] | 228 | 227 |
| Rate of loss of beta cell function from baseline to end of study (units: Rate (%)) Mean ± Standard Error | | |
| From Week 13 to end of Period 1 | −0.60 ± 0.15 | −0.53 ± 0.18 |
| From Week 13 to end of Period 2 | −0.93 ± 0.14 | −0.43 ± 0.15 |
| From Week 13 to end of study | −1.04 ± 0.15 | −0.46 ± 0.05 |

TABLE 14 statistical analysis of rate of loss of beta cell function form baseline to end of study efficacy data

| Groups | Vilda 50 mg bid + metformin, Placebo + metformin | From Week 13 to end of Period 1 |
|---|---|---|
| P Value | 0.744 | |
| Method | Mixed Models Analysis | |
| Slope | −0.08 | |
| Standard Error of the mean | 0.23 | |
| 95% Confidence Interval 2-Sided | −0.53 to 0.38 | |

| Groups | Vilda 50 mg bid + metformin, Placebo + metformin | From Week 13 to end of Period 2 |
|---|---|---|
| P Value | 0.017 | |
| Method | Mixed Models Analysis | |
| Slope | −0.50 | |
| Standard Error of the mean | 0.21 | |
| 95% Confidence Interval 2-Sided | −0.91 to −0.09 | |

| Groups | Vilda 50 mg bid + metformin, Placebo + metformin | From Week 13 to end of study |
|---|---|---|
| P Value | 0.006 | |
| Method | Mixed Models Analysis | |
| Slope | −0.58 | |
| Standard Error of the mean | 0.21 | |
| 95% Confidence Interval 2-Sided | −0.99 to −0.17 | |

TABLE 15 rate of change of insulin sensitivity from baseline to end of study efficacy data

| | Arm/Group Description | |
|---|---|---|
| | Vilda 50 mg bid + metformin vildagliptin (Vilda 50 mg bid) + Metformin | Placebo + metformin Placebo of vildagliptin (Vilda 50 mg bid) + Metformin |
| Number of Participants Analyzed [units: participants] | 228 | 227 |
| Rate of change in insulin sensitivity from baseline to end of study (units: Rate (%)) Mean ± Standard Error | | |
| From Week 13 to end of Period 1 | −4.61 ± 1.38 | 0.41 ± 1.66 |
| From Week 13 to end of Period 2 | −6.07 ± 1.20 | −0.99 ± 1.24 |
| From Week 13 to end of study | −6.39 ± 1.15 | −1.01 ± 1.17 |

TABLE 16 statistical analysis of rate of change of insulin sensitivity from baseline to end of study efficacy data

| Groups | Vilda 50 mg bid + metformin, Placebo + metformin | From Week 13 to end of Period 1 |
|---|---|---|
| P Value | 0.020 | |
| Method | Mixed Models Analysis | |
| Slope | −5.03 | |
| Standard Error of the mean | 2.16 | |
| 95% Confidence Interval 2-Sided | −9.26 to −0.79 | |

| Groups | Vilda 50 mg bid + metformin, Placebo + metformin | From Week 13 to end of Period 2 |
|---|---|---|
| P Value | 0.03 | |
| Method | Mixed Models Analysis | |
| Slope | −5.08 | |
| Standard Error of the mean | 1.73 | |
| 95% Confidence Interval 2-Sided | −8.46 to −1.69 | |

| Groups | Vilda 50 mg bid + metformin, Placebo + metformin | From Week 13 to end of study |
|---|---|---|
| P Value | 0.001 | |
| Method | Mixed Models Analysis | |
| Slope | −5.38 | |
| Standard Error of the mean | 1.64 | |
| 95% Confidence Interval 2-Sided | −8.61 to −2.16 | |

TABLE 17 percentage of participants with adverse
events, serious adverse events and death

| | Arm/Group Description | |
|---|---|---|
| | Vilda 50 mg bid + metformin vildagliptin (Vilda 50 mg bid) + Metformin | Placebo + metformin Placebo of vildagliptin (Vilda 50 mg bid) + Metformin |
| Number of Participants Analyzed [units: participants] | 998 | 1001 |
| Percentage of participants with adverse events, serious adverse events and death (units: Percentage of Participants) | | |
| On-treatment Adverse Event (AEs) | 83.5 | 83.2 |
| On-treatment Serious Adverse Event (SAEs) | 16.6 | 18.3 |
| On-treatment Deaths | 1.3 | 0.9 |

During the trial, all potential cardiovascular events were subject to adjudication. Over the 5-year study duration, a numerical reduction in the risk of time to first adjudicated macrovascular event was seen with the early combination treatment approach compared with initial monotherapy (HR 0.71 [95% CI 0.42-1.19]; two-sided p=0.19). Adjudicated first macrovascular events occurred in 24 (2.4%) of patients in the combination treatment group and in 33 (3.3%) of patients in the monotherapy group. The absolute cumulative number of recurrent events by treatment approach was low (30 in the combination treatment group vs 44 in the monotherapy group).

The overall safety and tolerability profile was similar between treatment approaches, with no unexpected safety findings reported. The incidence of adverse events and serious adverse events, excluding the cardiovascular events described above but including those considered to be related to the study drug, were similar between the treatment groups (833 (83.5%) had adverse events and 166 (16.6%) had serious adverse events in the combination treatment group, 833 (83.2%) had adverse events and 183 (18.3%) had serious adverse events in the monotherapy group. The incidence of hypoglycaemic events was low, all of them were grade 1 and similar between groups (13 [1.3%] in the combination treatment group, 9 [0.9%] in the monotherapy group). The incidence of events related to pancreatitis (4 [0.4%] in the combination treatment group, 3 [0.3%] in the monotherapy group) and pancreatic carcinoma (3 [0.3%] in the combination treatment group, 2 [0.2%] in the monotherapy group) was also low in both groups. The incidence of neoplasms was low and not significantly different between treatment groups (62 [6.2%] in the combination treatment group vs 54 [5.4%] in the monotherapy group; p=0.43). No bullous pemphigoids were reported. Elevated liver function tests were also rare and balanced between groups. Overall, the 4% annualized rate of discontinuation was low compared with the anticipated rate of 11%, and similar between the groups (4.1% in the combination treatment group, 5.3% in the monotherapy group). 22 deaths were reported during this study (13 in the combination treatment group, 9 in the monotherapy group), none of which were considered related to the study drugs (FIG. 2). The safety results of the VERIFY trial are given in the following tables.

TABLE 18 adverse event reporting groups

| Reporting group totals | Vilda 50 mg bid + metformin | Placebo + metformin | Total |
|---|---|---|---|
| Total # subjects exposed | 998 | 1001 | 1999 |
| Total # subjects affected by serious adverse events | 166 | 183 | 349 |
| Total # subjects affected by non-serious adverse events | 582 | 566 | 1148 |
| Total # of deaths (all causes) | 13 | 9 | 22 |
| Total # of deaths resulting from adverse events | 0 | 0 | 0 |

TABLE 19 serious adverse events by system organ class

| | Arm/Group Description | | |
|---|---|---|---|
| | Vilda 50 mg bid + metformin N = 998 vildagliptin (Vilda 50 mg bid) + Metformin | Placebo + metformin N = 1001 Placebo of vildagliptin (Vilda 50 mg bid) + Metformin | Total N = 1999 Total |
| Total participants affected | 166 (16.63%) | 183 (18.28%) | 349 (17.46%) |
| Blood and lymphatic system disorders | | | |
| Anaemia | 0 (0.00%) | 1 (0.10%) | 1 (0.05%) |
| Cytopenia | 0 (0.00%) | 1 (0.10%) | 1 (0.05%) |
| Hypochromic anaemia | 0 (0.00%) | 1 (0.10%) | 1 (0.05%) |
| Iron deficiency anaemia | 0 (0.00%) | 1 (0.10%) | 1 (0.05%) |
| Lymphadenapathy mediastinal | 0 (0.00%) | 1 (0.10%) | 1 (0.05%) |

TABLE 19-continued serious adverse events by system organ class

| | Arm/Group Description | | |
|---|---|---|---|
| | Vilda 50 mg bid + metformin N = 998 vildagliptin (Vilda 50 mg bid) + Metformin | Placebo + metformin N = 1001 Placebo of vildagliptin (Vilda 50 mg bid) + Metformin | Total N = 1999 Total |
| | Cardiac disorders | | |
| Acute coronary syndrome | 0 (0.00%) | 3 (0.30%) | 3 (0.15%) |
| Acute myocardial infarction | 3 (0.30%) | 4 (0.40%) | 7 (0.35%) |
| Angina pectoris | 2 (0.20%) | 4 (0.40%) | 6 (0.30%) |
| Angina unstable | 2 (0.20%) | 1 (0.10%) | 3 (0.15%) |
| Aortic valve incompetence | 0 (0.00%) | 1 (0.10%) | 1 (0.05%) |
| Arrhythmia | 0 (0.00%) | 1 (0.10%) | 1 (0 05%) |
| Atrial fibrillation | 6 (0.60%) | 5 (0.50%) | 11 (0.55%) |
| Atrial flutter | 0 (0.00%) | 1 (0.10%) | 1 (0.05%) |
| Atrioventricular block complete | 0 (0.00%) | 1 (0.10%) | 1 (0.05%) |
| Atrioventricular block second degree | 0 (0.00%) | 1 (0.10%) | 1 (0.05%) |
| Bundle branch block left | 0 (0.00%) | 1 (0.10%) | 1 (0.05%) |
| Cardiac arrest | 1 (0.10%) | 1 (0.10%) | 2 (0.10%) |
| Cardiac failure | 3 (0.30%) | 4 (0.40%) | 7 (0.35%) |
| Cardiac failure acute | 2 (0.20%) | 1 (0.10%) | 3 (0.15%) |
| Cardiac failure chronic | 1 (0.10%) | 0 (0.00%) | 1 (0.05%) |
| Cardiac failure congestive | 1 (0.10%) | 0 (0.00%) | 1 (0.05%) |
| Cardiogenic shock | 0 (0.00%) | 1 (0.10%) | 1 (0.05%) |
| Conduction disorder | 0 (0.00%) | 2 (0.20%) | 2 (0.10%) |
| Coronary artery disease | 1 (0.10%) | 3 (0.30%) | 4 (0.20%) |
| Coronary artery insufficiency | 0 (0.00%) | 1 (0.10%) | 1 (0.05%) |
| Coronary artery stenosis | 1 (0.10%) | 3 (0.30%) | 4 (0.20%) |
| Mitral valve disease | 0 (0.00%) | 1 (0.10%) | 1 (0.05%) |
| Myocardial infarction | 3 (0.30%) | 7 (0.70%) | 10 (0.50%) |
| Myocardial ischaemia | 2 (0.20%) | 3 (0.30%) | 5 (0.25%) |
| Sinus node dysfunction | 0 (0.00%) | 1 (0.10%) | 1 (0.05%) |
| Sinus tachycardia | 0 (0.00%) | 1 (0.10%) | 1 (0.05%) |
| Supraventricular extrasystoles | 1 (0.10%) | 0 (0.00%) | 1 (0.05%) |
| Supraventricular tachycardia | 0 (0.00%) | 1 (0.10%) | 1 (0.05%) |
| Ventricular fibrillation | 0 (0.00%) | 2 (0.20%) | 2 (0.10%) |
| Ventricular hypokinesia | 0 (0.00%) | 1 (0.10%) | 1 (0.05%) |
| Ventricular tachycardia | 0 (0.00%) | 1 (0.10%) | 1 (0.05%) |
| | Congenital, familial and genetic disorders | | |
| Congenital intestinal malformation | 0 (0.00%) | 1 (0.10%) | 1 (0.05%) |
| Heart disease congenital | 0 (0.00%) | 1 (0.10%) | 1 (0.05%) |
| | Ear and labyrinth disorders | | |
| Acute vestibular syndrome | 0 (0.00%) | 1 (0.10%) | 1 (0.05%) |
| Deafness neurosensory | 1 (0.10%) | 0 (0.00%) | 1 (0.05%) |
| Tinnitus | 1 (0.10%) | 0 (0.00%) | 1 (0.05%) |
| Vertigo | 0 (0.00%) | 1 (0.10%) | 1 (0.05%) |
| Vertigo positional | 1 (0.10%) | 0 (0.00%) | 1 (0.05%) |
| | Endocrine disorders | | |
| Goitre | 1 (0.10%) | 1 (0.10%) | 2 (0.10%) |
| Hypoparathyroidism | 1 (0.10%) | 0 (0.00%) | 1 (0.05%) |
| | Eye disorders | | |
| Diplopia | 1 (0.10%) | 0 (0.00%) | 1 (0.05%) |
| Vitreous haemorrhage | 1 (0.10%) | 0 (0.00%) | 1 (0.05%) |

TABLE 19-continued

| serious adverse events by system organ class | | | |
|---|---|---|---|
| | Arm/Group Description | | |
| | Vilda 50 mg bid + metformin N = 998 vildagliptin (Vilda 50 mg bid) + Metformin | Placebo + metformin N = 1001 Placebo of vildagliptin (Vilda 50 mg bid) + Metformin | Total N = 1999 Total |
| | Gastrointestinal disorders | | |
| Abdominal hernia | 0 (0.00%) | 2 (0.20%) | 2 (0.10%) |
| Abdominal pain | 1 (0.10%) | 0 (0.00%) | 1 (0.05%) |
| Abdominal pain lower | 1 (0.10%) | 0 (0.00%) | 1 (0.05%) |
| Abdominal pain upper | 0 (0.00%) | 1 (0.10%) | 1 (0.05%) |
| Anal fissure | 1 (0.10%) | 0 (0.00%) | 1 (0.05%) |
| Anal haemorrhage | 0 (0.00%) | 1 (0.10%) | 1 (0.05%) |
| Ascites | 0 (0.00%) | 1 (0.10%) | 1 (0.05%) |
| Colitis | 0 (0.00%) | 1 (0.10%) | 1 (0.05%) |
| Diarrhoea | 1 (0.10%) | 0 (0.00%) | 1 (0.05%) |
| Duodenal ulcer haemorrhage | 0 (0.00%) | 1 (0.10%) | 1 (0.05%) |
| Food poisoning | 1 (0.10%) | 1 (0.10%) | 2 (0.10%) |
| Gastric disorder | 0 (0.00%) | 1 (0.10%) | 1 (0.05%) |
| Gastric mucosal lesion | 0 (0.00%) | 1 (0.10%) | 1 (0.05%) |
| Gastric ulcer | 1 (0.10%) | 0 (0.00%) | 1 (0.05%) |
| Gastritis | 1 (0.10%) | 0 (0.00%) | 1 (0.05%) |
| Gastrointestinal erosion | 0 (0.00%) | 1 (0.10%) | 1 (0.05%) |
| Gastrointestinal fistula | 0 (0.00%) | 1 (0.10%) | 1 (0.05%) |
| Gastrointestinal haemorrhage | 2 (0.20%) | 0 (0.00%) | 2 (0.10%) |
| Gastrooesophageal reflux disease | 0 (0.00%) | 1 (0.10%) | 1 (0.05%) |
| Ileus | 1 (0.10%) | 0 (0.00%) | 1 (0.05%) |
| Inguinal hernia | 0 (0.00%) | 7 (0.70%) | 7 (0.35%) |
| Lumbar hernia | 0 (0.00%) | 1 (0.10%) | 1 (0.05%) |
| Pancreatitis | 1 (0.10%) | 0 (0.00%) | 1 (0.05%) |
| Pancreatitis acute | 0 (0.00%) | 2 (0.20%) | 2 (0.10%) |
| Rectal prolapse | 1 (0.10%) | 0 (0.00%) | 1 (0.05%) |
| Retroperitoneal fibrosis | 0 (0.00%) | 1 (0.10%) | 1 (0.05%) |
| Umbilical hernia | 1 (0.10%) | 4 (0.40%) | 5 (0.25%) |
| Upper gastrointestinal haemorrhage | 1 (0.10%) | 2 (0.20%) | 3 (0.15%) |
| Varices oesophageal | 0 (0.00%) | 1 (0.10%) | 1 (0.05%) |
| Vomiting | 1 (0.10%) | 0 (0.00%) | 1 (0.05%) |
| | General disorders and administration site conditions | | |
| Chest pain | 0 (0.00%) | 1 (0.10%) | 1 (0.05%) |
| Death | 2 (0.20%) | 0 (0.00%) | 2 (0.10%) |
| Granuloma | 0 (0.00%) | 1 (0.10%) | 1 (0.05%) |
| Inflammation | 1 (0.10%) | 0 (0.00%) | 1 (0.05%) |
| Non-cardiac chest pain | 1 (0.10%) | 0 (0.00%) | 1 (0.05%) |
| Oedema peripheral | 0 (0.00%) | 1 (0.10%) | 1 (0.05%) |
| Peripheral swelling | 0 (0.00%) | 1 (0.10%) | 1 (0.05%) |
| Pyrexia | 2 (0.20%) | 0 (0.00%) | 2 (0.10%) |
| Stent-graft endoleak | 1 (0.10%) | 0 (0.00%) | 1 (0.05%) |
| Sudden death | 0 (0.00%) | 1 (0.10%) | 1 (0.05%) |
| | Hepatobiliary disorders | | |
| Biliary colic | 0 (0.00%) | 1 (0.10%) | 1 (0.05%) |
| Cholangitis | 0 (0.00%) | 1 (0.10%) | 1 (0.05%) |
| Cholecystitis | 4 (0.40%) | 2 (0.20%) | 6 (0.30%) |
| Cholecystitis acute | 3 (0.30%) | 1 (0.10%) | 4 (0.20%) |
| Cholelithiasis | 2 (0.20%) | 5 (0.50%) | 7 (0.35%) |
| Cholestasis | 0 (0.00%) | 1 (0.10%) | 1 (0.05%) |
| Hepatic cirrhosis | 1 (0.10%) | 0 (0.00%) | 1 (0.05%) |
| Hepatic cyst | 0 (0.00%) | 1 (0.10%) | 1 (0.05%) |
| Hepatic failure | 0 (0.00%) | 1 (0.10%) | 1 (0 05%) |
| Hepatic steatosis | 0 (0.00%) | 1 (0.10%) | 1 (0.05%) |
| Hepatitis toxic | 0 (0.00%) | 1 (0.10%) | 1 (0.05%) |
| Hepatorenal syndrome | 0 (0.00%) | 1 (0.10%) | 1 (0 05%) |

TABLE 19-continued serious adverse events by system organ class

| | Vilda 50 mg bid + metformin N = 998 vildagliptin (Vilda 50 mg bid) + Metformin | Placebo + metformin N = 1001 Placebo of vildagliptin (Vilda 50 mg bid) + Metformin | Total N = 1999 Total |
|---|---|---|---|
| Hydrocholecystis | 1 (0.10%) | 0 (0.00%) | 1 (0.05%) |
| Jaundice cholestatic | 0 (0.00%) | 1 (0.10%) | 1 (0.05%) |
| Liver disorder | 0 (0.00%) | 1 (0.10%) | 1 (0.05%) |
| Immune system disorders | | | |
| Anaphylactic reaction | 2 (0.20%) | 0 (0.00%) | 2 (0.10%) |
| Infections and infestations | | | |
| Abscess limb | 0 (0.00%) | 1 (0.10%) | 1 (0.05%) |
| Acute sinusitis | 0 (0.00%) | 1 (0.10%) | 1 (0.05%) |
| Anal abscess | 1 (0.10%) | 1 (0.10%) | 2 (0.10%) |
| Appendicitis | 2 (0.20%) | 2 (0.20%) | 4 (0.20%) |
| Bartholin's abscess | 1 (0.10%) | 0 (0.00%) | 1 (0.05%) |
| Bone tuberculosis | 1 (0.10%) | 0 (0.00%) | 1 (0.05%) |
| Bronchitis | 1 (0.10%) | 0 (0.00%) | 1 (0.05%) |
| Cervicitis | 0 (0.00%) | 1 (0.10%) | 1 (0.05%) |
| Dengue fever | 2 (0.20%) | 1 (0.10%) | 3 (0.15%) |
| Diarrhoea infectious | 0 (0.00%) | 1 (0.10%) | 1 (0.05%) |
| Diverticulitis | 1 (0.10%) | 1 (0.10%) | 2 (0.10%) |
| Epididymitis | 1 (0.10%) | 0 (0.00%) | 1 (0.05%) |
| Gastroenteritis | 1 (0.10%) | 0 (0.00%) | 1 (0.05%) |
| Gastroenteritis viral | 0 (0.00%) | 1 (0.10%) | 1 (0.05%) |
| Hepatic echinococciasis | 0 (0.00%) | 1 (0.10%) | 1 (0.05%) |
| Hepatitis viral | 1 (0.10%) | 0 (0.00%) | 1 (0.05%) |
| Herpes zoster | 1 (0.10%) | 1 (0.10%) | 2 (0.10%) |
| Infection | 1 (0.10%) | 0 (0.00%) | 1 (0.05%) |
| Lung infection | 1 (0.10%) | 0 (0.00%) | 1 (0.05%) |
| Mastoiditis | 1 (0.10%) | 0 (0.00%) | 1 (0.05%) |
| Meningitis pneumococcal | 1 (0.10%) | 0 (0.00%) | 1 (0.05%) |
| Otitis media chrome | 0 (0.00%) | 1 (0.10%) | 1 (0.05%) |
| Pancreas infection | 0 (0.00%) | 1 (0.10%) | 1 (0.05%) |
| Pneumonia | 14 (1.40%) | 5 (0.50%) | 19 (0.95%) |
| Pyelonephritis | 1 (0.10%) | 0 (0.00%) | 1 (0.05%) |
| Pyelonephritis acute | 1 (0.10%) | 0 (0.00%) | 1 (0.05%) |
| Pyelonephritis chronic | 1 (0.10%) | 0 (0.00%) | 1 (0.05%) |
| Rectal abscess | 1 (0.10%) | 1 (0.10%) | 2 (0.10%) |
| Sepsis | 1 (0.10%) | 1 (0.10%) | 2 (0.10%) |
| Subcutaneous abscess | 0 (0.00%) | 1 (0.10%) | 1 (0.05%) |
| Tooth abscess | 0 (0.00%) | 1 (0.10%) | 1 (0.05%) |
| Urinary tract infection | 2 (0.20%) | 3 (0.30%) | 5 (0.25%) |
| Urinary tract infection bacterial | 0 (0.00%) | 1 (0.10%) | 1 (0.05%) |
| Viral infection | 1 (0.10%) | 0 (0.00%) | 1 (0.05%) |
| Vital myelitis | 1 (0.10%) | 0 (0.00%) | 1 (0.05%) |
| Injury, poisoning and procedural complications | | | |
| Ankle fracture | 0 (0.00%) | 2 (0.20%) | 2 (0.10%) |
| Burns first degree | 0 (0.00%) | 1 (0.10%) | 1 (0.05%) |
| Clavicle fracture | 0 (0.00%) | 1 (0.10%) | 1 (0.05%) |
| Concussion | 1 (0.10%) | 0 (0.00%) | 1 (0.05%) |
| Contusion | 0 (0.00%) | 1 (0.10%) | 1 (0.05%) |
| Craniocerebral injury | 1 (0.10%) | 0 (0.00%) | 1 (0.05%) |
| Face injury | 0 (0.00%) | 1 (0.10%) | 1 (0.05%) |
| Forearm fracture | 1 (0.10%) | 0 (0.00%) | 1 (0.05%) |
| Gun shot wound | 1 (0.10%) | 1 (0.10%) | 2 (0.10%) |
| Heat stoke | 0 (0.00%) | 1 (0.10%) | 1 (0.05%) |
| Hip fracture | 0 (0.00%) | 1 (0.10%) | 1 (0.05%) |
| Humerus fracture | 0 (0.00%) | 1 (0.10%) | 1 (0.05%) |
| Joint dislocation | 0 (0.00%) | 1 (0.10%) | 1 (0.05%) |
| Joint injury | 1 (0.10%) | 0 (0.00%) | 1 (0.05%) |
| Ligament rupture | 1 (0.10%) | 0 (0.00%) | 1 (0.05%) |
| Limb injury | 2 (0.20%) | 1 (0.10%) | 3 (0.15%) |

TABLE 19-continued serious adverse events by system organ class

| | Vilda 50 mg bid + metformin N = 998 vildagliptin (Vilda 50 mg bid) + Metformin | Placebo + metformin N = 1001 Placebo of vildagliptin (Vilda 50 mg bid) + Metformin | Total N = 1999 Total |
|---|---|---|---|
| Lower limb fracture | 0 (0.00%) | 1 (0.10%) | 1 (0.05%) |
| Lumbar vertebral fracture | 1 (0.10%) | 0 (0.00%) | 1 (0.05%) |
| Meniscus injury | 1 (0.10%) | 4 (0.40%) | 5 (0.25%) |
| Multiple injuries | 3 (0.30%) | 0 (0.00%) | 3 (0.15%) |
| Muscle rupture | 1 (0.10%) | 2 (0.20%) | 3 (0.15%) |
| Post procedural fistula | 0 (0.00%) | 1 (0.10%) | 1 (0.05%) |
| Radius fracture | 0 (0.00%) | 3 (0.30%) | 3 (0.15%) |
| Rib fracture | 0 (0.00%) | 1 (0.10%) | 1 (0.05%) |
| Road traffic accident | 0 (0.00%) | 1 (0.10%) | 1 (0.05%) |
| Skin abrasion | 0 (0.00%) | 1 (0.10%) | 1 (0.05%) |
| Skull fracture | 1 (0.10%) | 0 (0.00%) | 1 (0.05%) |
| Tendon rupture | 1 (0.10%) | 0 (0.00%) | 1 (0.05%) |
| Tooth fracture | 0 (0.00%) | 1 (0.10%) | 1 (0.05%) |
| Traumatic arthrosis | 0 (0.00%) | 1 (0.10%) | 1 (0.05%) |
| Ulna fracture | 0 (0.00%) | 1 (0.10%) | 1 (0.05%) |
| Upper limb fracture | 1 (0.10%) | 0 (0.00%) | 1 (0.05%) |
| Investigations | | | |
| Alanine aminotransferase increased | 1 (0.10%) | 0 (0.00%) | 1 (0.05%) |
| Aspartate aminotransferase increased | 1 (0.10%) | 0 (0.00%) | 1 (0.05%) |
| Blood lactate dehydrogenase increased | 1 (0.10%) | 0 (0.00%) | 1 (0.05%) |
| Gamma-glutamyltransferase increased | 1 (0.10%) | 0 (0.00%) | 1 (0.05%) |
| HIV test positive | 1 (0.10%) | 0 (0.00%) | 1 (0.05%) |
| Transaminases increased | 0 (0.00%) | 2 (0.20%) | 2 (0.10%) |
| Metabolism and nutrition disorders | | | |
| Diabetes mellitus | 2 (0.20%) | 1 (0.10%) | 3 (0.15%) |
| Diabetes mellitus inadequate control | 0 (0.00%) | 2 (0.20%) | 2 (0.10%) |
| Hypoglycaemia | 1 (0.10%) | 0 (0.00%) | 1 (0.05%) |
| Hyperkalaemia | 0 (0.00%) | 1 (0.10%) | 1 (0.05%) |
| Type 2 diabetes mellitus | 1 (0.10%) | 0 (0.00%) | 1 (0.05%) |
| Musculoskeletal and connective tissue disorders | | | |
| Exostosis | 0 (0.00%) | 1 (0.10%) | 1 (0.05%) |
| Gouty tophus | 0 (0.00%) | 1 (0.10%) | 1 (0.05%) |
| Intervertebral disc protrusion | 3 (0.30%) | 2 (0.20%) | 5 (0.25%) |
| Joint contracture | 0 (0.00%) | 1 (0.10%) | 1 (0.05%) |
| Joint range of motion decreased | 0 (0.00%) | 1 (0.10%) | 1 (0.05%) |
| Lumbar spinal stenosis | 1 (0.10%) | 0 (0.00%) | 1 (0.05%) |
| Musculoskeletal chest pain | 0 (0.00%) | 1 (0.10%) | 1 (0.05%) |
| Myalgia | 0 (0.00%) | 1 (0.10%) | 1 (0.05%) |
| Osteoarthritis | 2 (0.20%) | 5 (0.50%) | 7 (0.35%) |
| Osteochondrosis | 1 (0.10%) | 2 (0.20%) | 3 (0.15%) |
| Pain in extremity | 0 (0.00%) | 1 (0.10%) | 1 (0.05%) |
| Periarthritis | 1 (0.10%) | 0 (0.00%) | 1 (0.05%) |
| Pseudarthrosis | 0 (0.00%) | 1 (0.10%) | 1 (0.05%) |
| Rotator cuff syndrome | 0 (0.00%) | 1 (0.10%) | 1 (0.05%) |
| Scleroderma | 0 (0.00%) | 1 (0.10%) | 1 (0.05%) |

TABLE 19-continued

| serious adverse events by system organ class | | | |
|---|---|---|---|
| | Arm/Group Description | | |
| | Vilda 50 mg bid + metformin N = 998 vildagliptin (Vilda 50 mg bid) + Metformin | Placebo + metformin N = 1001 Placebo of vildagliptin (Vilda 50 mg bid) + Metformin | Total N = 1999 Total |
| Spinal osteoarthritis | 3 (0.30%) | 1 (0.10%) | 4 (0.20%) |
| Spinal pain | 1 (0.10%) | 1 (0.10%) | 2 (0.10%) |
| Tendonitis | 0 (0.00%) | 1 (0.10%) | 1 (0.05%) |
| Neoplasms benign, malignant and unspecified (incl cysts and polyps) | | | |
| Adenocarcinoma gastric | 1 (0.10%) | 0 (0.00%) | 1 (0.05%) |
| Adenoma benign | 0 (0.00%) | 1 (0.10%) | 1 (005%) |
| Basal cell carcinoma | 0 (0.00%) | 1 (0.10%) | 1 (0.05%) |
| B-cell lymphoma | 0 (0.00%) | 1 (0.10%) | 1 (0.05%) |
| Bladder cancer | 1 (0.10%) | 1 (0.10%) | 2 (0.10%) |
| Brain neoplasm | 1 (0.10%) | 0 (0.00%) | 1 (0.05%) |
| Breast cancer | 3 (0.30%) | 1 (0.10%) | 4 (0.20%) |
| Breast cancer female | 0 (0.00%) | 1 (0.10%) | 1 (0.05%) |
| Choroid melanoma | 1 (0.10%) | 0 (0.00%) | 1 (0.05%) |
| Chronic lymphocytic leukaemia | 1 (0.10%) | 0 (0.00%) | 1 (0.05%) |
| Chronic myeloid leukaemia | 0 (0.00%) | 1 (0.10%) | 1 (0.05%) |
| Colon cancer | 1 (0.10%) | 0 (0.00%) | 1 (0.05%) |
| Cystadenocarcinoma ovary | 1 (0.10%) | 0 (0.00%) | 1 (0.05%) |
| Endometrial cancer | 1 (0.10%) | 0 (0.00%) | 1 (0.05%) |
| Gallbladder neoplasm | 0 (0.00%) | 1 (0.10%) | 1 (0.05%) |
| Gastric cancer | 0 (0.00%) | 1 (0.10%) | 1 (0.05%) |
| Haemangioma | 0 (0.00%) | 1 (0.10%) | 1 (0.05%) |
| Hepatic neoplasm | 0 (0.00%) | 1 (0.10%) | 1 (0.05%) |
| Intestinal adenocarcinoma | 1 (0.10%) | 0 (0.00%) | 1 (0.05%) |
| Invasive ductal breast carcinoma | 1 (0.10%) | 2 (0.20%) | 3 (0.15%) |
| Kaposi's sarcoma | 0 (0.00%) | 1 (0.10%) | 1 (0.05%) |
| Lung neoplasm malignant | 1 (0.10%) | 0 (0.00%) | 1 (0.05%) |
| Malignant melanoma | 2 (0.20%) | 0 (0.00%) | 2 (0.10%) |
| Malignant splenic neoplasm | 0 (0.00%) | 1 (0.10%) | 1 (0.05%) |
| Metastases to bone | 0 (0.00%) | 2 (0.20%) | 2 (0.10%) |
| Metastases to central nervous system | 0 (0.00%) | 1 (0.10%) | 1 (0.05%) |
| Metastases to liver | 1 (0.10%) | 0 (0.00%) | 1 (0.05%) |
| Metastases to lung | 0 (0.00%) | 1 (0.10%) | 1 (0.05%) |
| Metastases to lymph nodes | 0 (0.00%) | 1 (0.10%) | 1 (0.05%) |
| Neuroendocrine tumour | 1 (0.10%) | 0 (0.00%) | 1 (0.05%) |
| Oligoastrocytoma | 1 (0.10%) | 0 (0.00%) | 1 (0.05%) |
| Ovarian adenoma | 0 (0.00%) | 1 (0.10%) | 1 (0.05%) |
| Ovarian cancer metastatic | 1 (0.10%) | 0 (0.00%) | 1 (0.05%) |
| Ovarian epithelial cancer | 0 (0.00%) | 1 (0.10%) | 1 (0.05%) |
| Ovarian neoplasm | 0 (0.00%) | 1 (0.10%) | 1 (0.05%) |
| Pancreatic carcinoma | 3 (0.30%) | 2 (0.20%) | 5 (0.25%) |
| Parathyroid tumour benign | 0 (0.00%) | 1 (0.10%) | 1 (0.05%) |
| Prostate cancer | 6 (0.60%) | 0 (0.00%) | 6 (0.30%) |
| Prostatic adenoma | 1 (0.10%) | 0 (0.00%) | 1 (0.05%) |
| Rectal cancer | 1 (0.10%) | 1 (0.10%) | 2 (0.10%) |
| Rectosigmoid cancer | 0 (0.00%) | 1 (0.10%) | 1 (0.05%) |
| Refractory cytopenia with multilineage dysplasia | 0 (0.00%) | 1 (0.10%) | 1 (0.05%) |
| Renal cancer | 0 (0.00%) | 1 (0.10%) | 1 (0.05%) |
| Renal neoplasm | 0 (0.00%) | 1 (0.10%) | 1 (0.05%) |
| Skin cancer | 0 (0.00%) | 1 (0.10%) | 1 (0.05%) |
| Skin papilloma | 0 (0.00%) | 1 (0.10%) | 1 (0.05%) |
| Small cell carcinoma | 1 (0.10%) | 0 (0.00%) | 1 (0.05%) |

TABLE 19-continued serious adverse events by system organ class

| | Vilda 50 mg bid + metformin N = 998 vildagliptin (Vilda 50 mg bid) + Metformin | Placebo + metformin N = 1001 Placebo of vildagliptin (Vilda 50 mg bid) + Metformin | Total N = 1999 Total |
|---|---|---|---|
| Superficial spreading melanoma stage unspecified | 1 (0.10%) | 0 (0.00%) | 1 (0.05%) |
| Thyroid cancer | 0 (0.00%) | 1 (0.10%) | 1 (0.05%) |
| Tongue neoplasm malignant stage unspecified | 0 (0.00%) | 1 (0.10%) | 1 (0.05%) |
| Tumour haemorrhage | 0 (0.00%) | 1 (0.10%) | 1 (0.05%) |
| Undifferentiated sarcoma | 1 (0.10%) | 0 (0.00%) | 1 (0.05%) |
| Uterine leiomyoma | 2 (0.20%) | 1 (0.10%) | 3 (0.15%) |
| Nervous system disorders | | | |
| Brain oedema | 0 (0.00%) | 1 (0.10%) | 1 (0.05%) |
| Carotid artery stenosis | 1 (0.10%) | 0 (0.00%) | 1 (0.05%) |
| Carpal tunnel syndrome | 0 (0.00%) | 1 (0.10%) | 1 (0.05%) |
| Cerebral haemorrhage | 2 (0.20%) | 1 (0.10%) | 3 (0.15%) |
| Cerebral infarction | 1 (0.10%) | 2 (0.20%) | 3 (0.15%) |
| Cerebral ischaemia | 0 (0.00%) | 4 (0.40%) | 4 (0.20%) |
| Cerebrovascular accident | 2 (0.20%) | 2 (0.20%) | 4 (0.20%) |
| Cerebrovascular disorder | 1 (0.10%) | 0 (0.00%) | 1 (0.05%) |
| Coma | 0 (0.00%) | 1 (0.10%) | 1 (0.05%) |
| Demyelination | 1 (0.10%) | 0 (0.00%) | 1 (0.05%) |
| Haemorrhage intracranial | 1 (0.10%) | 0 (0.00%) | 1 (0.05%) |
| Haemorrhagic stroke | 0 (0.00%) | 1 (0.10%) | 1 (0.05%) |
| Headache | 0 (0.00%) | 1 (0.10%) | 1 (0.05%) |
| Hemiparesis | 1 (0.10%) | 0 (0.00%) | 1 (0.05%) |
| Intracranial pressure increased | 0 (0.00%) | 1 (0.10%) | 1 (0.05%) |
| Ischaemic stroke | 2 (0.20%) | 5 (0.50%) | 7 (0.35%) |
| Loss of consciousness | 0 (0.00%) | 1 (0.10%) | 1 (0.05%) |
| Lumbar radiculopathy | 1 (0.10%) | 0 (0.00%) | 1 (0.05%) |
| Monoparesis | 0 (0.00%) | 1 (0.10%) | 1 (0.05%) |
| Paraesthesia | 0 (0.00%) | 2 (0.20%) | 2 (0.10%) |
| Radiculopathy | 2 (0.20%) | 0 (0.00%) | 2 (0.10%) |
| Sciatica | 3 (0.30%) | 1 (0.10%) | 4 (0.20%) |
| Seizure | 1 (0.10%) | 1 (0.10%) | 2 (0.10%) |
| Syncope | 0 (0.00%) | 2 (0.20%) | 2 (0.10%) |
| Thrombotic cerebral infarction | 0 (0.00%) | 1 (0.10%) | 1 (0.05%) |
| Transient ischaemic attack | 1 (0.10%) | 0 (0.00%) | 1 (0.05%) |
| Vertebrobasilar insufficiency | 0 (0.00%) | 1 (0.10%) | 1 (0.05%) |
| Pregnancy, puerperium and perinatal conditions | | | |
| Abortion missed | 1 (0.10%) | 0 (0.00%) | 1 (0.05%) |
| Abortion spontaneous | 0 (0.00%) | 2 (0.20%) | 2 (0.10%) |
| Abortion threatened | 1 (0.10%) | 0 (0.00%) | 1 (0.05%) |
| Pregnancy with contraceptive device | 1 (0.10%) | 0 (0.00%) | 1 (0.05%) |
| Psychiatric disorders | | | |
| Depression | 1 (0.10%) | 0 (0.00%) | 1 (0.05%) |
| Eating disorder | 0 (0.00%) | 1 (0.10%) | 1 (0.05%) |
| Renal and urinary disorders | | | |
| Bladder tamponade | 1 (0.10%) | 0 (0.00%) | 1 (0.05%) |
| Calculus bladder | 1 (0.10%) | 0 (0.00%) | 1 (0.05%) |
| Chronic kidney disease | 1 (0.10%) | 1 (0.10%) | 2 (0.10%) |
| Diabetic nephropathy | 1 (0.10%) | 0 (0.00%) | 1 (0.05%) |

TABLE 19-continued

| serious adverse events by system organ class | | | |
|---|---|---|---|
| | Arm/Group Description | | |
| | Vilda 50 mg bid + metformin N = 998 vildagliptin (Vilda 50 mg bid) + Metformin | Placebo + metformin N = 1001 Placebo of vildagliptin (Vilda 50 mg bid) + Metformin | Total N = 1999 Total |
| Dysuria | 0 (0.00%) | 1 (0.10%) | 1 (0.05%) |
| Haematuria | 1 (0.10%) | 0 (0.00%) | 1 (0.05%) |
| Hydronephrosis | 1 (0.10%) | 2 (0.20%) | 3 (0.15%) |
| Nephrolithiasis | 3 (0.30%) | 2 (0.20%) | 5 (0.25%) |
| Renal colic | 1 (0.10%) | 2 (0.20%) | 3 (0.15%) |
| Renal failure | 0 (0.00%) | 3 (0.30%) | 3 (0.15%) |
| Renal impairment | 0 (0.00%) | 1 (0.10%) | 1 (0.05%) |
| Stag horn calculus | 1 (0.10%) | 0 (0.00%) | 1 (0.05%) |
| Ureterolithiasis | 1 (0.10%) | 1 (0.10%) | 2 (0.10%) |
| Urethral stenosis | 0 (0.00%) | 1 (0.10%) | 1 (0.05%) |
| Urinary incontinence | 0 (0.00%) | 1 (0.10%) | 1 (0.05%) |
| Urinary retention | 1 (0.10%) | 0 (0.00%) | 1 (0.05%) |
| Urinary tract obstruction | 0 (0.00%) | 1 (0.10%) | 1 (0.05%) |
| Reproductive system and breast disorders | | | |
| Benign prostatic hyperplasia | 2 (0.20%) | 0 (0.00%) | 2 (0.10%) |
| Cervical cyst | 0 (0.00%) | 1 (0.10%) | 1 (0.05%) |
| Dysfunctional uterine bleeding | 1 (0.10%) | 0 (0.00%) | 1 (0.05%) |
| Endometrial hyperplasia | 1 (0.10%) | 0 (0.00%) | 1 (0.05%) |
| Endometrial thickening | 0 (0.00%) | 1 (0.10%) | 1 (0.05%) |
| Endometriosis | 0 (0.00%) | 1 (0.10%) | 1 (0.05%) |
| Genital ulceration | 0 (0.00%) | 1 (0.10%) | 1 (0.05%) |
| Metrorrhagia | 1 (0.10%) | 0 (0.00%) | 1 (0.05%) |
| Ovarian cyst | 1 (0.10%) | 4 (0.40%) | 5 (0.25%) |
| Ovarian fibrosis | 0 (0.00%) | 1 (0.10%) | 1 (0.05%) |
| Prostatomegaly | 0 (0.00%) | 1 (0.10%) | 1 (0.05%) |
| Uterine polyp | 1 (0.10%) | 2 (0.20%) | 3 (0.15%) |
| Respiratory, thoracic and mediastinal disorders | | | |
| Acute respiratory failure | 0 (0.00%) | 2 (0.20%) | 2 (0.10%) |
| Asthma | 1 (0.10%) | 0 (0.00%) | 1 (0.05%) |
| Chronic obstructive pulmonary disease | 2 (0.20%) | 3 (0.30%) | 5 (0.25%) |
| Chronic respiratory failure | 0 (0.00%) | 1 0.10%) | 1 (0.05%) |
| Dyspnoea | 1 (0.10%) | 0 (0.00%) | 1 (0.05%) |
| Laryngeal cyst | 1 (0.10%) | 0 (0.00%) | 1 (0.05%) |
| Pneumonitis | 0 (0.00%) | 1 (0.10%) | 1 (0.05%) |
| Pulmonary embolism | 1 (0.10%) | 0 (0.00%) | 1 (0.05%) |
| Pulmonary mass | 1 (0.10%) | 0 (0.00%) | 1 (0.05%) |
| Respiratory failure | 1 (0.10%) | 0 (0.00%) | 1 (0.05%) |
| Skin and subcutaneous tissue disorders | | | |
| Angioedema | 1 (0.10%) | 0 (0.00%) | 1 (0.05%) |
| Diabetic foot | 0 (0.00%) | 1 (0.10%) | 1 (0.05%) |
| Eczema | 0 (0.00%) | 1 (0.10%) | 1 (0.05%) |
| Skin lesion | 0 (0.00%) | 1 (0.10%) | 1 (0.05%) |
| Skin ulcer haemorrhage | 1 (0.10%) | 0 (0.00%) | 1 (0.05%) |
| Urticaria | 1 (0.10%) | 0 (0.00%) | 1 (0.05%) |
| Vascular disorders | | | |
| Aortic aneurysm | 2 (0.20%) | 0 (0.00%) | 2 (0.10%) |
| Aortic dissection | 1 (0.10%) | 0 (0.00%) | 1 (0.05%) |
| Aortic stenosis | 2 (0.20%) | 0 (0.00%) | 2 (0.10%) |
| Deep vein thrombosis | 2 (0.20%) | 0 (0.00%) | 2 (0.10%) |
| Haematoma | 0 (0.00%) | 1 (0.10%) | 1 (0.05%) |

TABLE 19-continued serious adverse events by system organ class

| | Arm/Group Description | | |
|---|---|---|---|
| | Vilda 50 mg bid + metformin N = 998 vildagliptin (Vilda 50 mg bid) + Metformin | Placebo + metformin N = 1001 Placebo of vildagliptin (Vilda 50 mg bid) + Metformin | Total N = 1999 Total |
| Hypertension | 2 (0.20%) | 4 (0.40%) | 6 (0.30%) |
| Hypertensive crisis | 1 (0.10%) | 0 (0.00%) | 1 (0.05%) |
| Pelvic venous thrombosis | 0 (0.00%) | 1 (0.10%) | 1 (0.05%) |
| Peripheral arterial occlusive disease | 0 (0.00%) | 2 (0.20%) | 2 (0.10%) |
| Peripheral artery stenosis | 1 (0.10%) | 0 (0.00%) | 1 (0.05%) |
| Peripheral venous disease | 1 (0.10%) | 0 (0.00%) | 1 (0.05%) |
| Varicose vein | 2 (0.20%) | 1 (0.10%) | 3 (0.15%) |

| | |
|---|---|
| Time frame | Adverse events were collected from first dose of study treatment until end of study treatment plus 30 days post treatment, up to a maximum duration of 75.6 months |
| Additional description | Any sign or symptom that occurs during the study treatment plus the 30 days post treatment. Maximum exposure to study treatments = 75.6 months (Vilda 50 mg bid + metformin arm) and 66.2 months (placebo + metformin arm) |
| Source vocabulary for Table Default | MedDRA (21.1) |
| Assessment Type for Table Default | Systematic Assessment |

TABLE 20 other adverse events by system organ class

| | Arm/Group Description | | |
|---|---|---|---|
| | Vilda 50 mg bid + metformin N = 998 vildagliptin (Vilda 50 mg bid) + Metformin | Placebo + metformin N = 1001 Placebo of vildagliptin (Vilda 50 mg bid) + Metformin | Total N = 1999 Total |
| Total participants affected | 582 (58.32%) | 566 (56.54%) | 1148 (57.43%) |
| *Gastrointestinal disorders* | | | |
| Diarrhoea | 104 (10.42%) | 104 (10.39%) | 208 (10.41%) |
| *Infections and infestations* | | | |
| Bronchitis | 58 (5.81%) | 59 (5.89%) | 117 (5.85%) |
| Influenza | 93 (9.32%) | 64 (6.39%) | 157 (7.85%) |
| Nasopharyngitis | 104 (10.42%) | 108 (10.79%) | 212 (10.61%) |
| Upper respiratory tract infection | 83 (8.32%) | 69 (6.89%) | 152 (7.60%) |
| Urinary tract infection | 72 (7.21%) | 69 (6.89%) | 141 (7.05%) |

TABLE 20-continued other adverse events by system organ class

| | Arm/Group Description | | |
|---|---|---|---|
| | Vilda 50 mg bid + metformin N = 998 vildagliptin (Vilda 50 mg bid) + Metformin | Placebo + metformin N = 1001 Placebo of vildagliptin (Vilda 50 mg bid) + Metformin | Total N = 1999 Total |
| *Metabolism and nutrition disorders* | | | |
| Dyslipidaemia | 58 (5.81%) | 71 (7.09%) | 129 (6.45%) |
| *Musculoskeletal and connective tissue disorders* | | | |
| Arthralgia | 100 (10.02%) | 94 (9.39%) | 194 (9.70%) |
| Back pain | 105 (10.52%) | 86 (8.59%) | 191 (9.55%) |
| Osteoarthritis | 54 (5.41%) | 40 (4.00%) | 94 (4.70%) |
| Pain in extremity | 67 (6.71%) | 74 (7.39%) | 141 (7.05%) |
| *Nervous system disorders* | | | |
| Dizziness | 67 (6.71%) | 41 (4.10%) | 108 (5.40%) |
| Headache | 82 (0.22%) | 72 (7.19%) | 154 (7.70%) |
| *Vascular disorders* | | | |
| Hypertension | 103 (10.32%) | 124 (12.39%) | 227 (11.36%) |

| | |
|---|---|
| Time frame | Adverse events were collected from first dose of study treatment until end of study treatment plus 30 days post treatment, up to a maximum duration of 75.6 months |
| Additional description | Any sign or symptom that occurs during the study treatment plus the 30 days post treatment. Maximum exposure to study treatments = 75.6 months (Vilda 50 mg big + metformin arm) and 66.2 months (placebo + metformin arm) |

| | |
|---|---|
| Source vocabulary for table default | MedDRA (21.1) |
| Assessment type for table default | Systematic Assessment |
| Frequent event reporting threshold | 5% |

DISCUSSION

The VERIFY study has shown that early combination treatment with metformin and vildagliptin improves glycaemic durability in patients with type 2 diabetes compared with standard-of-care initial metformin monotherapy followed by sequential combination with vildagliptin. Early combination treatment significantly reduced the probability of initial treatment failure, the time to second treatment failure, and the time to treatment failure compared with monotherapy throughout the 5-year study duration. Secondary glycaemic parameters (loss of glycaemic control) support the durability of the combination approach. The longer time to second treatment failure in the combination treatment group showed that the observations were not simply the result of comparing a therapy of two drugs with a therapy of one, since all patients entering period 2 received the combination therapy. Finally, the early combination treatment was safe and well tolerated.

VERIFY is the first study to examine long-term clinical benefits of an early combination treatment strategy and provides a step forward with respect to previous approaches. What was considered as intensive therapy in UKPDS is the comparator treatment strategy in VERIFY, reflecting enhanced understanding of the pathophysiological mechanisms underlying the progressive nature of type 2 diabetes and the expanded therapeutic armamentarium.

The early combination treatment was well tolerated, with no signal for adverse events of special interest, in line with previous evidence from vildagliptin studies. As part of safety surveillance, cardiovascular events were monitored and adjudicated. Surprisingly, an imbalance favouring the early combination treatment was observed. Such an observation, obtained in a low-risk population, is unexpected because it is at odds with the neutral cardiovascular effect reported in cardiovascular outcomes trials of patients with long-standing type 2 diabetes and much greater cardiovascular risk. It is noteworthy that no other antidiabetic medication has demonstrated any benefit in preventing primary cardiovascular events to date.

In conclusion, the strategy of an early combination treatment approach with vildagliptin plus metformin in patients with newly diagnosed type 2 diabetes significantly and consistently improves long-term glycaemic durability compared with metformin monotherapy. The results indicate that long-term clinical benefits can be achieved more frequently and without tolerability issues with early combination treatment compared with standard-of-care metformin monotherapy.

Without further description, it is believed that one of ordinary skill in the art can, using the preceding description and the illustrative examples, make, utilize, and practice the invention described herein. It should be understood that the foregoing discussion and examples merely present a detailed description of certain preferred embodiments. It will be apparent to those of ordinary skill in the art that various modifications and equivalents can be made without departing from the spirit and scope of the invention.

The invention is further defined with reference to the following clauses:

1. A combination of vildagliptin or a pharmaceutically acceptable salt thereof, and metformin or a pharmaceutically acceptable salt thereof, for use in a method of delaying loss of glycaemic control in a patient with type 2 diabetes mellitus.
2. The combination for use according to clause 1, wherein, the patient has not previously received pharmaceutical treatment for the type 2 diabetes mellitus.
3. The combination for use according to clause 1 or clause 2, wherein the loss of glycaemic control is delayed relative to metformin monotherapy.
4. The combination for use according to any preceding clause, wherein the loss of glycaemic control is delayed relative to metformin monotherapy followed by subsequent co-administration of a DPP-IV inhibitor and metformin or a pharmaceutically acceptable salt thereof.
5. The combination for use according to clause 4, wherein the DPP-IV inhibitor is vildagliptin or a pharmaceutically acceptable salt thereof.
6. A combination of vildagliptin or a pharmaceutically acceptable salt thereof, and metformin or a pharmaceutically acceptable salt thereof, for use in a method of improving glycaemic control in a patient with type 2 diabetes mellitus.
7. The combination for use according to clause 6, wherein, the patient has not previously received pharmaceutical treatment for the type 2 diabetes mellitus.
8. The combination for use according to clause 6 or clause 7, wherein the improvement in glycaemic control is relative to metformin monotherapy.
9. The combination for use according to any of clause 6-8, wherein the improvement in glycaemic control is relative to metformin monotherapy followed by subsequent co-administration of a DPP-IV inhibitor and metformin or a pharmaceutically acceptable salt thereof.
10. The combination for use according to clause 9, wherein the DPP-IV inhibitor is vildagliptin or a pharmaceutically acceptable salt thereof.
11. A combination of vildagliptin or a pharmaceutically acceptable salt thereof, and metformin or a pharmaceutically acceptable salt thereof, for use in a method of delaying the increase of $HbA_{1c}$ to greater than or equal to 53 mmol/mol (7.0%) in a patient with type 2 diabetes mellitus.
12. The combination for use according to clause 11, wherein the patient has not previously received pharmaceutical treatment for the type 2 diabetes mellitus.
13. The combination for use according to clause 11 or clause 12, wherein the delay in the increase of $HbA_{1c}$ is relative to metformin monotherapy.
14. The combination for use according to any of clause 11-13, wherein the delay in the increase of $HbA_{1c}$ is relative to metformin monotherapy followed by subsequent co-administration of a DPP-IV inhibitor and metformin or a pharmaceutically acceptable salt thereof.
15. The combination for use according to clause 14, wherein the DPP-IV inhibitor is vildagliptin or a pharmaceutically acceptable salt thereof.
16. A combination of vildagliptin or a pharmaceutically acceptable salt thereof, and metformin or a pharmaceutically acceptable salt thereof, for use in a method of increasing the time taken to reach an HbA$_{1c}$ measurement of greater than or equal to 53 mmol/mol (7.0%) in a patient with type 2 diabetes mellitus.

17. The combination for use according to clause 16, wherein the patient has not previously received pharmaceutical treatment for the type 2 diabetes mellitus.

18. The combination for use according to clause 16 or clause 17, wherein the increase in the time taken is delayed relative to metformin monotherapy.

19. The combination for use according to any of clauses 16-18, wherein the increase in the time taken is relative to metformin monotherapy followed by subsequent co-administration of a DPP-IV inhibitor and metformin or a pharmaceutically acceptable salt thereof.

20. The combination for use according to clause 19, wherein the DPP-IV inhibitor is vildagliptin or a pharmaceutically acceptable salt thereof.

21. A combination of vildagliptin or a pharmaceutically acceptable salt thereof, and metformin or a pharmaceutically acceptable salt thereof, for use in a method of preventing loss of glycaemic control in a patient with type 2 diabetes mellitus.

22. The combination for use according to clause 21, wherein the patient has not previously received pharmaceutical treatment for the type 2 diabetes mellitus.

23. A combination of vildagliptin or a pharmaceutically acceptable salt thereof, and metformin or a pharmaceutically acceptable salt thereof, for use in a method of reducing the risk of a cardiovascular event in a patient undergoing treatment for type 2 diabetes mellitus.

24. The combination for use according to clause 23, wherein the patient has not previously received pharmaceutical treatment for the type 2 diabetes mellitus.

25. The combination for use according to clause 23 or clause 24, wherein the risk is reduced relative to metformin monotherapy.

26. The combination for use according to any of clauses 23-25, wherein the risk is reduced relative to metformin monotherapy followed by subsequent co-administration of a DPP-IV inhibitor and metformin or a pharmaceutically acceptable salt thereof.

27. The combination for use according to clause 26, wherein the DPP-IV inhibitor is vildagliptin or a pharmaceutically acceptable salt thereof.

28. A combination of vildagliptin or a pharmaceutically acceptable salt thereof, and metformin or a pharmaceutically acceptable salt thereof, for use in a method of treating type 2 diabetes mellitus without concomitant administration of insulin.

29. The combination for use according to clause 28, wherein the patient has not previously received pharmaceutical treatment for the type 2 diabetes mellitus.

30. Vildagliptin or a pharmaceutically acceptable salt thereof, for use in a method of delaying loss of glycaemic control in a patient with type 2 diabetes mellitus, wherein the vildagliptin or a pharmaceutically acceptable salt thereof, is co-administered with metformin or a pharmaceutically acceptable salt thereof.

31. Vildagliptin or a pharmaceutically acceptable salt thereof, for use according to clause 30, wherein the patient has not previously received pharmaceutical treatment for the type 2 diabetes mellitus.

32. Vildagliptin or a pharmaceutically acceptable salt thereof, for use according to clause or clause 31, wherein the loss of glycaemic control is delayed relative to metformin monotherapy.

33. Vildagliptin or a pharmaceutically acceptable salt thereof, for use according to any of clauses 30-32, wherein the loss of glycaemic control is delayed relative to metformin monotherapy followed by subsequent co-administration of a DPP-IV inhibitor and metformin or a pharmaceutically acceptable salt thereof.

34. Vildagliptin or a pharmaceutically acceptable salt thereof, for use according to clause 33, wherein the DPP-IV inhibitor is vildagliptin or a pharmaceutically acceptable salt thereof, wherein the vildagliptin or a pharmaceutically acceptable salt thereof, is co-administered with metformin or a pharmaceutically acceptable salt thereof.

35. Vildagliptin or a pharmaceutically acceptable salt thereof, for use in a method of delaying the increase of HbA$_{1c}$ to greater than or equal to 53 mmol/mol (7.0%) in a patient with type 2 diabetes mellitus, wherein the vildagliptin or a pharmaceutically acceptable salt thereof, is co-administered with metformin or a pharmaceutically acceptable salt thereof.

36. Vildagliptin or a pharmaceutically acceptable salt thereof, for use according to clause 35, wherein the patient has not previously received pharmaceutical treatment for the type 2 diabetes mellitus.

37. Vildagliptin or a pharmaceutically acceptable salt thereof, for use according to clause or clause 36, wherein the delay in the increase of HbA$_{1c}$ is relative to metformin monotherapy.

38. Vildagliptin or a pharmaceutically acceptable salt thereof, for use according to any of clauses 35-37, wherein the delay in the increase of HbA$_{1c}$ is relative to metformin monotherapy followed by subsequent co-administration of a DPP-IV inhibitor and metformin or a pharmaceutically acceptable salt thereof.

39. Vildagliptin or a pharmaceutically acceptable salt thereof for use according to clause 38, wherein the DPP-IV inhibitor is vildagliptin or a pharmaceutically acceptable salt thereof.

40. Vildagliptin or a pharmaceutically acceptable salt thereof, for use in a method of increasing the time taken to reach an HbA$_{1c}$ measurement of greater than or equal to 53 mmol/mol (7.0%) in a patient with type 2 diabetes mellitus, wherein the vildagliptin or a pharmaceutically acceptable salt thereof, is co-administered with metformin or a pharmaceutically acceptable salt thereof.

41. Vildagliptin or a pharmaceutically acceptable salt thereof for use according to clause 40, wherein the patient has not previously received pharmaceutical treatment for the type 2 diabetes mellitus.

42. Vildagliptin or a pharmaceutically acceptable salt thereof for use according to clause or clause 41, wherein the increase in time taken is relative to metformin monotherapy.

43. Vildagliptin or a pharmaceutically acceptable salt thereof for use according to any of clauses 40-42, wherein the increase in the time taken is relative to metformin monotherapy followed by subsequent co-administration of a DPP-IV inhibitor and metformin or a pharmaceutically acceptable salt thereof.

44. Vildagliptin or a pharmaceutically acceptable salt thereof for use according to clause 43 wherein the DPP-IV inhibitor is vildagliptin or a pharmaceutically acceptable salt thereof.

45. Vildagliptin or a pharmaceutically acceptable salt thereof for use in a method of preventing loss of glycaemic control in a patient with type 2 diabetes mellitus, wherein the vildagliptin or a pharmaceutically acceptable salt thereof is co-administered with metformin or a pharmaceutically acceptable salt thereof.
46. Vildagliptin or a pharmaceutically acceptable salt thereof for use according to clause 45, wherein the patient has not previously received pharmaceutical treatment for the type 2 diabetes mellitus.
47. Vildagliptin or a pharmaceutically acceptable salt thereof, for use in a method of reducing the risk of a cardiovascular event in a patient undergoing treatment for type 2 diabetes mellitus, wherein the vildagliptin or a pharmaceutically acceptable salt thereof is co-administered with metformin or a pharmaceutically acceptable salt thereof.
48. Vildagliptin or a pharmaceutically acceptable salt thereof for use according to clause 47, wherein the patient has not previously received pharmaceutical treatment for the type 2 diabetes mellitus.
49. Vildagliptin or a pharmaceutically acceptable salt thereof for use according to clause 47 or clause 48, wherein the risk is reduced relative to metformin monotherapy.
50. Vildagliptin or a pharmaceutically acceptable salt thereof for use according to any of clauses 47-49, wherein the risk is reduced relative to metformin monotherapy followed by subsequent co-administration of a DPP-IV inhibitor and metformin or a pharmaceutically acceptable salt thereof.
51. Vildagliptin or a pharmaceutically acceptable salt thereof for use according to clause 50, wherein the DPP-IV inhibitor is vildagliptin or a pharmaceutically acceptable salt thereof.
52. Vildagliptin or a pharmaceutically acceptable salt thereof, and metformin or a pharmaceutically acceptable salt thereof, for use in a method of treating type 2 diabetes mellitus without concomitant administration of insulin, wherein the vildagliptin or a pharmaceutically acceptable salt thereof is co-administered with metformin or a pharmaceutically acceptable salt thereof.
53. Vildagliptin or a pharmaceutically acceptable salt thereof for use according to clause 52, wherein the patient has not previously received pharmaceutical treatment for the type 2 diabetes mellitus.

The invention claimed is:
1. A method of delaying loss of glycaemic control for 5 years or more in a patient with type 2 diabetes mellitus, wherein the method comprises co-administering 1 mg to 200 mg per day of a DPP-IV inhibitor and 1000 mg to 2550 mg per day of metformin or a pharmaceutically acceptable salt thereof, wherein the DPP-IV inhibitor and the metformin or a pharmaceutically acceptable salt thereof are comprised within a single oral dosage form, or wherein the DPP-IV inhibitor is comprised within a first oral dosage form, and the metformin or a pharmaceutically acceptable salt thereof is comprised within a second, separate oral dosage form, wherein the patient has not previously received pharmaceutical treatment for type 2 diabedes melliyus or the patient has received metformin monotherapy for no longer than 3 months prior to being co-administered the DDP-IV inhibitor and the metfoemin or a pharmaceutically acceptable salt thereof.
2. The method of claim 1, wherein the patient has not previously received pharmaceutical treatment for the type 2 diabetes mellitus.
3. The method of claim 1, wherein the patient has received metformin monotherapy for no longer than 3 months prior to being co-administered the DPP-IV inhibitor and the metformin or a pharmaceutically acceptable salt thereof.
4. The method of claim 1, wherein the patient has been diagnosed with type 2 diabetes mellitus for less than 2 years prior to being co-administered the DPP-IV inhibitor and the metformin or a pharmaceutically acceptable salt thereof.
5. The method of claim 1, wherein the DPP-IV inhibitor and the metformin or a pharmaceutically acceptable salt thereof are not administered with any further antidiabetic agents.
6. The method of claim 1, wherein the method reduces the risk of the patient experiencing a cardiovascular event.
7. The method of claim 6, wherein the cardiovascular event is a macrovascular event which is optionally selected from the group consisting of cardiovascular death, non-fatal myocardial infarction or stroke, and hospital admission for heart failure.
8. The method of claim 1, wherein the method does not increase the patient's risk of hypoglycaemia.
9. The method of claim 8, wherein the method does not increase the patient's risk of hypoglycaemia relative to metformin monotherapy.
10. The method of claim 1, wherein the delay in loss of glycaemic control is relative to metformin monotherapy.
11. The method of claim 1, wherein the delay in loss of glycaemic control is relative to metformin monotherapy followed by subsequent co-administration of a DPP-IV inhibitor and metformin or a pharmaceutically acceptable salt thereof.
12. The method of claim 1, wherein the co-administration is for 5 years or more.
13. The method of claim 1, wherein the DPP-IV inhibitor and the metformin or a pharmaceutically acceptable salt thereof are comprised within a single oral dosage form.
14. The method of claim 1, wherein the DPP-IV inhibitor is comprised within a first oral dosage form, and the metformin or a pharmaceutically acceptable salt thereof is comprised within a second, separate oral dosage form.

* * * * *

UNITED STATES PATENT AND TRADEMARK OFFICE
CERTIFICATE OF CORRECTION

PATENT NO. : 12,090,125 B2
APPLICATION NO. : 17/385008
DATED : September 17, 2024
INVENTOR(S) : Päivi M. Paldánius et al.

Page 1 of 1

It is certified that error appears in the above-identified patent and that said Letters Patent is hereby corrected as shown below:

In the Claims

Column 122, Claim 1, Line 4, replace "diabedes melliyus" with --diabetes mellitus--;
Line 7, replace "metfoemin" with --metformin--.

Signed and Sealed this
Seventh Day of January, 2025

Derrick Brent
*Acting Director of the United States Patent and Trademark Office*